United States Patent
Deng et al.

(10) Patent No.: US 10,501,477 B2
(45) Date of Patent: Dec. 10, 2019

(54) PHOTOCHROMIC THIENOCHROMENE COMPOUNDS

(71) Applicant: Transitions Optical, Inc., Pinellas Park, FL (US)

(72) Inventors: Jun Deng, Mars, PA (US); Brian R. Stepp, Pittsburgh, PA (US); Eric Spitler, Pittsburgh, PA (US); Wenjing Xiao, Murrysville, PA (US); Massimiliano Tomasulo, Monroeville, PA (US); Robert W. Walters, Export, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 15/556,672

(22) PCT Filed: Mar. 10, 2015

(86) PCT No.: PCT/US2015/019575
§ 371 (c)(1),
(2) Date: Sep. 8, 2017

(87) PCT Pub. No.: WO2016/144324
PCT Pub. Date: Sep. 15, 2016

(65) Prior Publication Data
US 2018/0051037 A1    Feb. 22, 2018

(51) Int. Cl.
*G02B 5/23* (2006.01)
*C07D 491/10* (2006.01)
(Continued)

(52) U.S. Cl.
CPC ......... *C07D 495/14* (2013.01); *C07D 493/14* (2013.01); *C09K 9/02* (2013.01); *G02B 5/23* (2013.01); *G03C 1/73* (2013.01)

(58) Field of Classification Search
CPC ...... C07D 493/14; C07D 495/14; C09K 9/02; G02B 5/23; G03C 1/73
See application file for complete search history.

(56) References Cited

U.S. PATENT DOCUMENTS 4,931,220 A    6/1990   Haynes et al.
5,645,767 A    7/1997   Van Gemert
(Continued)

FOREIGN PATENT DOCUMENTS

WO    0018755 A1    4/2000
WO    0077007 A1    12/2000

OTHER PUBLICATIONS

Gabbutt et al., "Photchromism of Some Heterobenzopyrans", Molecular Crystals and Liquid Crystals Science and Technology Section A., Molecular Crystals and Liquid Crystals, 2000, vol. 344:1, pp. 229-234.
(Continued)

*Primary Examiner* — Bijan Ahvazi
(74) *Attorney, Agent, or Firm* — The Webb Law Firm

(57) ABSTRACT

The present invention relates to photochromic compounds, such as thienochromene compounds represented by the following Formulas (1a) and/or (1b). The present invention also relates to photochromic compositions and articles containing one or more such photochromic thienochromene compounds.
(Continued)

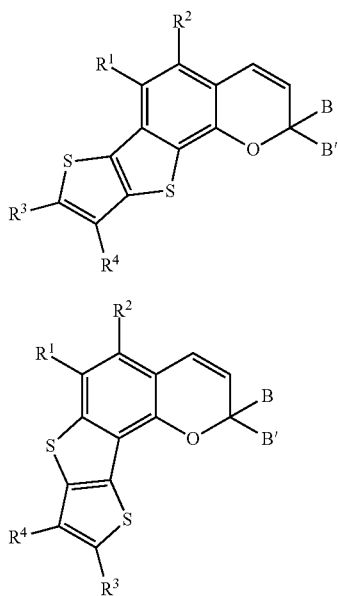

12 Claims, 7 Drawing Sheets

(51) Int. Cl.
*G02F 1/00* (2006.01)
*C07D 495/14* (2006.01)
*C07D 493/14* (2006.01)
*C09K 9/02* (2006.01)
*G03C 1/73* (2006.01)

(56) References Cited

U.S. PATENT DOCUMENTS

| | | | |
|---|---|---|---|
| 5,658,501 A | 8/1997 | Kumar et al. | |
| 5,698,141 A | 12/1997 | Kumar | |
| 5,723,072 A | 3/1998 | Kumar | |
| 6,022,497 A | 2/2000 | Kumar | |
| 6,113,814 A | 9/2000 | Gemert et al. | |
| 6,153,126 A | 11/2000 | Kumar | |
| 6,387,512 B1 | 5/2002 | Clarke et al. | |
| 6,426,023 B1 | 7/2002 | Breyne et al. | |
| 6,555,028 B2 | 4/2003 | Walters et al. | |
| 8,647,538 B2 | 2/2014 | Lu et al. | |
| 8,778,236 B2 | 7/2014 | Takenaka et al. | |
| 2004/0094753 A1* | 5/2004 | Izumi | C07D 311/78 252/586 |
| 2005/0004361 A1* | 1/2005 | Kumar | C07D 311/94 544/71 |
| 2012/0136148 A1* | 5/2012 | Lu | C09K 9/02 544/79 |

OTHER PUBLICATIONS

Oliveira et al., "Synthesis and photochromic behaviour under flash photolysis and continuous irradiation of novel 2H-chromenes derived from hydroxydibenzothiophenes", Tetrahedron, 2002, vol. 58:9, pp. 1709-1718.

Queiroz et al., "Synthesis and photochromic behaviour of new methyl induced linear and angular thieno-2H-chromenes", Tetrahedron, 2003, vol. 59:14, pp. 2567-2573.

* cited by examiner

Scheme-(2)

Scheme-(4)

Scheme-(5)

Scheme-(6)

Scheme-(7)

PHOTOCHROMIC THIENOCHROMENE COMPOUNDS

CROSS-REFERENCE TO RELATED APPLICATION

This application is the United States national phase of International Application No. PCT/US2015/019575 filed Mar. 10, 2015, which is incorporated herein by reference in its entirety.

FIELD

The present invention relates to thieno-thienyl cyclopyran compounds that have photochromic properties, and photochromic compositions and articles containing such compounds.

BACKGROUND

Photochromic compounds and materials, in response to certain wavelengths of electromagnetic radiation (or "actinic radiation"), typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, or substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (such as in form of a photochromic coating composition) typically display colorless (or clear) and colored states that correspond to the colorless and colored states of the photochromic materials contained therein and/or applied thereto. Photochromic compounds and materials are typically characterized with regard to various properties, such as photochromic properties, which include, but are not limited to, fade rate, change in optical density (sometimes designated as ΔOD), and dichroic properties.

It would be desirable to develop new photochromic compounds. It would be further desirable that such newly developed photochromic compounds possess properties, such as photochromic properties, that are at least the same as or better than those of existing photochromic compounds.

SUMMARY

In accordance with the present invention, there is provided a photochromic compound represented by at least one of the following Formulas (Ia) and (Ib),

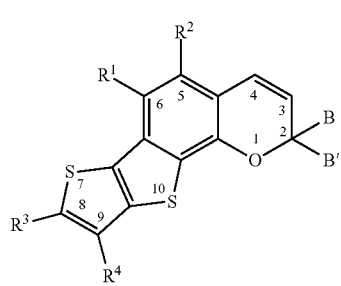

(Ia)

and

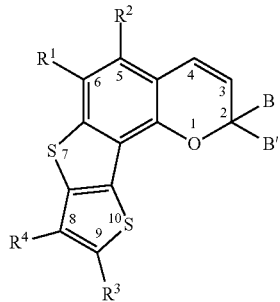

(Ib)

Independently for each of Formulas (Ia) and (Ib), $R^1$, $R^2$, $R^3$, and $R^4$ are in each case independently selected from, hydrogen; hydrocarbyl; substituted hydrocarbyl; interrupted hydrocarbyl; substituted interrupted hydrocarbyl, wherein each interrupted hydrocarbyl and each substituted interrupted hydrocarbyl, are in each case independently interrupted with at least one interrupting group selected from the group consisting of —O—, —S—, —C(O)—, —C(O)O—, —OC(O)O—, —B($R_{11}'$)—, —P($R_{11}'$), —P(O)($R_{11}'$)—, —S(O)—, —SO$_2$—, —N=N—, —C(O)N($R_{11}'$)—, —OC(O)N($R_{11}'$)—, —N($R_{11}'$)C(O)N($R_{11}'$)—, —N($R_{11}'$)— where $R_{11}'$ in each case is independently selected from hydrogen, hydrocarbyl or substituted hydrocarbyl, —Si(O$R_8'$)$_w$($R_8'$)$_t$—, where w and t are each independently selected from 0 to 2, provided that the sum of w and t is 2, and each $R_8'$ is independently selected from hydrogen, hydrocarbyl and substituted hydrocarbyl, and combinations of two or more interrupting groups thereof; halogen; cyano; and —N($R_{11}''$)$R_{12}'$, wherein $R_{11}''$ and $R_{12}'$ are each independently selected from hydrogen, hydrocarbyl or substituted hydrocarbyl, or $R_{11}''$ and $R_{12}'$ together form a ring structure or a ring structure including at least one heteroatom; or $R^1$ and $R^2$ together form a ring structure; or $R^3$ and $R^4$ together form a ring structure.

Independently for each of Formulas (Ia) and (Ib), B and B' are each independently selected from unsubstituted aryl, substituted aryl, unsubstituted heteroaryl, substituted heteroaryl, alkenyl, and alkynyl, or B and B' taken together form a ring structure.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1-7 like characters refer to the same compounds and/or reactants, as the case may be, unless otherwise stated.

DETAILED DESCRIPTION

Figure 1:
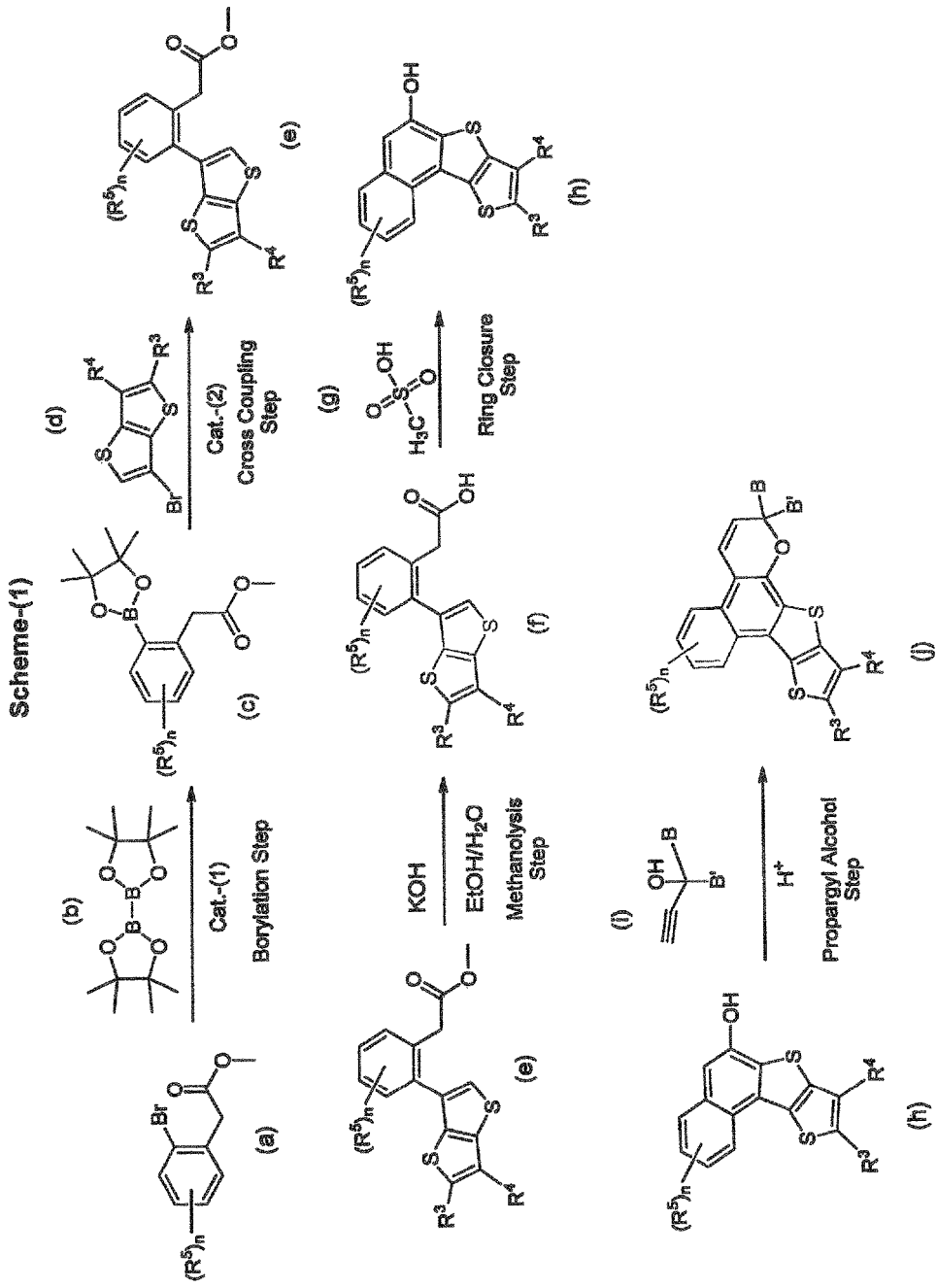
FIG. 1 is an illustrative representative general scheme, Scheme-(1), of a method for preparing photochromic compounds according to some embodiments of the present invention, such as represented by Formula (Ia-IIa) as described further herein.

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

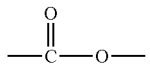

or equivalently —C(O)O—, is inclusive of the right-to-left representation thereof,

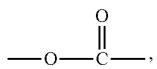

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

As used herein, the term "precursor" and related terms, such as "precursors" with regard to the various groups, for example, $R^1$, $R^2$, $R^3$, $R^4$, $R^5$, $R^6$, $R^7$, B, B', and L of the photochromic compounds and intermediates described herein, for example, the photochromic compounds represented by Formulas (Ia), (Ib), (Ia-IIa), (Ib-IIa), (Ia-IIb-1), (Ia-IIb-2), (Ib-IIb-1), (Ib-IIb-2), (Ia-IIc), (Ib-IIc), (Ia-IId), and (Ib-IId), means a group that can be converted in one or more steps to the final or desired group. For purposes of non-limiting illustration halogen groups, such as —Cl and —Br groups, can be substituted/replaced with —CN, which can be subsequently converted to —C(O)OR, —C(O)R, and —C(O)NR$_2$ groups in accordance with art-recognized methods (where each R independently is selected from hydrogen, hydrocarbyl, substituted hydrocarbyl, interrupted hydrocarbyl, and substituted interrupted hydrocarbyl groups).

As used herein, molecular weight values of polymers, such as weight average molecular weights (Mw) and number average molecular weights (Mn), are determined by gel permeation chromatography using appropriate standards, such as polystyrene standards.

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means methacrylates and/or acrylates. As used herein, the term "(meth)acrylic acid" means methacrylic acid and/or acrylic acid.

The photochromic compounds of the present invention are also referred to herein as photochromic thieno-thienyl cyclopyran compounds, photochromic thieno-thienyl fused cyclopyran compounds, and/or photochromic thieno-thienyl cyclopyrans, and/or photochromic thieno-thienyl fused cyclopyrans, where the term "cyclo" includes, with some embodiments, benzo, naphtho, anthraceno, phenanthreno, or indenobenzo.

The photochromic compounds of the present invention, as described herein, including, but not limited to, photochromic compounds represented by Formula (Ia) and Formula (Ib), in each case can optionally further include one or more coproducts, resulting from the synthesis of such compounds.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "display" means the visible or machine-readable representation of information in words, numbers, symbols, designs or drawings. Non-limiting examples of display elements include screens, monitors, and security elements, such as security marks.

As used herein the term "window" means an aperture adapted to permit the transmission of radiation therethrough. Non-limiting examples of windows include automotive and aircraft transparencies, windshields, filters, shutters, and optical switches.

As used herein the term "mirror" means a surface that specularly reflects a large fraction of incident light.

As used herein the term "liquid crystal cell" refers to a structure containing a liquid crystal material that is capable of being ordered. A non-limiting example of a liquid crystal cell element is a liquid crystal display.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," "residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, the term "Ring Position" means a particular position in the ring structure, such as the fused ring structure, of a chemical compound, such as the photochromic thieno-thienyl cyclopyran compounds of the present invention, and which are depicted herein in accordance with some embodiments by numbers within the ring structures of representative chemical formulas.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, recitations of "substituted" group, means a group, including but not limited to, alkyl group, cycloalkyl group, heterocycloalkyl group, aryl group, and/or heteroaryl group, in which at least one hydrogen thereof has been replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R_{11}'$)($R_{12}'$) where $R_{11}'$ and $R_{12}'$ are each independently selected, with some embodiments, from hydrogen, linear or branched $C_1$-$C_{20}$ alkyl, $C_3$-$C_{12}$ cycloakyl, $C_3$-$C_{12}$ heterocycloalkyl, aryl, and heteroaryl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to perhaloalkyl groups, perhaloalkenyl groups, perhaloalkynyl groups, perhaloaryl groups and perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F.

The photochromic thieno-thienyl cyclopyran compounds of the present invention, such as but not limited to those represented by Formulas (Ia) and (Ib), include groups and sub-groups that can in each case be independently selected from hydrocarbyl and/or substituted hydrocarbyl. As used herein the term "hydrocarbyl" and similar terms, such as "hydrocarbyl substituent," means: linear or branched $C_1$-$C_{25}$ alkyl (e.g., linear or branched $C_1$-$C_{10}$ alkyl); linear or branched $C_2$-$C_{25}$ alkenyl (e.g., linear or branched $C_2$-$C_{10}$ alkenyl); linear or branched $C_2$-$C_{25}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to imidazolyl, tetrahydrofuranyl, tetrahydropyranyl and piperidinyl. Representative aryl groups include but are not limited to phenyl, naphthyl, anthracynyl and triptycenyl. Representative heteroaryl groups include but are not limited to furanyl, pyranyl, pyridinyl, isoquinoline, and pyrimidinyl. Representative aralkyl groups include but are not limited to benzyl, and phenethyl.

The term "substituted hydrocarbyl" as used herein means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —N($R_{11}$')($R_{12}$') where $R_{11}$' and $R_{12}$' are each independently selected from hydrogen, hydrocarbyl and substituted hydrocarbyl.

The term "substituted hydrocarbyl" is inclusive of halohydrocarbyl (or halo substituted hydrocarbyl) substituents. The term "halohydrocarbyl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein can each be independently selected, in some instances and with some embodiments, can in each case be independently interrupted with at least one interrupting group, and when so interrupted are referred to herein as interrupted hydrocarbyl and substituted interrupted hydrocarbyl groups. Each interrupted hydrocarbyl and each substituted interrupted hydrocarbyl, are in each case independently interrupted with at least one interrupting group selected from the group consisting of —O—, —S—, —C(O)—, —C(O)O—, —OC(O)O—, —B($R_{11}$.)—, —P($R_{11}$.)—, —S(O)—, —$SO_2$—, —N=N—, —C(O)N($R_{11}$')—, —OC(O)N($R_{11}$')—, —N($R_{11}$')C(O) N$R_{11}$')—, —N($R_{11}$')— where $R_{11}$' in each case is independently selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more interrupting groups thereof. As used herein, by interrupted with at least one interrupting group selected from the group consisting of —O—, —S—, —C(O)—, —C(O)O—, —OC(O)O—, —B($R_{11}$.)—, —P($R_{11}$.)—, —P(O)($R_{11}$.)—, —S(O)—, —$SO_2$—, —N=N—, —C(O)N($R_{11}$')—, —OC(O)N($R_{11}$')—, —N($R_{11}$')C(O)N($R_{11}$')—, —N($R_{11}$')— and —Si(O$R_8$')$_w$ ($R_8$')$_t$—, means that at least one carbon of, but less than all of the carbons of, the interrupted hydrocarbyl group or substituted interrupted hydrocarbyl group, is in each case independently replaced with one or more of the recited divalent non-carbon linking groups. The interrupted hydrocarbyl and substituted interrupted hydrocarbyl groups can be interrupted with two or more of the above recited linking groups, which can be adjacent to each other or separated by one or more carbons. For purposes of non-limiting illustration, a combination of adjacent —C(O)— and —N($R_{11}$')— can provide a divalent amide linking or interrupting group, —C(O)—N($R_{11}$')—. For purposes of further non-limiting illustration, a combination of adjacent —N($R_{11}$')—, —C(O)— and —O— can provide a divalent carbamate (or urethane) linking or interrupting group, —N($R_{11}$')—C(O)—O—, where $R_{11}$' is hydrogen.

The term "interrupted with" as used with regard to the various groups described herein, such as but not limited to interrupted hydrocarbyl and substituted interrupted hydrocarbyl groups, also includes interruption at the initial linking position of the group to the compound or core compound structure with at least one interrupting group selected from the group consisting of —O—, —S—, —C(O)—, —C(O)O—, —OC(O)O—, —B($R_{11}$.)—, —P($R_{11}$.)—, —P(O)($R_{11}$.)—, —S(O)—, —$SO_2$—, —N=N—, —C(O)N($R_{11}$')—, —OC(O)N($R_{11}$')—, —N($R_{11}$')C(O)N($R_{11}$')—, —N($R_{11}$')— where $R_{11}$' in each case is independently selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more interrupting groups thereof. For purposes of nonlimiting illustration, when an $R^1$ of Formula (Ia) is interrupted hydrocarbyl, the $R^1$ interrupted hydrocarbyl group can be interrupted with one or more of the above recited divalent interrupting groups, such as but not limited to —O—: (i) along the hydrocarbyl chain thereof; and/or (ii) at the point where $R^1$ is bonded to the benzo portion of the compound represented by Formula (Ia).

The term "alkyl" as used herein, in accordance with some embodiments, means linear or branched alkyl, such as but not limited to, linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, those recited previously herein. Alkyl groups of the various compounds of the present invention can, with some embodiments, include one or more unsaturated linkages selected from —CH═CH— groups and/or one or more —C≡C— groups, provided the alkyl group is free of two or more conjugated unsaturated linkages. With some embodiments, the alkyl groups are free of unsaturated linkages, such as —CH═CH— groups and —C≡C— groups.

The term "cycloalkyl" as used herein, in accordance with some embodiments, means groups that are appropriately cyclic, such as but not limited to, $C_3$-$C_{12}$ cycloalkyl (including, but not limited to, cyclic $C_5$-$C_7$ alkyl) groups. Examples of cycloalkyl groups include, but are not limited to, those recited previously herein. The term "cycloalkyl" as used herein in accordance with some embodiments also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein, in accordance with some embodiments, means groups that are appropriately cyclic, such as but not limited to, $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, those recited previously herein. The term "heterocycloalkyl" as used herein, in accordance with some embodiments, also includes: bridged ring polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

The term "heteroaryl," as used herein, in accordance with some embodiments, includes but is not limited to $C_5$-$C_{18}$ heteroaryl, such as but not limited to $C_5$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, those recited previously herein.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl," as used herein, and in accordance with some embodiments, includes but is not limited to $C_6$-$C_{24}$ aralkyl, such as but not limited to $C_6$-$C_{10}$ aralkyl, and means an aryl group substituted with an alkyl group. Examples of aralkyl groups include, but are not limited to, those recited previously herein.

The thieno-thienyl cyclopyran compounds according to the present invention, such as, but not limited to those represented by Formulas (Ia) and (Ib), and the various groups thereof are described in further detail herein as follows.

In accordance with some embodiments, independently for each of Formula (Ia) and Formula (Ib), $R^1$ and $R^2$ together form a ring structure, and the ring structure is selected from the following Formulas (IIa), (IIb), (IIc), and (IId),

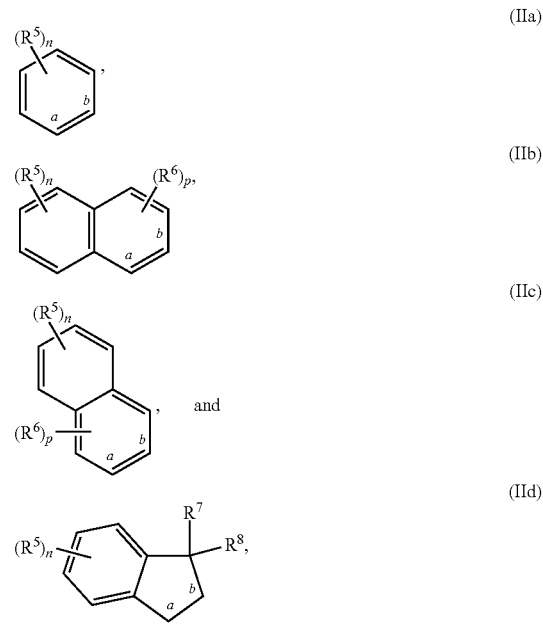

Each ring structure represented by Formulas (IIa), (IIb), (IIc), and (IId), is fused to the photochromic compound, represented by Formulas (Ia) and (Ib), at carbons a and b.

Subscript n, independently for Formulas (IIa), (IIb), (IIc), and (IId), is 1 to 4; and subscript p, independently for Formulas (IIb) and (IIc), is 1 or 2.

With further reference to (IIa), (IIb), (IIc), and (IId), $R^5$ independently for each n, and independently for Formulas (IIa), (IIb), (IIc), and (IId), and $R^6$ independently for each p, and independently for Formulas (IIb) and (IIc), are in each case independently selected from: hydrogen; hydrocarbyl; substituted hydrocarbyl; interrupted hydrocarbyl; substituted interrupted hydrocarbyl, where each interrupted hydrocarbyl and each substituted interrupted hydrocarbyl, are in each case independently interrupted with at least one interrupting group selected from the group consisting of —O—, —S—, —C(O)—, —C(O)O—, —OC(O)O—, —B($R_{11}$')—, —P($R_{11}$')—, —P(O)($R_{11}$')—, —S(O)—, —$SO_2$—, —N═N—, —C(O)N($R_{11}$')—, —OC(O)N($R_{11}$')—, —N($R_{11}$')C(O)N($R_{11}$')—, —N($R_{11}$')— where $R_{11}$' in each case is independently selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more interrupting groups thereof; halogen; cyano; and —N($R_{11}$")$R_{12}$', wherein $R_{11}$" and $R_{12}$' are each independently selected from hydrogen, hydrocarbyl or substituted hydrocarbyl, or $R_{11}$" and $R_{12}$' together form a ring structure or a ring structure including at least one heteroatom.

For Formula (IId), $R^7$ and $R^8$ are each independently selected from hydrogen; hydrocarbyl; substituted hydrocarbyl; interrupted hydrocarbyl; and substituted interrupted hydrocarbyl, where each interrupted hydrocarbyl and each substituted interrupted hydrocarbyl, are each independently interrupted with at least one interrupting group selected from the group consisting of —O—, —S—, —N($R_{11}$')—, where $R_{11}$' is selected from hydrogen, hydrocarbyl or substituted hydrocarbyl, and combinations of two or more interrupting groups thereof; or $R^7$ and $R^8$ together form a ring structure.

In accordance with some embodiments of the present invention, when $R^1$ and $R^2$, of the photochromic compound represented by Formulas (Ia) and (Ib), together form a ring structure, such as represented by Formula (IIa), the photochromic compound of the present invention can be represented by the following Formulas (Ia-IIa) and (Ib-IIa):

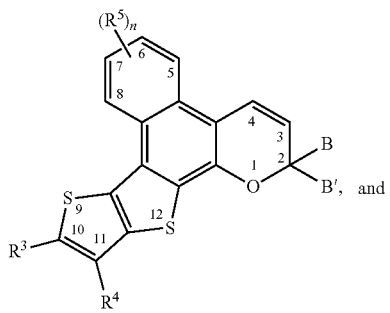
(Ia-IIa)

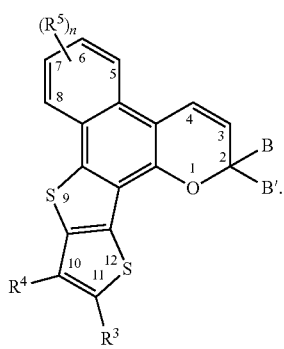
(Ib-IIa)

With reference to Formulas (Ia-IIa) and (Ib-IIa), $R^3$, $R^4$, $R^5$, n, B, and B' are each independently as defined previously and further herein.

In accordance with some further embodiments of the present invention, when $R^1$ and $R^2$, of the photochromic compound represented by Formulas (Ia) and (Ib), together form a ring structure, such as represented by Formula (IIb), the photochromic compound of the present invention can be represented by the following Formulas (Ia-IIb-1), (Ia-IIb-2), (Ib-IIb-1), and (Ib-IIb-2):

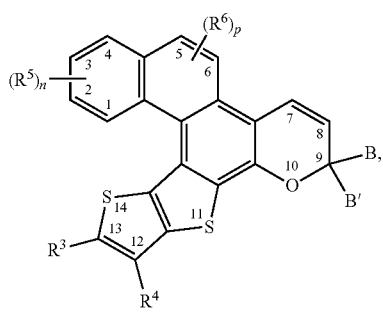
(Ia-IIb-1)

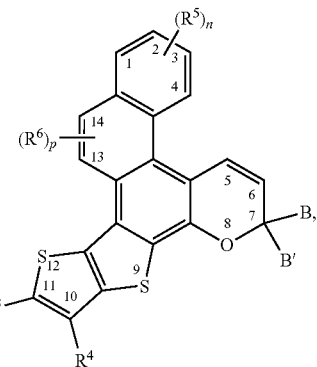
(Ia-IIb-2)

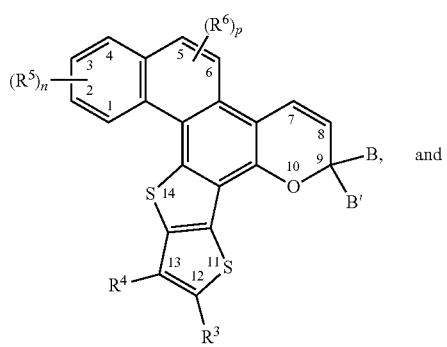
(Ib-IIb-1)
and

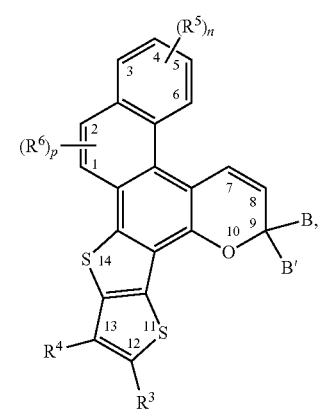
(Ib-IIb-2)

With reference to Formulas (Ia-IIb-1), (Ia-IIb-2), (Ib-IIb-1), and (Ib-IIb-2) $R^3$, $R^4$, $R^5$, $R^6$, n, p, B, and B' are each independently as defined previously and further herein.

In accordance with some additional embodiments of the present invention, when $R^1$ and $R^2$, of the photochromic compound represented by Formulas (Ia) and (Ib), together form a ring structure, such as represented by Formula (IIc), the photochromic compound of the present invention can be represented by the following Formulas (Ia-IIc) and (Ib-IIc):

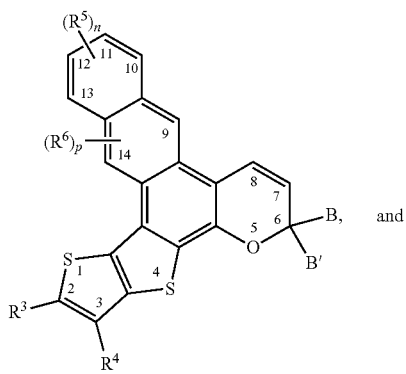
(Ia-IIc)

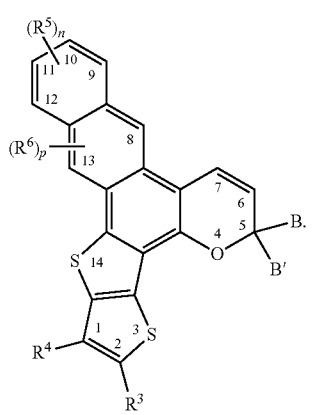
(Ib-IIc)

With reference to Formulas (Ia-IIc) and (Ib-IIc), $R^3$, $R^4$, $R^5$, $R^6$, n, p, B, and B' are each independently as defined previously and further herein.

In accordance with some further additional embodiments of the present invention, when $R^1$ and $R^2$, of the photochromic compound represented by Formulas (Ia) and (Ib), together form a ring structure, such as represented by Formula (IId), the photochromic compound of the present invention can be represented by the following Formulas (Ia-IId-1), (Ia-IId-2), (Ib-IId-1), and (Ib-IId-2):

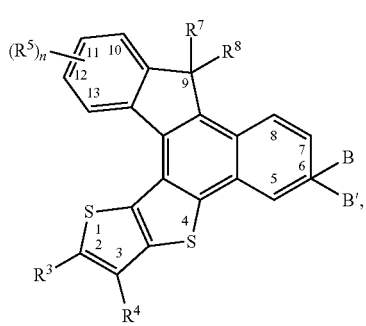
(Ia-IId-1)

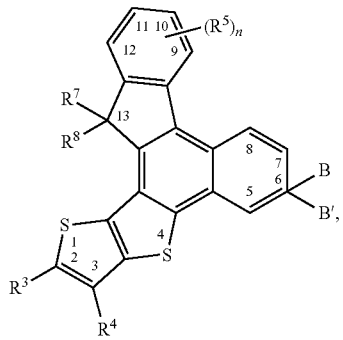
(Ia-IId-2)

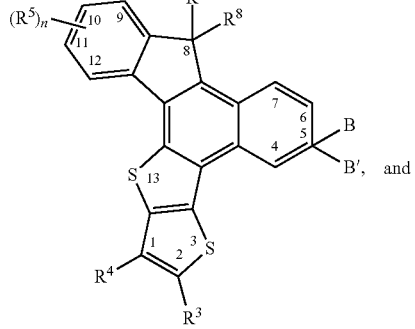
(Ib-IId-1)

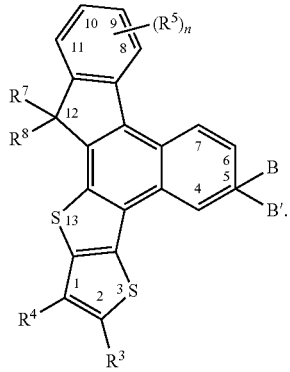
(Ib-IId-2)

With reference to Formulas (Ia-IId-1), (Ia-IId-2), (Ib-IId-1), and (Ib-IId-2), $R^3$, $R^4$, $R^5$, $R^7$, $R^8$, n, B, and B' are each independently as defined previously and further herein.

With further reference to Formulas (Ia), (Ib), (IIa), (IIb), (IIc), and (IId), and in accordance with some embodiments, $R^3$, $R^4$, $R^5$ independently for each n, and $R^6$ independently for each p, are in each case independently selected from: hydrogen; cyano; a reactive substituent; a compatibilizing substituent; halogen selected from fluoro, chloro, and bromo; $C_1$-$C_{20}$ alkyl; $C_1$-$C_{20}$ perhaloalkyl; $C_3$-$C_{10}$ cycloalkyl; substituted or unsubstituted phenyl, the phenyl substituents being selected from at least one of hydroxyl, halogen, carbonyl, $C_1$-$C_{20}$ alkoxycarbonyl, cyano, $C_1$-$C_{20}$ haloalkyl, $C_1$-$C_{20}$ alkyl, $C_1$-$C_{20}$ alkoxy, $C_1$-$C_{20}$ perhaloalkyl, and combinations thereof.

With further reference to Formulas (Ia), (Ib), (IIa), (IIb), (IIc), and (IId), and in accordance with some embodiments, $R^3$, $R^4$, $R^5$ independently for each n, and $R^6$ independently for each p, are in each case independently selected from, —O—$R_{10}$' or —C(O)—$R_{10}$' or —C(O)—O$R_{10}$', wherein $R_{10}$' is hydrogen, $C_1$-$C_{20}$ alkyl, phenyl($C_1$-$C_{20}$)alkyl, mono($C_1$-$C_{20}$)alkyl substituted phenyl($C_1$-$C_{20}$)alkyl, mono($C_1$-

$C_{20}$)alkoxy substituted phenyl($C_1$-$C_{20}$)alkyl, ($C_1$-$C_{20}$) alkoxy($C_2$-$C_{20}$)alkyl, $C_3$-$C_{10}$ cycloalkyl, or mono($C_1$-$C_{20}$) alkyl substituted $C_3$-$C_{10}$ cycloalkyl.

With additional reference to Formulas (Ia), (Ib), (IIa), (IIb), (IIc), and (IId), and in accordance with some embodiments, $R^3$, $R^4$, $R^5$ independently for each n, and $R^6$ independently for each p, are in each case independently selected from, —N($R_{11}$')$R_{12}$', wherein $R_{11}$' and $R_{12}$' are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{20}$ cycloalkyl, $C_4$-$C_{20}$ bicycloalkyl, $C_5$-$C_{20}$ tricycloalkyl or $C_3$-$C_{20}$ alkoxyalkyl, wherein said aryl group is phenyl or naphthyl, or $R_{11}$' and $R_{12}$' come together with the nitrogen atom to form a ring. With some embodiments, $R_{11}$' and $R_{12}$', of —N($R_{11}$')$R_{12}$', come together with the nitrogen atom to form a ring selected from a $C_3$-$C_{20}$ hetero-bicycloalkyl ring or a $C_4$-$C_{20}$ hetero-tricycloalkyl ring.

With further additional reference to Formulas (Ia), (Ib), (IIa), (IIb), (IIc), and (IId), and in accordance with some embodiments, $R^3$, $R^4$, $R^5$ independently for each n, and $R^6$ independently for each p, are in each case independently selected from, a nitrogen containing ring represented by the following graphic formula XIIA,

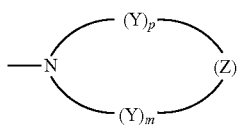

XIIA

With reference to Formula XIIA, each —Y— is independently chosen for each occurrence from —CH$_2$—, —CH($R_{13}$')—, —C($R_{13}$')$_2$—, —CH(aryl)-, —C(aryl)$_2$-, and —C($R_{13}$')(aryl)-, and Z is —Y—, —O—, —S—, —S(O)—, —SO$_2$—, —NH—, —N($R_{13}$')—, or —N(aryl)-, wherein each $R_{13}$' is independently $C_1$-$C_{20}$ alkyl, each aryl is independently phenyl or naphthyl, m is an integer 1, 2 or 3, and p is an integer 0, 1, 2, or 3 and provided that when p is 0, Z is —Y—.

In accordance with some embodiments and with further reference to Formulas (Ia), (Ib), (IIa), (IIb), (IIc), and (IId), $R^3$, $R^4$, $R^5$ independently for each n, and $R^6$ independently for each p, are in each case independently selected from, a group represented by one of the following graphic formulas XIIB or XIIC,

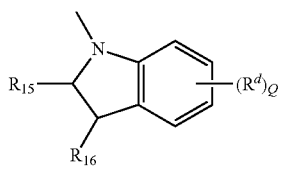

XIIB

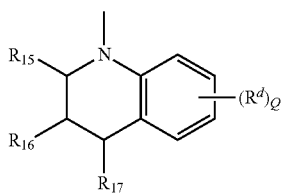

XIIC

Independently for each of Formulas XIIB and XIIC, $R_{15}$, $R_{16}$, and $R_{17}$ are each independently hydrogen, $C_1$-$C_6$ alkyl, phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl, $C_1$-$C_{20}$ alkoxy, fluoro or chloro, and Q is an integer 0, 1, 2, or 3.

In accordance with some further embodiments and with further reference to Formulas (Ia), (Ib), (IIa), (IIb), (IIc), and (IId), $R^3$, $R^4$, $R^5$ independently for each n, and $R^6$ independently for each p, are in each case independently selected from, unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_{20}$ alkyl, $C_1$-$C_{20}$ alkoxy, or phenyl ($C_1$-$C_{20}$)alkyl.

In accordance with some additional embodiments and with further reference to Formulas (Ia), (Ib), (IIa), (IIb), (IIc), and (IId), two adjacent $R^5$ groups together form a group represented by the following Formulas XIID or XIIE:

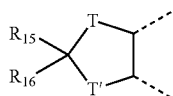

XIID

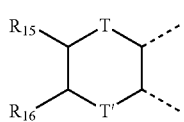

XIIE

With reference to Formulas XIID and XIIE, T and T' are each independently oxygen or the group —NR$_{11}$'—, where $R_{11}$', $R_{15}$, and $R_{16}$ are as set forth above.

In accordance with some additional embodiments and with further reference to Formulas (Ia), (Ib), (IIa), (IIb), (IIc), and (IId), $R^3$ and $R^4$ together form a cyclic ring structure selected from cycloalkyl, fused ring cycloalkyl, aryl, fused ring aryl, and fused ring cycloalkyl-aryl.

With further reference to Formulas (Ia), (Ib), and (IId), and in accordance with some embodiments, $R^7$ and $R^8$ are each independently selected from: (i) hydrogen, hydroxyl, $C_1$-$C_{20}$ alkyl, $C_1$-$C_{20}$ haloalkyl, $C_3$-$C_{10}$ cycloalkyl, allyl, benzyl, or substituted benzyl, said benzyl substituents being chosen from halogen, $C_1$-$C_{20}$ alkyl or $C_1$-$C_{20}$ alkoxy; and (ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in each case being independently chosen from halogen, $C_1$-$C_{20}$ alkyl or $C_1$-$C_{20}$ alkoxy; or (iii) $R^7$ and $R^8$ together form a spiro substituent selected from a substituted or unsubstituted spiro-carbocyclic ring containing 3 to 10 carbon atoms, a substituted or unsubstituted spiro-heterocyclic ring containing 1 or 2 oxygen atoms and 3 to 10 carbon atoms including the spirocarbon atom, said spirocarbocyclic ring and spiro-heterocyclic ring being annellated with 0, 1 or 2 benzene rings, said substituents being hydrogen or $C_1$-$C_{20}$ alkyl.

With reference to Formulas (Ia) and (Ib), B and B' are in each case independently selected from: an aryl group that is mono-substituted with a reactive substituent or a compatibilizing substituent; a substituted phenyl; a substituted aryl; a substituted 9-julolindinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolindinyl, or heteroaromatic substituent is a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl. With some further embodiments, each of the phenyl, aryl and heteroaromatic substituents are each independently: hydroxyl, a group —C(=O)$R_{21}$, wherein $R_{21}$ is —O$R_{22}$, —N($R_{23}$)$R_{24}$, piperidino, or morpholino, wherein $R_{22}$ is allyl, $C_1$-$C_{20}$ alkyl, phenyl, mono($C_1$-$C_{20}$)alkyl substituted phenyl, mono($C_1$-$C_{20}$)alkoxy substituted phenyl, phenyl ($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$) alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and said halo substituent is chloro or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_3$-$C_{10}$ cycloalkylaryl, $C_3$-$C_{10}$ cycloalkyl, $C_3$-$C_{10}$ cycloalkyloxy, $C_3$-$C_{10}$ cycloalkyloxy ($C_1$-$C_{20}$)alkyl, $C_3$-$C_{10}$ cycloalkyloxy($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di($C_1$-$C_{20}$)alkylaryl($C_1$-$C_{20}$)alkyl, mono- or di-($C_1$-$C_{20}$)alkoxyaryl($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$)alkoxy, amino, mono- or di-($C_1$-$C_{20}$)alkylamino, diarylamino, piperazino, N—($C_1$-$C_{20}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen.

In accordance with some further embodiments, B and B' of the photochromic compounds of the present invention, are each independently an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, each of said substituents being $C_1$-$C_{20}$ alkyl, $C_1$-$C_{20}$ alkoxy, phenyl, or halogen.

In accordance with some additional embodiments, B and B' of the photochromic compounds of the present invention, are each independently a group represented by one the following Formulas (XIVA) or (XIVB):

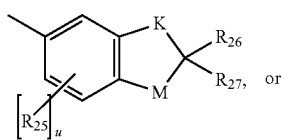

(XIVA)

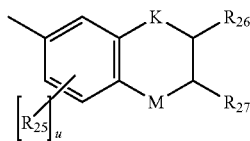

(XIVB)

Independently for Formulas (XIVA) and (XIVB), K is —CH$_2$— or —O—, and M is —O— or substituted nitrogen, provided that when M is substituted nitrogen, K is —CH$_2$—, the substituted nitrogen substituents being hydrogen, $C_1$-$C_{20}$ alkyl, or $C_1$-$C_{20}$ acyl, each $R_{25}$ being independently chosen for each occurrence from $C_1$-$C_{20}$ alkyl, $C_1$-$C_{20}$ alkoxy, hydroxy, and halogen, $R_{26}$ and $R_{27}$ each being independently hydrogen or $C_1$-$C_{20}$ alkyl, and u is an integer ranging from 0 to 2.

With some embodiments, B and B' of the photochromic compounds of the present invention, are each independently a group represented by the following Formula (XV):

(XV)

With reference to Formula (XV), $R_{28}$ is hydrogen or $C_1$-$C_{20}$ alkyl, and $R_{29}$ is an unsubstituted, mono-, or di-substituted group chosen from naphthyl, phenyl, furanyl, and thienyl, wherein the substituents are $C_1$-$C_{20}$ alkyl, $C_1$-$C_{20}$ alkoxy, or halogen.

With some alternative embodiments, B and B' of the photochromic compounds of the present invention, taken together form one of a fluoren-9-ylidene, mono-, or di-substituted fluoren-9-ylidene, each of said fluoren-9-ylidene substituents being independently chosen from $C_1$-$C_{20}$ alkyl, $C_1$-$C_{20}$ alkoxy, and halogen.

In accordance with some embodiments and with further reference to Formulas (Ia), (Ib), (IIa), (IIb), (IIc), and (IId), $R^3$, $R^4$, $R^5$ independently for each n, and $R^6$ independently for each p, are in each case independently selected from: hydrogen; cyano; $C_1$-$C_6$ alkyl; $C_3$-$C_7$ cycloalkyl; $C_1$-$C_8$ perhaloalkyl; fluoro; chloro; bromo, —O—$R_{10}$'; and substituted or unsubstituted phenyl, the phenyl substituents being selected from at least one of hydroxyl, halogen, $C_1$-$C_6$ alkoxycarbonyl, cyano, $C_1$-$C_6$ haloalkyl, $C_1$-$C_6$ alkyl, $C_1$-$C_6$ alkoxy, and $C_1$-$C_6$ perhaloalkyl.

With reference to Formulas (Ia), (Ib), (IIa), (IIb), (IIc), and (IId), and in accordance with some embodiments, $R^7$ and $R^8$ are each independently selected from hydrogen, $C_1$-$C_8$ alkyl, $C_1$-$C_8$ haloalkyl, and $C_3$-$C_7$, cycloalkyl, or $R^7$ and $R^8$ together form a spiro substituent selected from a substituted or unsubstituted spiro-carbocyclic ring containing 3 to 10 carbon atoms.

With further reference to Formulas (Ia) and (Ib), and in accordance with some embodiments, B and B' are in each case independently selected from: unsubstituted aryl; aryl substituted with $C_1$-$C_6$ alkoxy; aryl substituted with $C_1$-$C_6$ perhaloalkyl; aryl substituted with morpholino; and aryl substituted with piperidino.

With reference to Formulas (Ia), (Ib), (IIa), (IIb), (IIc), and (IId), and in accordance with some embodiments, one of, $R^3$ is, $R^4$ is, $R^5$ is, $R^6$ is, B is substituted with, and/or B' is substituted with, in each case independently, a group L represented by the following Formula (III), $[S_1]_c$-$[Q_1$-$[S_2]_d]_{d'}$-$[Q_2$-$[S_3]_e]_{e'}$-$[Q_3$-$[S_4]_f]_{f'}$—$S_5$—P  Formula (III)

With reference to Formula (III), and in accordance with some embodiments, $Q_1$, $Q_2$, and $Q_3$ for each occurrence, are independently selected from a divalent group selected from optionally substituted aryl, optionally substituted heteroaryl, optionally substituted cycloalkyl, and optionally substituted heterocycloalkyl. The aryl substituents, heteroaryl substituents, cycloalkyl substituents, and heterocycloalkyl substituents are each independently selected from P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl. The straight-chain $C_1$-$C_{18}$ alkyl and branched $C_1$-$C_{18}$ alkyl are mono-substituted with a group selected from cyano, halogen, and $C_1$-$C_{18}$ alkoxy. Alternatively, and with some embodiments, the straight-chain $C_1$-$C_{18}$ alkyl and branched $C_1$-$C_{18}$ alkyl are poly-substituted with at least two groups independently selected from halogen, -M(T)$_{(v-1)}$ and -M(OT)$_{(v-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M.

With further reference to Formula (III), and in accordance with some further embodiments, (b) c, d, e, and f are each independently chosen from an integer of 1 to 20; and each $S_1$, $S_2$, $S_3$, $S_4$, and $S_5$ is independently chosen for each occurrence from a spacer unit selected from (i), (ii), and (iii) as described as follows. With some embodiments, each $S_1$, $S_2$, $S_3$, $S_4$, and $S_5$ is independently chosen for each occurrence from a spacer unit selected from (i) optionally substituted alkylene, optionally substituted haloalkylene, —Si(CH$_2$)$_g$—, and —(Si[(CH$_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from $C_1$-$C_{18}$ alkyl, $C_3$-$C_{10}$ cycloalkyl and aryl. With some further embodiments, each $S_1$, $S_2$, $S_3$, $S_4$, and $S_5$ is independently chosen for each occurrence from a spacer unit selected from (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_{15}$ alkyl, $C_3$-$C_{10}$ cycloalkyl and aryl, and Z' for each occurrence is independently selected from $C_1$-$C_{18}$ alkyl, $C_3$-$C_{10}$ cycloalkyl and aryl. With some additional embodiments, each $S_1$, $S_2$, $S_3$, $S_4$, and $S_5$ is independently chosen for each occurrence from a spacer unit selected from (iii) —O—, —C(=O)—, —N=N—, —S—, —S(=O)—, —(O=)S(=O)—, —(O=)S(=O)O—, —O(O=)S(=O)O— and straight-chain or branched $C_1$-$C_{24}$ alkylene residue, said $C_1$-$C_{24}$ alkylene residue being unsubstituted, mono-substituted by cyano or halogen, or poly-substituted by halogen. With further reference to each of $S_1$, $S_2$, $S_3$, $S_4$, and $S_5$, and with some embodiments, there is the proviso that when two spacer units comprising heteroatoms are linked together the spacer units are linked so that heteroatoms are not directly linked to each other, and the bond between $S_5$ and P is free of two heteroatoms linked to each other.

With further reference to Formula (III), and in accordance with some further embodiments, (c) P for each occurrence is independently selected from hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylene, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound.

With additional reference to Formula (III), and in accordance with some further embodiments, (d) d', e' and f' are each independently chosen from 0, 1, 2, 3, and 4, provided that the sum of d'+e'+f' is at least 1.

Independently for each group L represented by Formula (III), and in accordance with some embodiments, (a) $Q_1$, $Q_2$, and $Q_3$ for each occurrence, are independently selected from optionally substituted aryl and optionally substituted cycloalkyl.

In accordance with some further embodiments, and independently for each group L represented by Formula (III), (b) each $S_1$, $S_2$, $S_3$, $S_4$, and $S_5$ is independently chosen for each occurrence from a spacer unit selected from (ii) or (iii) as described as follows. Each $S_1$, $S_2$, $S_3$, $S_4$, and $S_5$ of Formula (III), with some embodiments, is independently chosen for each occurrence from a spacer unit selected from (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl. Each $S_1$, $S_2$, $S_3$, $S_4$, and $S_5$ of Formula (III), with some further embodiments, is independently chosen for each occurrence from a spacer unit selected from (iii) —O—, —C(=O)—, —C≡C—, —N=N—, —S—, —S(=O)—, and straight-chain or branched $C_1$-$C_{12}$ alkylene residue, said $C_1$-$C_{12}$ alkylene residue being unsubstituted, mono-substituted by cyano or halogen, or poly-substituted by halogen.

In accordance with some additional embodiments, independently for each group L represented by Formula (III), (c) P for each occurrence is independently selected from hydrogen, hydroxy, amino, $C_2$-$C_8$ alkenyl, $C_2$-$C_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, $C_1$-$C_8$ alkyl aminocarbonyl, aminocarbonyl($C_1$-$C_8$)alkyl, $C_1$-$C_8$ alkyloxycarbonyloxy, halocarbonyl, aryl, hydroxy($C_1$-$C_8$)alkyl, $C_1$-$C_8$ alkyl, $C_1$-$C_8$ alkoxy, amino($C_1$-$C_8$)alkyl, $C_1$-$C_8$ alkylamino, di-($C_1$-$C_8$)alkylamino, $C_1$-$C_8$ alkyl($C_1$-$C_8$)alkoxy, $C_1$-$C_8$ alkoxy($C_1$-$C_8$)alkoxy, nitro, poly($C_1$-$C_8$)alkyl ether, ($C_1$-$C_8$)alkyl($C_1$-$C_8$)alkoxy($C_1$-$C_8$)

alkyl, polyethyleneoxy, polypropyleneoxy, ethylene, acryloyl, acryloyloxy($C_1$-$C_8$)alkyl, methacryloyl, methacryloyloxy($C_1$-$C_8$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, and vinyl ester.

In accordance with some further additional embodiments, independently for each group L represented by Formula (III), (b) each $S_1$, $S_2$, $S_3$, $S_4$, and $S_5$ is independently chosen for each occurrence from a spacer unit selected from: (ii) —N(Z)—, —C(Z)=C(Z)—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl; and (iii) —O—, —C(=O)—, —C≡C—, and straight-chain or branched $C_1$-$C_6$ alkylene residue, said $C_1$-$C_6$ alkylene residue being unsubstituted, mono-substituted by cyano or halogen, or poly-substituted by halogen.

In accordance with some additional further embodiments, independently for each group L represented by Formula (III), (c) P for each occurrence is independently selected from hydrogen, hydroxy, amino, $C_2$-$C_8$ alkenyl, $C_2$-$C_8$ alkynyl, and aryl.

Each group L represented by Formula (III) is, with some embodiments, independently selected from the following non-limiting groups L(1) through L-DC-(I):

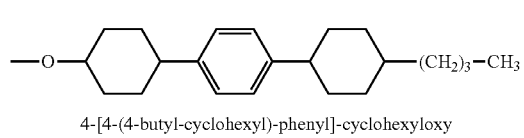

L(1)

4-[4-(4-butyl-cyclohexyl)-phenyl]-cyclohexyloxy

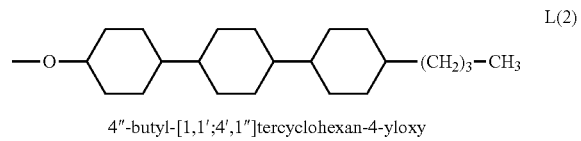

L(2)

4″-butyl-[1,1′;4′,1″]tercyclohexan-4-yloxy

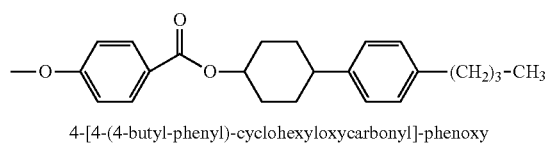

L(3)

4-[4-(4-butyl-phenyl)-cyclohexyloxycarbonyl]-phenoxy

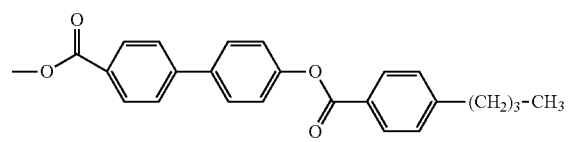

L(4)

4′-(4-butyl-benzoyloxy)-biphenyl-4-carbonyloxy

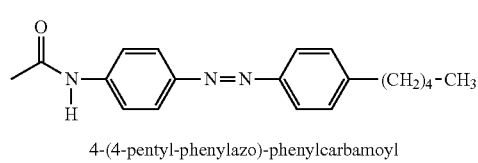

L(5)

4-(4-pentyl-phenylazo)-phenylcarbamoyl

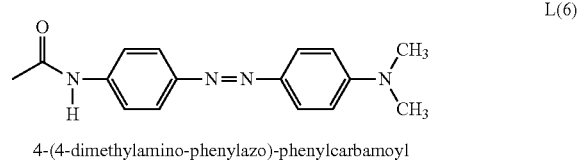

L(6)

4-(4-dimethylamino-phenylazo)-phenylcarbamoyl

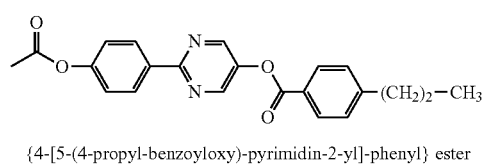

L(7)

{4-[5-(4-propyl-benzoyloxy)-pyrimidin-2-yl]-phenyl} ester

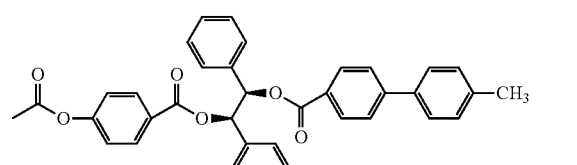

L(8)

{4-[2-(4′-methyl-biphenyl-4-carbonyloxy)-1,2-diphenyl-ethoxycarbonyl]-phenyl} ester

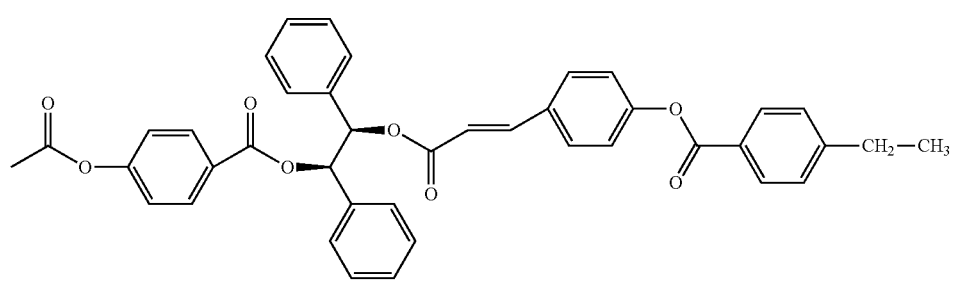

L(9)

[4-(1,2-diphenyl-2-{3-[4-(4-propyl-benzoyloxy)-phenyl]-acryloyloxy}-ethoxycarbonyl)-phenyl] ester -continued

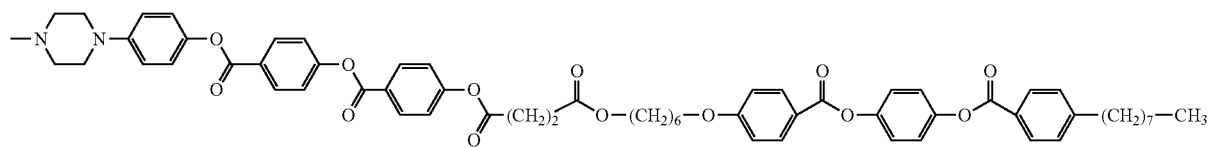

4-[4-(4-{4-[3-(6-{4-[4-(4-nonyl-benzoyloxy)-phenoxycarbonyl]-phenoxy}-hexyloxycarbonyl)-propionyloxy]-benzoyloxy}-benzoyloxy)-phenyl]-piperazin-1-yl

L(10)

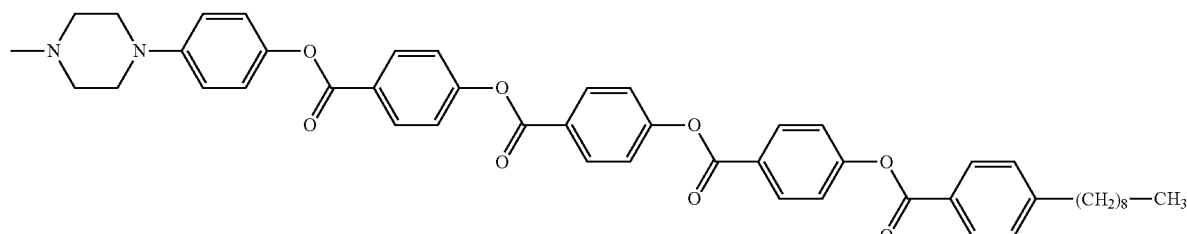

{4-[4-(4-{4-[4-(4-nonyl-benzoyloxy)-benzoyloxy]-benzoyloxy}-benzoyloxy)-phenyl]-piperazin-1-yl}

L(11)

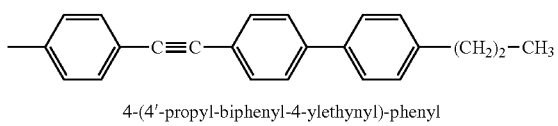

4-(4′-propyl-biphenyl-4-ylethynyl)-phenyl

L(12)

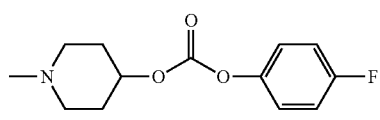

4-(4-fluoro-phenoxycarbonyloxy)-piperidin-1-yl

L(13)

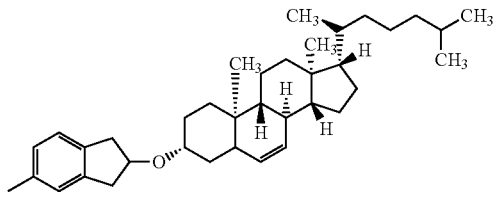

2-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-indan-5-yl

L(14)

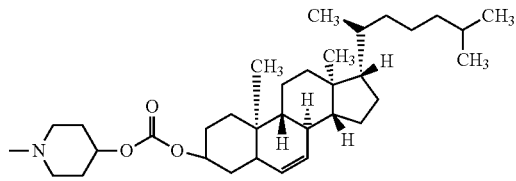

4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl

L(15)

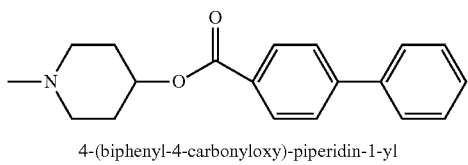

4-(biphenyl-4-carbonyloxy)-piperidin-1-yl

L(16)

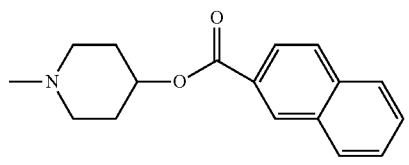

4-(naphthalene-2-carbonyloxy)-piperidin-1-yl

L(17)

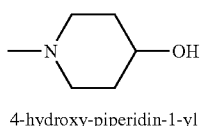

4-hydroxy-piperidin-1-yl

L(18)

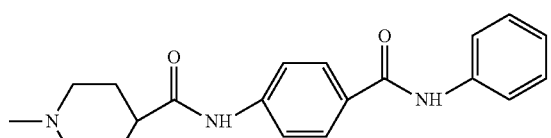

4-(4-phenylcarbamoyl-phenylcarbamoyl)-piperidin-1-yl

L(19)

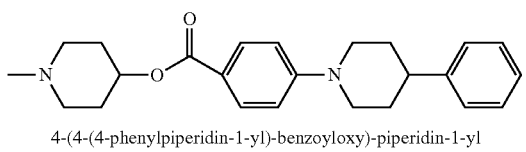

4-(4-(4-phenylpiperidin-1-yl)-benzoyloxy)-piperidin-1-yl

L(20)

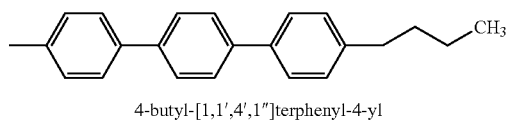

4-butyl-[1,1′,4′,1″]terphenyl-4-yl

L(21)

-continued

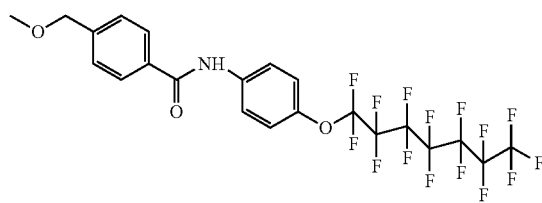

4-4(pentadecafluoroheptyloxy-phenylcarbamoyl)-benzyloxy
L(22)

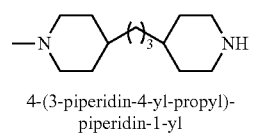

4-(3-piperidin-4-yl-propyl)-piperidin-1-yl
L(23)

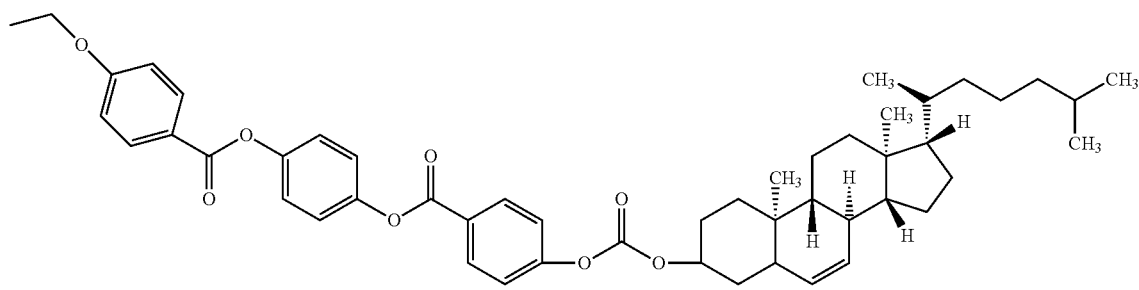

4-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-benzoyloxy}-phenoxycarbonyl)-phenoxymethyl
L(24)

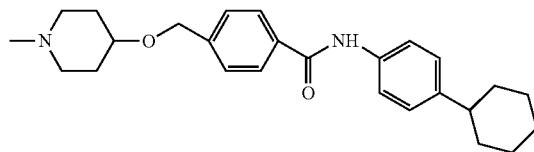

4-[4-(4-cyclohexyl-phenylcarbamoyl)-benzyloxy]-piperidin-1-yl
L(25)

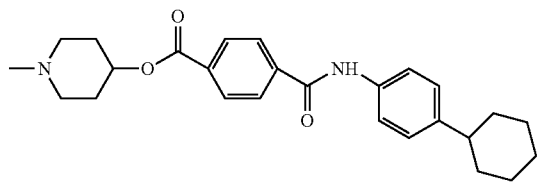

4-[4-(4-cyclohexyl-phenylcarbamoyl)-benzyloxy]-piperidin-1-yl
L(26)

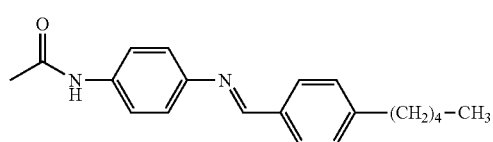

N-{4-[(4-pentyl-benzylidene)-amino]-phenyl}-acetamidyl
L(27)

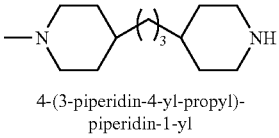

4-(3-piperidin-4-yl-propyl)-piperidin-1-yl
L(28)

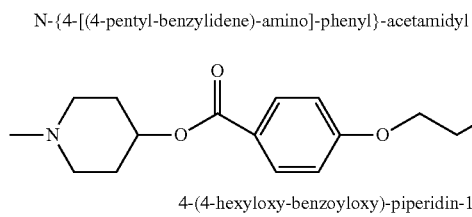

4-(4-hexyloxy-benzoyloxy)-piperidin-1-yl]
L(29)

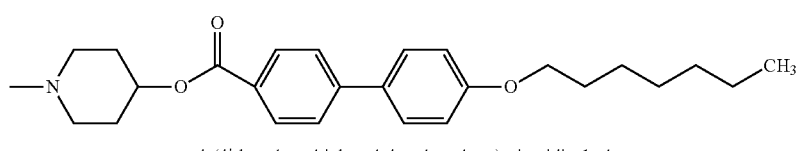

4-(4'-hexyloxy-biphenyl-4-carbonyloxy)-piperidin-1-yl
L(30)

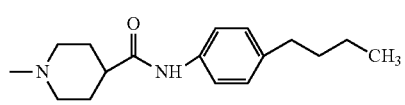

4-(4-butyl-phenylcarbamoyl)-piperidin-1-yl
L(31)

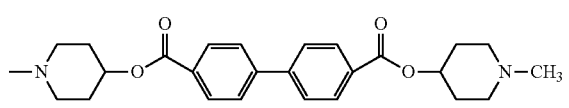

1-methyl-4-((4'-(((1-methylpiperidin-4-yl)oxy)carbonyl)-[1,1'-biphenyl]-4-carbonyl)oxy)piperidin-1-yl
L(32a)

-continued

L(32b)

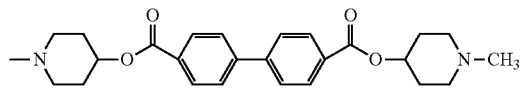

bis(1-yl-piperidin-4-yl) [1,1'-biphenyl]-4,4'-dicarboxylate

L(33)

4-(4-(9-(4-butylphenyl)-2,4,8,10-tetraoxaspiro[5.5]undec-3-yl)phenyl)piperazin-1-yl

L(34)

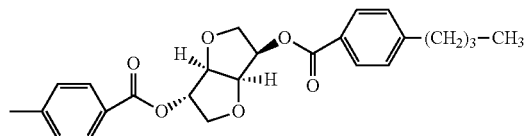

4-(6-(4-butylphenyl)carbonyloxy-(4,8-dioxabicyclo[3.3.0]oct-2-yl))oxycarbonyl)pheny

L(35)

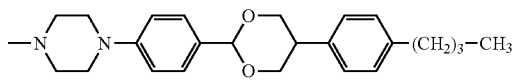

1-{4-[5-(4-butyl-phenyl)-[1,3]dioxan-2-yl]-phenyl}-4-methyl-piperazin-1-yl

L(36)

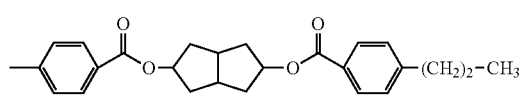

4-(7-(4-propylphenylcarbonyloxy)bicyclo[3.3.0]oct-2-yl)oxycarbonyl)phenyl

L(37)

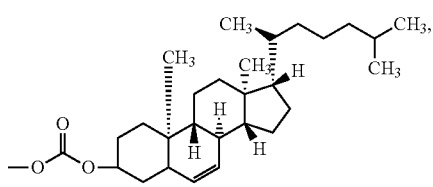

4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy L(a)

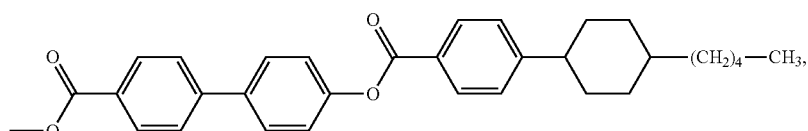

L(b)

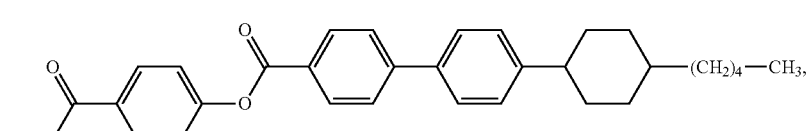

L(c)

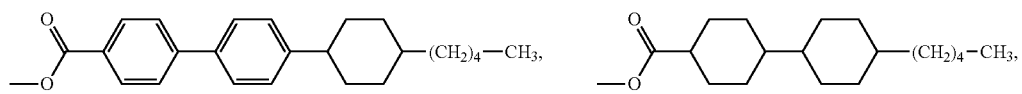

L(d)

L(e)

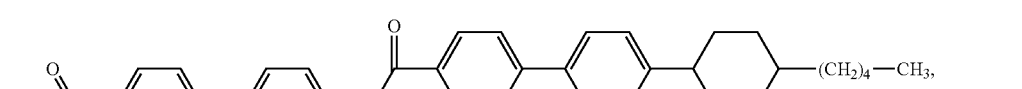

L(f)

L(g)

L(h)

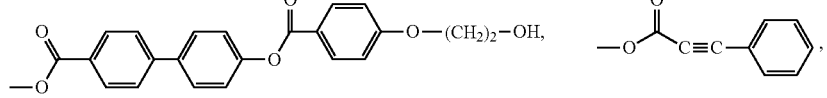

L(i)

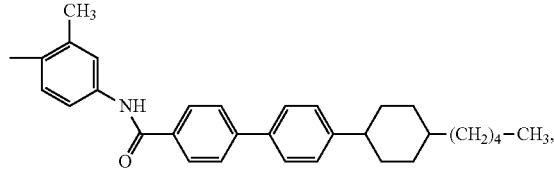

-continued
L(j)
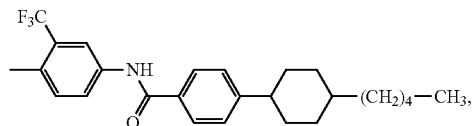
L(k)
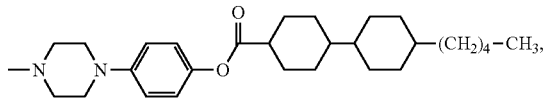
L(l)
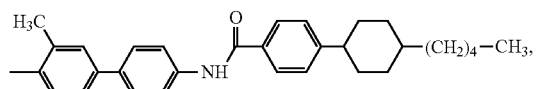
L(m)
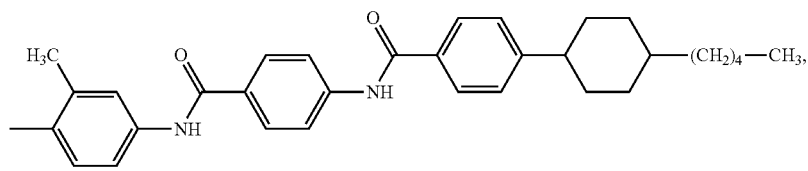
L(n)
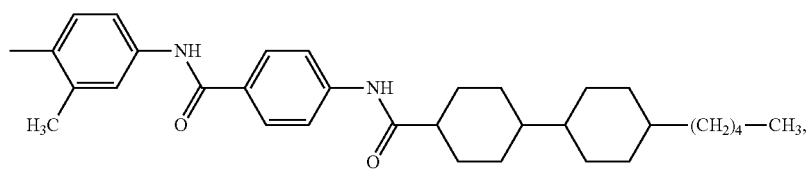
L(o)
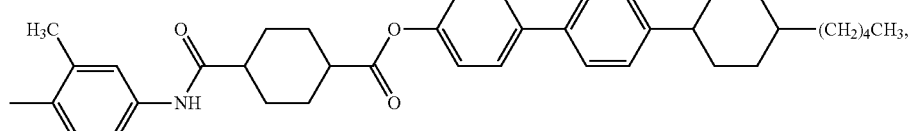
L(p)
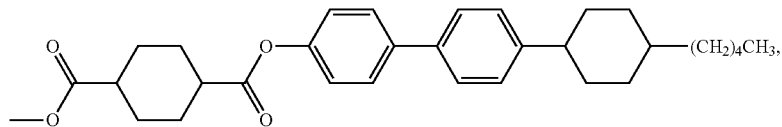
L(q)
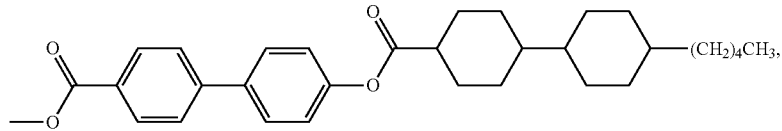
L(r)
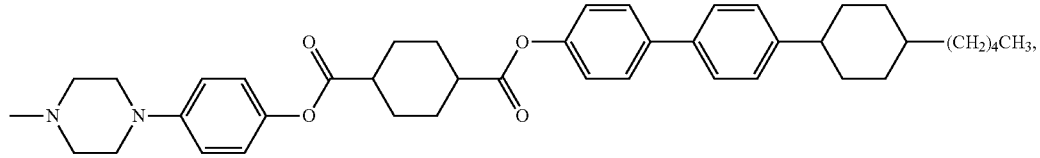
L(s)
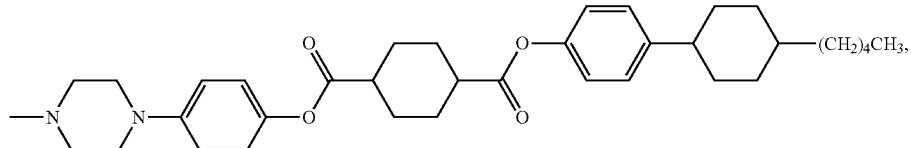
L(t)
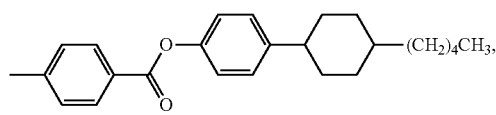
L(u)
L(v)
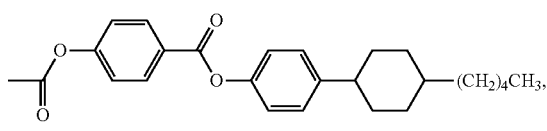

-continued

L(w): [structure]

L(x): [structure]

L(y): [structure]

L(z): [structure]

L(aa): [structure]

L(ab): [structure]

L(ac): [structure]

L(ad): [structure]

L(ae): [structure]

L(af): [structure]

L-DC-(a)
(4-trans-(4-pentylcyclohexyl)benzamido)phenyl,

L-DC-(b)
(4-(4-trans-(4-pentylcyclohexyl)phenoxy)carbonyl) phenyl,

L-DC-(c)
4-(4-(4-trans-(4-pentylcyclohexyl)phenyl)benzamido) phenyl,

L-DC-(d)
4-((trans-(4'-pentyl-[1,1'-bi(cyclohexan)]-4-yl)oxy)carbonyl)phenyl,

L-DC-(e)
4-(4'-(4-pentylcyclohexyl)-[1,1'-biphenyl]-4-ylcarboxamido)phenyl,

L-DC-(f)
4-((4'-(4-pentylcyclohexyl)-[1,1'-biphenyl]-4-carbonyl)oxy)benzamido,

L-DC-(g)
4-(4'-(4-pentylcyclohexyl)-[1,1'-biphenyl]-, 4-carbonyl)piperazin-1-yl

L-DC-(h)
4-(4-(4-trans-(4-pentylcyclohexyl) phenyl)benzamido)-2-(trifluoromethyl)phenyl, L-DC-(i)
2-methyl-4-trans-(4-((4¢-trans-(4-pentylcyclohexyl)biphenyl-4-,yloxy)carbonyl)cyclohexanecarboxamido)phenyl L-DC-(j)
4'-(4'-pentylbi(cyclohexane-4-)carbonyloxy)biphenylcarbonyloxy, L-DC-(k)
4-(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy), and carbonyl)piperazin-1-yl L-DC-(l)
4-((S)-2-methylbutoxy)phenyl)-10-(4-(((3R,3aS,6S,6aS)-6-(4'-trans-(4-pentylcyclohexyl)biphenylcarbonyloxy)hexahydrofuro[3,2-b]furan-3-yloxy)carbonyl)phenyl In accordance with some embodiments, the photochromic compounds of the present invention, such as represented by Formulas (Ia) and/or (Ib), after formation thereof, can be subjected to one or more additional chemical reactions for purposes of modifying at least one of $R^3$, $R^4$, $R^5$, $R^6$, B, and/or B' so as to be converted to or to be substituted with an L group (or group L) as described previously herein with reference to Formula (III). Examples of additional chemical reactions that the photochromic compound(s) represented by Formula (Ia) and/or Formula (Ib) can be subjected to include, but are not limited to, palladium-catalyzed cross couplings, etherifications, esterifications, amidations, and condensations.

Non-limiting examples of photochromic compounds according to the present invention, based on Formula (Ia), include those represented by the following Formulas (Ia-IIa-1) through (Ia-IIa-5), Formulas (Ia-1) through (Ia-3), Formula (Ia-IIb-1-A), and related chemical names:

(Ia-IIa-1)

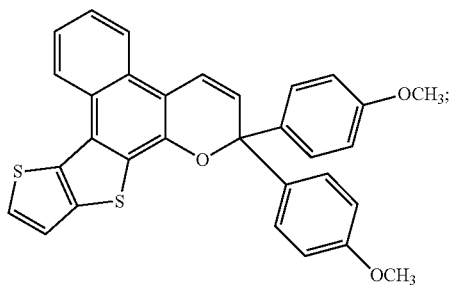

2,2-bis(4-methoxyphenyl)-2H-benzo[f]thieno
[2',3':4,5]thieno[3,2-h]chromene (Ia-IIa-2)

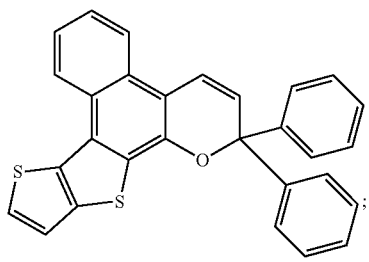

2,2-diphenyl-2H-benzo[f]thieno
[2',3':4,5]thieno[3,2-h]chromene (Ia-IIa-3)

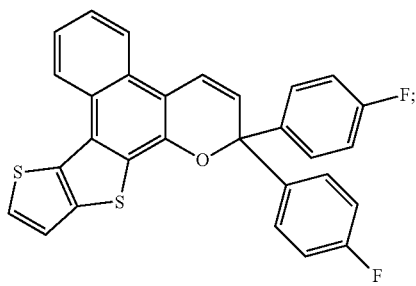

2,2-bis(4-fluorophenyl)-2H-benzo[f]thieno
[2',3':4,5]thieno[3,2-h]chromene (Ia-IIa-4)

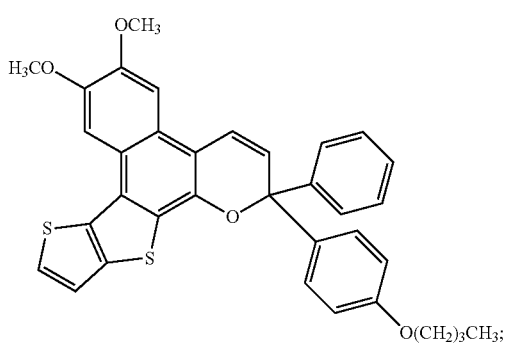

2-(4-butoxyphenyl)-6,7-dimethoxy-2-phenyl-2H-
benzo[f]thieno[2',3':4,5]thieno[3,2-h]chromene (Ia-IIa-5)

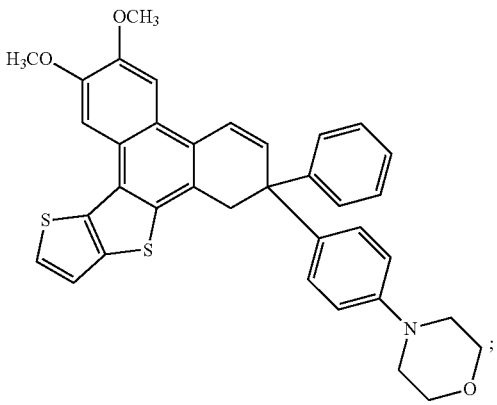

4-(4-(6,7-dimethoxy-2-phenyl-2H-benzo[f]thieno[2',3':4,5]
thieno[3,2-h]chromen-2-yl)phenyl)morpholine (Ia-1)

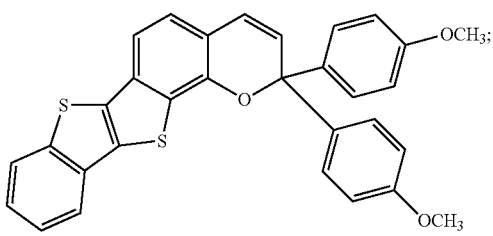

2,2-bis(4-methoxyphenyl)-2H-benzo[4',5']thieno[2',3':4,5]
thieno[3,2-h]chromene (Ia-2)

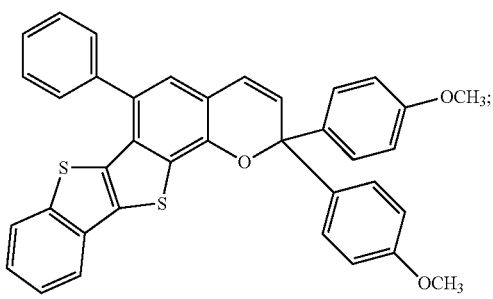

2,2-bis(4-methoxyphenyl)-6-phenyl-
2H-benzo[4',5']thieno[2',3':4,5]
thieno[3,2-h]chromene (Ia-3)

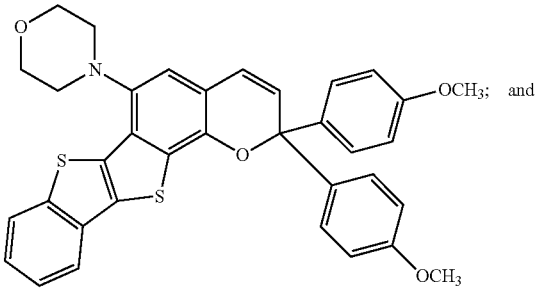

4-(2,2-bis(4-methoxyphenyl)-2H-benzo[4',5']thieno
[2',3':4,5]thieno[3,2-h]chromen-6-yl)morpholine

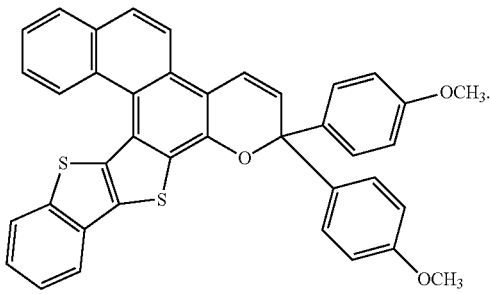

9,9-bis(4-methoxyphenyl)-9H-benzo[4',5']thieno
[2',3':4,5]naphtho[3,2-h]naphtho[2,1-f]chromene Additional non-limiting examples of photochromic compounds according to the present invention are described in further detail herein in the Examples.

The present invention also provides a photochromic compound represented by the following Formula (IV), $$L^1\text{-}(PC)_{n'} \qquad \text{Formula (IV)}$$

With reference to Formula (IV), n' is at least 2, such as from 2 to 100, or from 2 to 50, or from 2 to 25, or from 2 to 20, or from 2 to 15, or from 2 to 10, or from 2 to 8, or from 2 to 5.

With further reference to Formula (IV), the PC group or moiety, independently for each n', is a residue of a photochromic compound according to the present invention, such as represented by Formula (Ia) and/or Formula (Ib), and as described previously herein.

With additional reference to Formula (IV), $L^1$ is a multivalent linking group selected from: a multivalent polymer; a multivalent hydrocarbyl group; a multivalent substituted hydrocarbyl group; a multivalent interrupted hydrocarbyl group; and a multivalent substituted interrupted hydrocarbyl group. Each multivalent interrupted hydrocarbyl group and each multivalent substituted interrupted hydrocarbyl group, are each independently interrupted with at least one interrupting group selected from the group consisting of —O—, —S—, —C(O)—, —C(O)O—, —OC(O)O—, —B(R$_{11}$')—, —P(O)(R$_{11}$')—, —S(O)—, —SO$_2$—, —N=N—, —C(O)N(R$_{11}$')—, —OC(O)N(R$_{11}$')—, —N(R$_{11}$')C(O)N(R$_{11}$')—, —N(R$_{11}$')— where in each case is independently selected from hydrogen, hydrocarbyl or substituted hydrocarbyl, —Si(OR$_8$')$_w$(R$_8$')$_t$—, where w and t are each independently selected from 0 to 2, provided that the sum of w and t is 2, and each R$_8$' is independently selected from hydrogen, hydrocarbyl and substituted hydrocarbyl, and combinations of two or more interrupting groups thereof.

In accordance with some embodiments, and with further reference to Formula (IV), the multivalent polymer, from which $L^1$ can be selected, is selected from multivalent polyurethane, multivalent polyester, multivalent polyether, multivalent poly(meth)acrylate, multivalent polyvinylalcohol, multivalent polycarbonate, multivalent polysiloxane, and multivalent cyclic polysiloxane. The multivalent polymers from which $L^1$ can be selected can be prepared in accordance with art-recognized methods from art-recognized materials including, but not limited to, art-recognized monomers. With some embodiments, (a) at least some of the monomers from which the polymer is prepared (and of which $L^1$ is a residue) have covalently bonded thereto one or more photochromic compounds according to the present invention; and/or (b) the resulting polymer (of which $L^1$ is a residue) is subsequently modified to include photochromic compounds according to the present invention bonded thereto. The multivalent polymers from which $L^1$ can be selected can, with some embodiments, have any suitable backbone architecture, such as but not limited to, alternating backbone architecture, block backbone architecture, random backbone architecture, and combinations thereof. The multivalent polymers from which $L^1$ can be selected can, with some further embodiments, have any suitable macro polymer architecture, such as but not limited to, linear polymer architecture, branched polymer architecture, comb polymer architecture, star polymer architecture, dendritic polymer architecture, and combinations thereof.

With further reference to Formula (IV), and in accordance with some embodiments, the multivalent hydrocarbyl group, the multivalent substituted hydrocarbyl group, the multivalent interrupted hydrocarbyl group, and the multivalent substituted interrupted hydrocarbyl group, each independently comprise a residue selected from, a residue of a polyisocyanate, a residue of a polyol, a residue of a polycarboxylic acid, a residue of a polycarbonate functional material, and combinations thereof.

Classes of polyisocyanates that can be a residue of the multivalent hydrocarbyl group, the multivalent substituted hydrocarbyl group, the multivalent interrupted hydrocarbyl group, and the multivalent substituted interrupted hydrocarbyl group, from which $L^1$ of Formula (IV) can be selected, include, but are not limited to, aliphatic polyisocyanates, aromatic polyisocyanates, cycloaliphatic polyisocyanates, and heterocyclic polyisocyanates, in each case having at least 2 isocyanate groups, dimers of such polyisocyanates, trimers of such polyisocyanates, and mixtures of such polyisocyanates. Examples of polyisocyanates that can be a residue of the multivalent hydrocarbyl group, the multivalent substituted hydrocarbyl group, the multivalent interrupted hydrocarbyl group, and the multivalent substituted interrupted hydrocarbyl group, from which $L^1$ of Formula (IV) can be selected, include, but are not limited to, toluene-2,4-diisocyanate; toluene-2,6-diisocyanate; diphenyl methane-4,4'-diisocyanate; diphenyl methane-2,4'-diisocyanate; para-phenylene diisocyanate; biphenyl diisocyanate; 3,3'-dimethyl-4,4'-diphenylene diisocyanate; tetramethylene-1,4-diisocyanate; hexamethylene-1,6-diisocyanate; 2,2,4-trimethyl hexane-1,6-diisocyanate; lysine methyl ester diisocyanate; bis(isocyanato ethyl)fumarate; isophorone diisocyanate; ethylene diisocyanate; dodecane-1,12-diisocyanate; cyclobutane-1,3-diisocyanate; cyclohexane-1,3-diisocyanate; cyclohexane-1,4-diisocyanate; methyl cyclohexyl diisocyanate; hexahydrotoluene-2,4-diisocyanate; hexahydrotoluene-2,6-diisocyanate; hexahydrophenylene-1,3-diisocyanate; hexahydrophenylene-1,4-diisocyanate; perhydrodiphenylmethane-2,4'-diisocyanate; perhydrodiphenylmethane-4,4'-diisocyanate, dimers thereof, trimers thereof, and mixtures thereof.

Classes of polyols that can be a residue of the multivalent hydrocarbyl group, the multivalent substituted hydrocarbyl group, the multivalent interrupted hydrocarbyl group, and the multivalent substituted interrupted hydrocarbyl group, from which $L^1$ of Formula (IV) can be selected, include, but are not limited to, aliphatic polyols, aromatic polyols, cycloaliphatic polyols, and heterocyclic polyols, in each case having at least 2 hydroxyl groups. Examples of polyols that can be a residue of the multivalent hydrocarbyl group, the multivalent substituted hydrocarbyl group, the multivalent interrupted hydrocarbyl group, and the multivalent substituted interrupted hydrocarbyl group, from which $L^1$ of Formula (IV) can be selected, include, but are not limited to, trimethylolpropane, di(trimethylolpropane), trimethylolethane, di(trimethylolethane), trishydroxyethylisocyanurate, pentaerythritol, di(pentaerythritol) ethylene glycol, propylene glycol, trimethylene glycol, butanediol, heptanediol, hexanediol, octanediol, 4,4'-(propane-2,2-diyl)dicyclohexanol, 4,4'-methylenedicyclohexanol, neopentyl glycol, 2,2,3-trimethylpentane-1,3-diol, 1,4-dimethylolcyclohexane, 2,2,4-trimethylpentane diol, 4,4'-(propane-2,2-diyl)diphenol, and 4,4'-methylenediphenol.

Classes of polycarboxylic acids that can be a residue of the multivalent hydrocarbyl group, the multivalent substituted hydrocarbyl group, the multivalent interrupted hydrocarbyl group, and the multivalent substituted interrupted hydrocarbyl group, from which $L^1$ of Formula (IV) can be selected, include, but are not limited to, aliphatic polycarboxylic acids, aromatic polycarboxylic acids, cycloaliphatic polycarboxylic acids, and heterocyclic polycarboxylic acids, in each case having at least 2 carboxylic acid groups and/or carboxylic acid ester groups. Examples of polycarboxylic acids that can be a residue of the multivalent hydrocarbyl group, the multivalent substituted hydrocarbyl group, the multivalent interrupted hydrocarbyl group, and the multivalent substituted interrupted hydrocarbyl group, from which $L^1$ of Formula (IV) can be selected, include, but are not limited to, benzene-1,2,4-tricarboxylic acid, phthalic acid, tetrahydrophthalic acid, hexahydrophthalic acid, endobicyclo-2,2,1,5-heptyne-2,3-dicarboxylic acid, tetrachlorophthalic acid, cyclohexanedioic acid, succinic acid, isophthalic acid, terephthalic acid, azelaic acid, maleic acid, trimesic acid, 3,6-dichlorophthalic acid, adipic acid, sebacic acid, and like multifunctional carboxylic acids.

Classes of polycarbonate functional materials/compounds that can be a residue of the multivalent hydrocarbyl group, the multivalent substituted hydrocarbyl group, the multivalent interrupted hydrocarbyl group, and the multivalent substituted interrupted hydrocarbyl group, from which $L^1$ of Formula (IV) can be selected, include, but are not limited to, aliphatic polycarbonate functional compounds, aromatic polycarbonate functional compounds, cycloaliphatic polycarbonate functional compounds, and heterocyclic polycarbonate functional compounds, in each case having at least 2 cyclic carbonate groups. The polycarbonate functional compounds can be prepared in accordance with art-recognized methods. In accordance with some embodiments, the polycarbonate functional compounds are prepared by heating oxirane functional precursor materials in the presence of carbon dioxide and an appropriate catalyst, such as a tetraalkyl ammonium iodide and/or tetraalkyl ammonium bromide, for example, tetrabutylammonium iodide and/or tetrabutylammonium bromide. In accordance with some embodiments, the oxirane functional precursor material is prepared by reacting one more of a polyol with at least two moles of epichlorohydrin, so as to convert at least two of the hydroxyl groups of the polyol to oxirane functional groups. The polyol can, with some embodiments, be selected from those classes and examples of polyols as recited previously herein with regard to $L^1$.

In accordance with some embodiments, and as discussed previously herein: $R^3$, $R^4$, $R^5$ independently for each n, and $R^6$ independently for each p, are in each case independently selected from a reactive substituent and a compatibilizing substituent; and B and B' are each independently an aryl group that is mono-substituted with a reactive substituent or a compatibilizing substituent. If the photochromic compounds of the present invention include multiple reactive substituents and/or multiple compatibilizing substituents, each reactive substituent and each compatibilizing substituent can be independently chosen.

The reactive substituent and the compatibilizing substituent are each independently represented, with some embodiments, in each case by one of the following representative formulas:

| | |
|---|---|
| -A'-D-E-G-J | (XX); |
| -G-E-G-J | (XXIII); |
| -D-E-G-J | (XXVI); |
| -A'-D-J | (XXI); |
| -D-G-J | (XXIV); |
| -D-J | (XXVII); |
| -A'-G-J | (XXII); |
| -G-J | (XXV); |
| and | |
| -A'-J | (XXVIII). |

With reference to formulas (XX) through (XXVIII), non-limiting examples of groups that -A'- can represent according to various non-limiting embodiments disclosed herein include —O—, —C(=O)—, —CH$_2$—, —OC(=O)— and —NHC(=O)—, provided that if -A'- represents —O—, -A'- forms at least one bond with -J.

Non-limiting examples of groups that -D- can represent according to various non-limiting embodiments include a diamine residue or a derivative thereof, wherein a first amino nitrogen of the diamine residue can form a bond with -A'-, or a substituent or an available position on the photochromic compound of the present invention, and a second amino nitrogen of the diamine residue can form a bond with -E-, -G- or -J; and an amino alcohol residue or a derivative thereof, wherein an amino nitrogen of the amino alcohol residue can form a bond with -A'-, or a substituent or an available position on the photochromic compound of the present invention, and an alcohol oxygen of the amino alcohol residue can form a bond with -E-, -G- or -J. Alternatively, according to various non-limiting embodiments, the amino nitrogen of the amino alcohol residue can form a bond with -E-, -G- or -J, and the alcohol oxygen of the amino alcohol residue can form a bond with -A'-, or a substituent or an available position on the photochromic compounds of the present invention.

Non-limiting examples of suitable diamine residues that -D- can represent include an aliphatic diamine residue, a cyclo aliphatic diamine residue, a diazacycloalkane residue, an azacyclo aliphatic amine residue, a diazacrown ether residue, and an aromatic diamine residue. More particular, illustrative and non-limiting examples of diamine residues that can be used in conjunction with various embodiments of the present invention include the following:

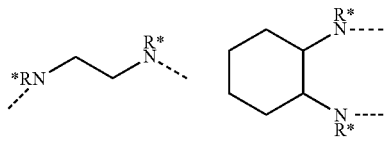

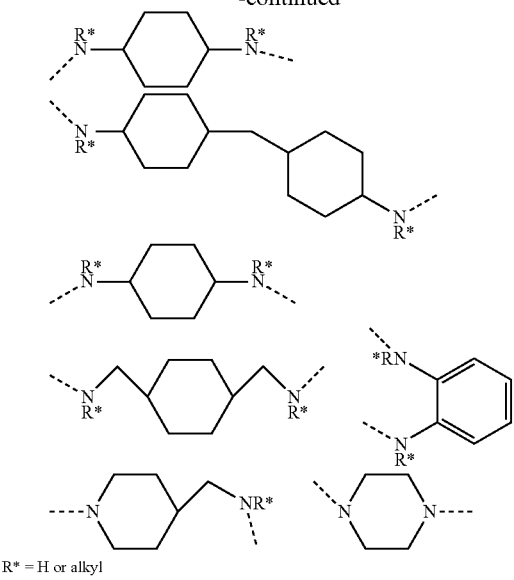

R* = H or alkyl

Non-limiting examples of suitable amino alcohol residues that -D- can represent include an aliphatic amino alcohol residue, a cyclo aliphatic amino alcohol residue, an azacyclo aliphatic alcohol residue, a diazacyclo aliphatic alcohol residue and an aromatic amino alcohol residue. More particular, illustrative and non-limiting examples of amino alcohol residues that can be used in conjunction with various embodiments present invention include the following:

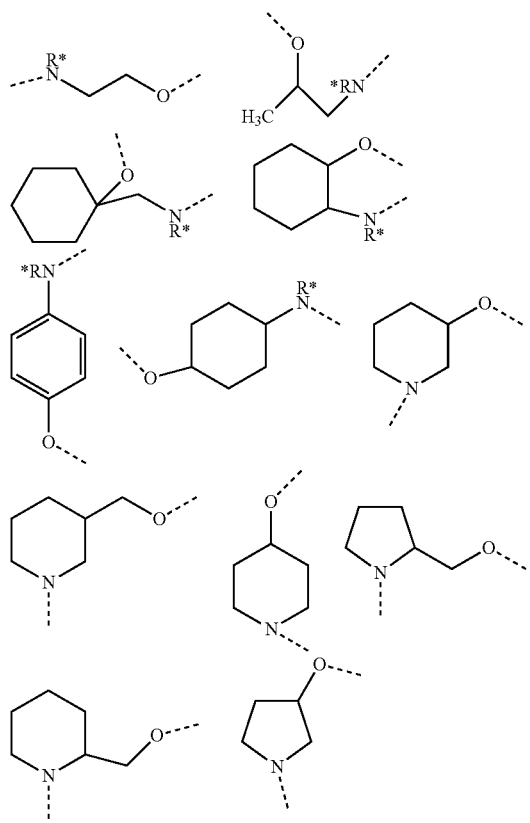

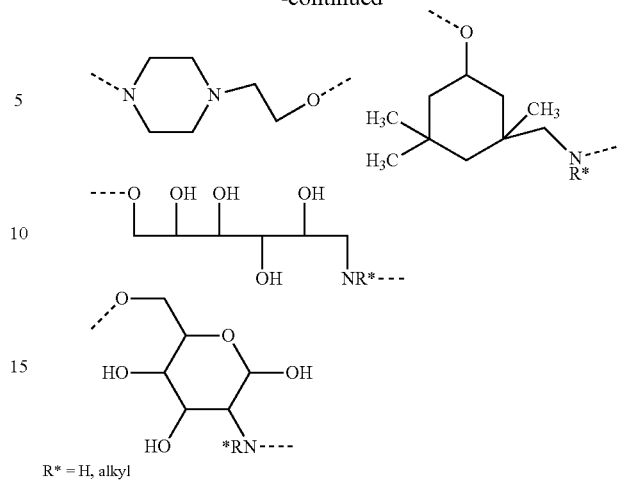

R* = H, alkyl

With continued reference to formulas (XX) through (XXVIII) above, and in accordance to various embodiments, -E- can represent a dicarboxylic acid residue or a derivative thereof, wherein a first carbonyl group of said dicarboxylic acid residue can form a bond with -G- or -D-, and a second carbonyl group of the dicarboxylic acid residue can form a bond with -G-. Non-limiting examples of suitable dicarboxylic acid residues that -E- can represent include an aliphatic dicarboxylic acid residue, a cycloaliphatic dicarboxylic acid residue and an aromatic dicarboxylic acid residue. More particular, illustrative and non-limiting examples of dicarboxylic acid residues that can be used in conjunction with various embodiments of the present invention include the following:

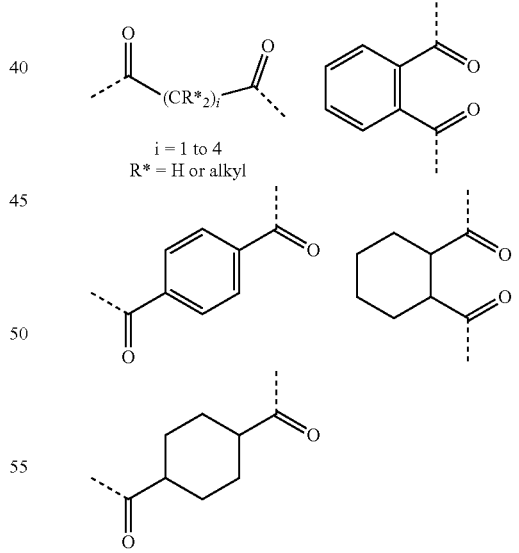

i = 1 to 4
R* = H or alkyl

In accordance with some embodiments of the present invention, -G- can represent a group represented by the following general formula,

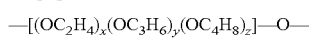

—[(OC$_2$H$_4$)$_x$(OC$_3$H$_6$)$_y$(OC$_4$H$_8$)$_z$]—O— in which x, y and z are each independently chosen and range from 0 to 50, and a sum of x, y, and z ranges from 1 to 50; a polyol residue or a derivative thereof, wherein a first polyol oxygen of the polyol residue can form a bond with -A'-, -D-, -E-, or a substituent or an available position on the photochromic indeno-fused pyran compound, and a second polyol oxygen of the polyol can form a bond with -E- or -J; or a combination thereof, wherein the first polyol oxygen of the polyol residue forms a bond with a group —[(OC$_2$H$_4$)$_x$(OC$_3$H$_6$)$_y$(OC$_4$H$_8$)$_z$]— (i.e., to form the group —[(OC$_2$H$_4$)$_x$(OC$_3$H$_6$)$_y$(OC$_4$H$_8$)$_z$]—O—), and the second polyol oxygen forms a bond with -E- or -J. Non-limiting examples of suitable polyol residues that -G- can represent include an aliphatic polyol residue, a cyclo aliphatic polyol residue and an aromatic polyol residue.

Illustrative and non-limiting examples of polyols from which the polyol residues that -G- can represent can be formed, according to some embodiments, include (a) low molecular weight polyols having an average molecular weight less than 500, such as, but not limited to, those set forth in U.S. Pat. No. 6,555,028 at col. 4, lines 48-50, and col. 4, line 55 to col. 6, line 5, which disclosure is hereby specifically incorporated by reference herein; (b) polyester polyols, such as, but not limited to, those set forth in U.S. Pat. No. 6,555,028 at col. 5, lines 7-33, which disclosure is hereby specifically incorporated by reference herein; (c) polyether polyols, such as but not limited to those set forth in U.S. Pat. No. 6,555,028 at col. 5, lines 34-50, which disclosure is hereby specifically incorporated by reference herein; (d) amide-containing polyols, such as, but not limited to, those set forth in U.S. Pat. No. 6,555,028 at col. 5, lines 51-62, which disclosure is hereby specifically incorporated by reference; (e) epoxy polyols, such as, but not limited to, those set forth in U.S. Pat. No. 6,555,028 at col. 5 line 63 to col. 6, line 3, which disclosure is hereby specifically incorporated by reference herein; (f) polyhydric polyvinyl alcohols, such as, but not limited to, those set forth in U.S. Pat. No. 6,555,028 at col. 6, lines 4-12, which disclosure is hereby specifically incorporated by reference herein; (g) urethane polyols, such as, but not limited to those set forth in U.S. Pat. No. 6,555,028 at col. 6, lines 13-43, which disclosure is hereby specifically incorporated by reference herein; (h) polyacrylic polyols, such as, but not limited to those set forth in U.S. Pat. No. 6,555,028 at col. 6, lines 43 to col. 7, line 40, which disclosure is hereby specifically incorporated by reference herein; (i) polycarbonate polyols, such as, but not limited to, those set forth in U.S. Pat. No. 6,555,028 at col. 7, lines 41-55, which disclosure is hereby specifically incorporated by reference herein; and (j) mixtures of such polyols.

With further reference to formulas (XX) through (XXVIII), and in accordance with some embodiments, -J can represent a group —K, wherein —K represents a group such as, but not limited to,
—CH$_2$COOH, —CH(CH$_3$)COOH, —C(O)(CH$_2$)$_w$COOH, —C$_6$H$_4$SO$_3$H, —C$_6$H$_{10}$SO$_3$H, —C$_4$H$_8$SO$_3$H, —C$_3$H$_6$SO$_3$H, —C$_2$H$_4$SO$_3$H, and —SO$_3$H,
wherein subscript w ranges from 1 to 18. In accordance with some further embodiments, -J can represent hydrogen that forms a bond with an oxygen or a nitrogen of linking group to form a reactive moiety such as —OH or —NH. For example, and with some embodiments, -J can represent hydrogen, provided that if -J represents hydrogen, -J is bonded to an oxygen of -D- or -G-, or a nitrogen of -D-.

In accordance with further embodiments, -J can represent a group -L' or residue thereof, wherein -L' can represent a reactive moiety. For example, and in accordance with some embodiments, -L' can represent a group such as, but not limited to, acryl, methacryl, crotyl, 2-(methacryloxy)ethylcarbamyl, 2-(methacryloxy)ethoxycarbonyl, 4-vinylphenyl, vinyl, 1-chlorovinyl or epoxy. As used herein, the terms acryl, methacryl, crotyl, 2-(methacryloxy)ethylcarbamyl, 2-(methacryloxy)ethoxycarbonyl, 4-vinylphenyl, vinyl, 1-chlorovinyl, and epoxy refer to the following structures:

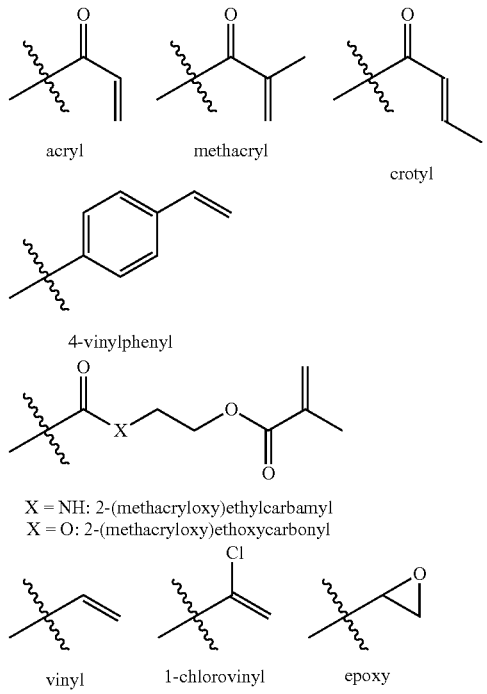

As previously discussed, -G- can represent a residue of a polyol, which can include hydroxy-containing carbohydrates, such as those set forth in U.S. Pat. No. 6,555,028 at col. 7, line 56 to col. 8, line 17, which disclosure is hereby specifically incorporated by reference herein. The polyol residue can be formed, for example and without limitation herein, by the reaction of one or more of the polyol hydroxyl groups with a precursor of -A'-, such as a carboxylic acid or a methylene halide, a precursor of polyalkoxylated group, such as polyalkylene glycol, or a hydroxyl substituent of the indeno-fused naphthopyran. The polyol can be represented by q-(OH)$_a$ and the residue of the polyol can be represented by the formula —O-q-(OH)$_{a-1}$, wherein q is the backbone or main chain of the polyhydroxy compound and "a" is at least 2.

Further, as discussed above, one or more of the polyol oxygens of -G- can form a bond with -J (i.e., forming the group -G-J). For example, although not limiting herein, wherein the reactive and/or compatiblizing substituent comprises the group -G-J, if -G- represents a polyol residue and -J represents a group —K that contains a carboxyl terminating group, -G-J can be produced by reacting one or more polyol hydroxyl groups to form the group —K (for example as discussed with respect to Reactions B and C at col. 13, line 22 to col. 16, line 15 of U.S. Pat. No. 6,555,028, which disclosure is hereby specifically incorporated by reference herein) to produce a carboxylated polyol residue. Alternatively, if -J represents a group —K that contains a sulfo or sulfono terminating group, although not limiting herein, -G-J can be produced by acidic condensation of one or more of the polyol hydroxyl groups with HOC$_6$H$_4$SO$_3$H; HOC$_6$H$_{10}$SO$_3$H; HOC$_4$H$_8$SO$_3$H; HOC$_3$H$_6$SO$_3$H; HOC$_2$H$_4$SO$_3$H; or H$_2$SO$_4$, respectively. Further, although not limiting herein, if -G- represents a polyol residue and -J represents a group -L' chosen from acryl, methacryl, 2-(methacryloxy)ethylcarbamyl and epoxy, -L' can be added by condensation of the polyol residue with acryloyl chloride, methacryloyl chloride, 2-isocyanatoethyl methacrylate or epichlorohydrin, respectively.

With reference to Formulas (Ia) and (Ib), and in accordance with some embodiments, $R^1$ and $R^2$ do not together form a ring structure, in which case $R^1$ and $R^2$ can each be independently selected from one or more groups described previously herein with regard to $R^3$, $R^4$, $R^5$, and $R^6$.

With some embodiments, the photochromic compounds of the present invention, such as described with reference to Formula (Ia) and Formula (Ib), can each be used alone, or in combination with other photochromic compounds. For example, the photochromic compounds of the present invention can be used in conjunction with other photochromic compounds having activated absorption maxima within the range of 300 to 1000 nanometers. Further, the photochromic compounds according to the present invention can be used in conjunction with a complementary conventional polymerizable or a compatiblized photochromic compound, such as for example, those disclosed in U.S. Pat. No. 6,113,814 (at col. 2, line 39 to col. 8, line 41), and U.S. Pat. No. 6,555,028 (at col. 2, line 65 to col. 12, line 56), which disclosures are hereby specifically incorporated by reference herein.

The photochromic compounds of the present invention can be used in combination with a mixture of other photochromic compounds. For example, although not limiting herein, mixtures of photochromic compounds can be used to attain certain activated colors such as a near neutral gray or near neutral brown. See, for example, U.S. Pat. No. 5,645,767, col. 12, line 66 to col. 13, line 19, which describes the parameters that define neutral gray and brown colors and which disclosure is specifically incorporated by reference herein.

Examples of classes of other photochromic compounds that can be used in combination with the photochromic compounds of the present invention, include, but are not limited to, indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof.

Non-limiting examples of photochromic pyrans that can be used in combination with the photochromic compounds of the present invention, include, but are not limited to, benzopyrans, naphthopyrans, e.g., naphtho[1,2-b]pyrans, naphtho[2,1-b]pyrans, indeno-fused naphthopyrans, such as those disclosed in U.S. Pat. No. 5,645,767, and heterocyclic-fused naphthopyrans, such as those disclosed in U.S. Pat. Nos. 5,723,072, 5,698,141, 6,153,126, and 6,022,497, which are hereby incorporated by reference; spiro-9-fluoreno[1,2-b]pyrans; phenanthropyrans; quinopyrans; fluoroanthenopyrans; spiropyrans, e.g., spiro(benzindoline)naphthopyrans, spiro(indoline)benzopyrans, spiro(indoline)naphthopyrans, spiro(indoline)quinopyrans and spiro(indoline)pyrans. Further examples of naphthopyrans and complementary organic photochromic compounds are described in U.S. Pat. No. 5,658,501, which are hereby specifically incorporated by reference herein. Spiro(indoline)pyrans are also described in the text, *Techniques in Chemistry*, Volume III, "Photochromism", Chapter 3, Glenn H. Brown, Editor, John Wiley and Sons, Inc., New York, 1971, which is hereby incorporated by reference.

Non-limiting examples of photochromic oxazines that can be used in combination with the photochromic compounds of the present invention, include, but are not limited to, benzoxazines, naphthoxazines, and spiro-oxazines, e.g., spiro(indoline)naphthoxazines, spiro(indoline)pyridobenzoxazines, spiro(benzindoline)pyridobenzoxazines, spiro(benzindoline)naphthoxazines, spiro(indoline)benzoxazines, spiro(indoline)fluoranthenoxazine, and spiro(indoline)quinoxazine. Non-limiting examples of photochromic fulgides that can be used in combination with the photochromic compounds of the present invention, include, but are not limited to: fulgimides, and the 3-furyl and 3-thienyl fulgides and fulgimides, which are disclosed in U.S. Pat. No. 4,931,220 (which are hereby specifically incorporated by reference) and mixtures of any of the aforementioned photochromic materials/compounds.

In accordance with the present invention there is also provided a photochromic composition, which includes at least one photochromic compound according to the present invention, such as represented by Formula (Ia) and/or Formula (Ib), as described previously herein.

In accordance with some embodiments of the present invention, the photochromic composition includes: (i) an organic material, in which the organic material is at least one of a polymeric material, an oligomeric material, and/or a monomeric material; and (ii) a photochromic compound according to the present invention, which is incorporated into at least a portion of the organic material. The photochromic compound can be incorporated into a portion of the organic material by methods including, but not limited to, at least one of blending and/or bonding the photochromic compound with the organic material or a precursor of the organic material. As used herein with reference to the incorporation of photochromic compounds into an organic material, the terms "blending" and "blended" mean that the photochromic compound/material is intermixed or intermingled with the at least a portion of the organic material, but not bonded to the organic material. Further, as used herein with reference to the incorporation of photochromic compounds into an organic material, the terms "bonding" or "bonded" mean that the photochromic compound/material is linked, such as by one or more covalent bonds, to a portion of the organic material or a precursor thereof. For example, although not limiting herein, the photochromic material can be linked to the organic material through a reactive substituent.

In accordance with some embodiments of the present invention, when the organic material is a polymeric material, the photochromic compound can be incorporated into at least a portion of the polymeric material or at least a portion of the monomeric material or oligomeric material from which the polymeric material is formed. For example, photochromic compound(s) according to the present invention that have a reactive substituent can be bonded to an organic material such as a monomer, oligomer, or polymer having a group with which a reactive moiety may be reacted, or the reactive moiety can be reacted as a co-monomer in the polymerization reaction from which the organic material is formed, for example, in a co-polymerization process.

As discussed above, the photochromic compositions according to present invention can include an organic material chosen from a polymeric material, an oligomeric material and/or a monomeric material, with some embodiments.

Examples of polymeric materials that can be used with the photochromic compositions of the present invention include, but are not limited to: polymers of bis(allyl carbonate) monomers; diethylene glycol dimethacrylate monomers; diisopropenyl benzene monomers; ethoxylated bisphenol A dimethacrylate monomers; ethylene glycol bismethacrylate monomers; poly(ethylene glycol) bismethacrylate monomers; ethoxylated phenol bismethacrylate monomers; alkoxylated polyhydric alcohol acrylate monomers, such as ethoxylated trimethylol propane triacrylate monomers; urethane acrylate monomers; vinylbenzene monomers; and styrene. Further examples of suitable polymeric materials include, but are not limited to, polymers of polyfunctional, e.g., mono-, di- or multi-functional, acrylate and/or methacrylate monomers; poly($C_1$-$C_{12}$ alkyl methacrylates), such as poly(methyl methacrylate); poly(oxyalkylene)dimethacrylate; poly(alkoxylated phenol methacrylates); cellulose acetate; cellulose triacetate; cellulose acetate propionate; cellulose acetate butyrate; poly(vinyl acetate); poly(vinyl alcohol); poly(vinyl chloride); poly(vinylidene chloride); polyurethanes; polythiourethanes; thermoplastic polycarbonates; polyesters; poly(ethylene terephthalate); polystyrene; poly(alpha-methylstyrene); copolymers of styrene and methyl methacrylate; copolymers of styrene and acrylonitrile; polyvinylbutyral; and polymers of diallylidene pentaerythritol, particularly copolymers with polyol (allyl carbonate) monomers, e.g., diethylene glycol bis(allyl carbonate), and acrylate monomers, such as ethyl acrylate, butyl acrylate. Also contemplated are copolymers of the aforementioned monomers, combinations, and blends of the aforementioned polymers and copolymers with other polymers (e.g., to form interpenetrating network products).

With some embodiments transparency of the photochromic composition is desired, in which case the organic material can be a transparent polymeric material. The polymeric material can be, with some embodiments, an optically clear polymeric material prepared from a thermoplastic polycarbonate resin, such as the resin derived from bisphenol A and phosgene, which is sold under the trademark, LEXAN®; a polyester, such as the material sold under the trademark, MYLAR®; a poly(methyl methacrylate), such as the material sold under the trademark, PLEXIGLAS®; and polymerizates of a polyol(allyl carbonate) monomer, especially diethylene glycol bis(allyl carbonate), which monomer is sold under the trademark CR-39®; and polyurea-polyurethane (polyurea urethane) polymers, which are prepared, for example, by the reaction of a polyurethane oligomer and a diamine curing agent, a composition for one such polymer being sold under the trademark TRIVEX® by PPG Industries, Inc. Other non-limiting examples of suitable polymeric materials include polymerizates of copolymers of a polyol (allyl carbonate), e.g., diethylene glycol bis(allyl carbonate), with other copolymerizable monomeric materials, such as, but not limited to: copolymers with vinyl acetate, copolymers with a polyurethane having terminal diacrylate functionality, and copolymers with aliphatic urethanes, the terminal portion of which contain allyl or acrylyl functional groups. Still other suitable polymeric materials include, without limitation, poly(vinyl acetate), polyvinylbutyral, polyurethane, polythiourethanes, polymers chosen from diethylene glycol dimethacrylate monomers, diisopropenyl benzene monomers, ethoxylated bisphenol A dimethacrylate monomers, ethylene glycol bismethacrylate monomers, poly(ethylene glycol) bismethacrylate monomers, ethoxylated phenol bismethacrylate monomers and ethoxylated trimethylol propane triacrylate monomers, cellulose acetate, cellulose propionate, cellulose butyrate, cellulose acetate butyrate, polystyrene and copolymers of styrene with methyl methacrylate, vinyl acetate and acrylonitrile. According to further embodiments, the polymeric material can be an optical resin commercially available from PPG Industries, Inc. under the CR-designation, such as CR-307, CR-407, and CR-607.

In accordance with some embodiments, the organic material can be a polymeric material which is chosen from poly(carbonate), copolymers of ethylene and vinyl acetate; copolymers of ethylene and vinyl alcohol; copolymers of ethylene, vinyl acetate, and vinyl alcohol (such as those that result from the partial saponification of copolymers of ethylene and vinyl acetate); cellulose acetate butyrate; poly (urethane); poly(acrylate); poly(methacrylate); epoxies; aminoplast functional polymers; poly(anhydride); poly(urea urethane); N-alkoxymethyl(meth)acrylamide functional polymers; poly(siloxane); poly(silane); and combinations and mixtures thereof.

With some further embodiments, the photochromic composition of the present invention further includes at least one of, a complementary photochromic material (including one or more of those other photochromic materials and compounds described previously herein), a photoinitiator, a thermal initiator, a polymerization inhibitor, a solvent, a light stabilizer, a heat stabilizer, a mold release agent, a rheology control agent, a leveling agent, a free radical scavenger, and/or an adhesion promoter.

In accordance with some embodiments, the photochromic composition according to the present invention is a photochromic coating composition. Photochromic coating compositions according to some embodiments of the present invention include: a photochromic material according to the present invention, such as described previously herein with regard to Formulas (Ia) and (Ib); a resin composition that is optionally curable; and optionally a solvent. The photochromic coating composition can be in the form of art-recognized liquid coatings and powder coatings. The photochromic coating compositions of the present invention can be thermoplastic or thermosetting coating compositions. In an embodiment, the photochromic coating composition is a curable or thermosetting coating composition.

The curable resin composition of the curable photochromic coating compositions according to some embodiments of the present invention include: a first reactant (or component) having functional groups, e.g., an epoxide functional polymer reactant; and a second reactant (or component) that is a crosslinking agent having functional groups that are reactive towards and that can form covalent bonds with the functional groups of the first reactant. The first and second reactants of the curable resin composition of the curable photochromic coating composition can each independently include one or more functional species, and are each present in amounts sufficient to provide cured photochromic coatings having a desirable combination of physical properties, e.g., smoothness, optical clarity, solvent resistance, and hardness.

Examples of curable resin compositions that can be used with the curable photochromic coating compositions according to the present invention include, but are not limited to: curable resin compositions including epoxide functional polymer (e.g., (meth)acrylic polymers containing residues of glycidyl (meth)acrylate and epoxide reactive crosslinking agent (e.g., containing active hydrogens, such as hydroxyls, thiols and amines); and curable resin compositions including hydroxy functional polymer and capped (or blocked) isocyanate functional crosslinking agent.

With some embodiments, the curable resin composition of the photochromic coating composition of the present invention is a curable urethane (or polyurethane) resin composition. Curable urethane resin compositions useful in the photochromic coating compositions of the present invention typically include: an active hydrogen functional polymer, such as a hydroxy functional polymer; and a capped (or blocked) isocyanate functional crosslinking agent. Hydroxy functional polymers that can be used in such compositions include, but are not limited to, art-recognized hydroxy functional vinyl polymers, hydroxy functional polyesters, hydroxy functional polyurethanes and mixtures thereof.

Vinyl polymers having hydroxy functionality can be prepared by free radical polymerization methods that are known to those of ordinary skill in the art. In an embodiment of the present invention, the hydroxy functional vinyl polymer is prepared from a majority of (meth)acrylate monomers and is referred to herein as a "hydroxy functional (meth)acrylic polymer."

Hydroxy functional polyesters useful in curable photochromic coating compositions comprising capped isocyanate functional crosslinking agent can be prepared by art-recognized methods. Typically, diols and dicarboxylic acids or diesters of dicarboxylic acids are reacted in a proportion such that the molar equivalents of hydroxy groups is greater than that of carboxylic acid groups (or esters of carboxylic acid groups) with the concurrent removal of water or alcohols from the reaction medium.

Hydroxy functional urethanes can be prepared by art-recognized methods, for example, as previously described herein. Typically one or more difunctional isocyanates are reacted with one or more materials having two active hydrogen groups (e.g., diols or dithiols), such that the ratio of active hydrogen groups to isocyanate groups is greater than 1, as is known to the skilled artisan.

By "capped (or blocked) isocyanate crosslinking agent" is meant a crosslinking agent having two or more capped isocyanate groups that can decap (or deblock) under cure conditions, e.g., at elevated temperature, to form free isocyanate groups and free capping groups. The free isocyanate groups formed by decapping of the crosslinking agent are preferably capable of reacting and forming substantially permanent covalent bonds with the active hydrogen groups of the active hydrogen functional polymer (e.g., with the hydroxy groups of a hydroxy functional polymer).

It is desirable that the capping group of the capped isocyanate crosslinking agent not adversely affect the curable photochromic coating composition upon decapping from the isocyanate (i.e., when it becomes a free capping group). For example, it is desirable that the free capping group neither become trapped in the cured film as gas bubbles nor excessively plasticize the cured film. Capping groups useful in the present invention preferably have the characteristics of being nonfugitive or capable of escaping substantially from the forming coating prior to its vitrification. Typically, the free capping groups escape substantially from the forming (e.g., curing) coating prior to its vitrification.

Classes of capping groups of the capped isocyanate crosslinking agent can be selected from: hydroxy functional compounds, e.g., linear or branched $C_2$-$C_8$ alcohols, ethylene glycol butyl ether, phenol and p-hydroxy methylbenzoate; 1H-azoles, e.g., 1H-1,2,4-triazole and 1H-2,5-dimethyl pyrazole; lactams, e.g., e-caprolactam and 2-pyrolidinone; ketoximes, e.g., 2-propanone oxime and 2-butanone oxime. Other suitable capping groups include, morpholine, 3-aminopropyl morpholine and N-hydroxy phthalimide.

The isocyanate or mixture of isocyanates of the capped isocyanate crosslinking agent has two or more isocyanate groups (e.g., 3 or 4 isocyanate groups). Examples of suitable isocyanates that can be used to prepare the capped isocyanate crosslinking agent include, monomeric diisocyanates, e.g., α, α'-xylylene diisocyanate, α, α, α', α'-tetramethylxylylene diisocyanate and 1-isocyanato-3-isocyanatomethyl-3,5,5-trimethylcyclohexane (isophorone diisocyanate or IPDI), and dimers and trimers of monomeric diisocyanates containing isocyanurate, uretidino, biruet or allophanate linkages, e.g., the trimer of IPDI.

The capped isocyanate crosslinking agent can also be selected from oligomeric capped isocyanate functional adducts. As used herein, by "oligomeric capped polyisocyanate functional adduct" is meant a material that is substantially free of polymeric chain extension. Oligomeric capped polyisocyanate functional adducts can be prepared by art-recognized methods from, for example, a compound containing three or more active hydrogen groups, e.g., trimethylolpropane (TMP), and an isocyanate monomer, e.g., 1-isocyanato-3,3,5-trimethyl-5-isocyanatomethylcyclohexane (IPDI), in a molar ratio of 1:3, respectively. In the case of TMP and IPDI, by employing art-recognized starved feed and/or dilute solution synthesis techniques, an oligomeric adduct having an average isocyanate functionality of 3 can be prepared (e.g., "TMP-3IPDI"). The three free isocyanate groups per TMP-3IPDI adduct are then capped with a capping group, e.g., a linear or branched $C_2$-$C_8$ alcohol.

To catalyze the reaction between the isocyanate groups of the capped polyisocyanate crosslinking agent and the hydroxy groups of the hydroxy functional polymer, one or more catalysts are typically present in the curable photochromic coating composition in amounts of from, for example, 0.1 to 5 percent by weight, based on total resin solids of the composition. Classes of useful catalysts include but are not limited to, metal compounds, in particular, organic tin compounds, e.g., tin(II) octanoate and dibutyltin (IV) dilaurate, and tertiary amines, e.g., diazabicyclo[2.2.2]octane.

Curable photochromic coating compositions according to the present invention, which include hydroxy functional polymer and capped isocyanate functional crosslinking agent, typically have present therein hydroxy functional polymer in an amount of from 55 percent to 95 percent by weight, based on total resin solids weight of the composition, e.g., from 75 percent to 90 percent by weight, based on total resin solids weight of the composition. The capped isocyanate functional crosslinking agent is typically present in the curable resin composition in an amount corresponding to the balance of these recited ranges, i.e., 5 to 45, particularly 10 to 25, percent by weight.

With the curable urethane resin compositions of the curable photochromic coating compositions of the present invention, the equivalent ratio of isocyanate equivalents in the capped isocyanate crosslinking agent to hydroxy equivalents in the hydroxy functional polymer is typically within the range of 1:3 to 3:1, e.g., 1:2 to 2:1. While equivalent ratios outside of this range can be employed, they are generally less desirable due to performance deficiencies in cured photochromic films obtained therefrom. Curable photochromic coating compositions according to the present invention that include hydroxy functional polymer and capped isocyanate functional crosslinking agent are typically cured at a temperature of from 120° C. to 190° C. over a period of from 10 to 60 minutes.

Photochromic coating compositions according to the present invention can, with some embodiments, optionally further include a solvent. Examples of suitable solvents include, but art not limited to, acetates, alcohols, ketones, glycols, ethers, aliphatics, cycloaliphatics and aromatics. Examples of acetates include, but are not limited to, ethyl acetate, butyl acetate, and glycol acetate. Examples of ketones include, but are not limited to, methyl ethyl ketone and methyl-N-amyl ketone. Examples of aromatics include, but are not limited to, are toluene, naphthalene and xylene. In an embodiment, one or more solvents are added to each of the first reactant and the second reactant. Suitable solvent blends can include, for example, one or more acetates, propanol and its derivatives, one or more ketones, one or more alcohols and/or one or more aromatics. If present, the solvent is typically present in an amount of from 5 to 60 percent by weight, or 5 to 40 percent by weight, or 10 to 25 percent by weight, based on the total weight of the photochromic coating composition (inclusive of the solvent weight).

Curable photochromic coating compositions according to the present invention can, with some embodiments, optionally contain additives such as waxes for flow and wetting, flow control agents, e.g., poly(2-ethylhexyl)acrylate, adjuvant resin to modify and optimize coating properties, antioxidants and ultraviolet (UV) light absorbers. Examples of useful antioxidants and UV light absorbers include those available commercially from Ciba-Geigy under the trademarks IRGANOX and TINUVIN. These optional additives, when used, are typically present in amounts up to 20 percent by weight (e.g., from 0.5 to 10 percent by weight), based on total weight of resin solids of the curable resin composition.

Photochromic compositions, photochromic articles and photochromic coating compositions according to the present invention can, with some embodiments, further include art-recognized additives that aid or assist in the processing and/or performance of the compositions or articles. Non-limiting examples of such additives include photoinitiators, thermal initiators, polymerization inhibitors, solvents, light stabilizers (such as, but not limited to, ultraviolet light absorbers and light stabilizers, such as hindered amine light stabilizers (HALS)), heat stabilizers, mold release agents, rheology control agents, leveling agents (such as, but not limited to, surfactants), free radical scavengers, adhesion promoters (such as hexanediol diacrylate and coupling agents), and combinations and mixtures thereof.

The photochromic compounds of the present invention can be used in amounts (or ratios) such that the compositions, organic material or substrate (e.g., photochromic articles and photochromic coatings) into which the photochromic compounds are incorporated or otherwise connected exhibits desired optical properties. With some embodiments, the amount and types of photochromic material can be selected such that the composition, organic material or substrate is clear or colorless when the photochromic compound is in the closed-form (e.g., in the bleached or unactivated state), and can exhibit a desired resultant color when the photochromic compound (such as a photochromic thieno-thienyl cyclopyran of the present invention) is in the open-form (e.g., when activated by actinic radiation). The precise amount of the photochromic material that is utilized in the various photochromic compositions and articles described herein is not critical provided that a sufficient amount is used to produce the desired effect. The particular amount of the photochromic material used can depend on a variety of factors, such as but not limited to, the absorption characteristics of the photochromic compound, the color and intensity of the color desired upon activation, and the method used to incorporate or connect the photochromic material to the substrate. Photochromic compositions according to some embodiments of the present invention can include the photochromic material according to the present invention, including the compounds represented by Formulas (Ia) and/or (Ib), in an amount of from 0.01 to 40 weight percent, or from 0.05 to 15, or from 0.1 to 5 weight percent, based on the weight of the photochromic composition. For purposes of further non-limiting illustration, the amount of the photochromic compound/material including the compounds represented by Formulas (Ia) and/or (Ib) that is incorporated into an organic material can range from 0.01 to 40 weight percent, or from 0.05 to 15, or from 0.1 to 5 weight percent, based on the weight of the organic material.

The present invention also relates to photochromic articles that include one or more photochromic compounds according to the present invention, such as represented by Formula (Ia) and Formula (Ib). The photochromic articles are, with some embodiments, prepared by art-recognized methods, such as by imbibition methods, cast-in-place methods, coating methods, in-mold coating methods, over-mold methods, and lamination methods.

With some embodiments, the photochromic articles are selected from ophthalmic articles, display articles, windows, mirrors, and active liquid crystal cell articles, and passive liquid crystal cell articles.

In accordance with some further embodiments, the photochromic articles of the present invention are selected from ophthalmic articles, and the ophthalmic articles are selected from corrective lenses, non-corrective lenses, contact lenses, intra-ocular lenses, magnifying lenses, protective lenses, and visors.

With some additional embodiments, the photochromic articles of the present invention are selected from display articles, and the display articles are selected from screens, monitors, and security elements.

The photochromic compounds of the present invention, such as represented by Formulas (Ia) and (Ib), can be prepared in accordance with art-recognized methods. With reference to the Schemes depicted in the drawing figures, the various groups, such as $R_3$, $R_4$, $R_5$, $R_6$, B, and B', and related subscripts, such as n and p, of the various intermediates, reactants, and/or compounds depicted are each as described previously herein, and/or represent precursors of such groups as described previously herein.

With reference to Scheme-(1) of FIG. 1, and for purposes of non-limiting illustration of the preparation of photochromic compounds according to the present invention, such as represented by Formula (Ia) and more particularly by Formula (Ia-IIa), in what is referred to herein as a Borylation Step, a methyl 2-(2-bromophenyl)acetate compound (a) is reacted with 4,4,4',4',5,5,5',5'-octamethyl 2,2'-bis-(1,3,2-dioxaboralane) compound (b) in the presence of a first catalyst (Cat.-(1)), which is [1,1'-bis(diphenylphosphino)ferrocene]dichloropalladium(II), and a suitable solvent, such as dioxane, under a nitrogen blanket, at elevated temperature, such as 80° C., and for a suitable period of time, such as 8 hours. The Borylation Step results in the formation of an ortho-(tetramethyl-1,3,2-dioxaborolan) phenyl methylacetate compound (c).

With further reference to Scheme-1 of FIG. 1, and in what is referred to herein as a Cross Coupling Step, compound (c) is next reacted with a 3-bromothieno[3,2-b]thiophene compound (d) in the presence of a second catalyst (Cat.-(2)), which is [1,1-bis(diphenylphosphino)ferrocene]dichloropalladium(II), under a nitrogen blanket, at elevated temperature, such as 80° C., and for a suitable period of time, such as 8 hours. The Cross Coupling Step results in the formation of a methyl 2-(2-(thieno[3,2-b]thiophen-3-yl)phenyl)acetate compound (e).

With further reference to Scheme-1 of FIG. 1, and in what is referred to herein as a Methanolysis Step, the methyl 2-(2-(thieno[3,2-b]thiophen-3-yl)phenyl)acetate compound (e) is converted to a 2-(2-(thieno[3,2-b]thiophen-3-yl)phenyl)acetic acid compound (f) in the presence of base (KOH) and a suitable solvent, such as ethanol and water, followed by art-recognized work-up procedures.

With further reference to Scheme-1 of FIG. 1, and in what is referred to herein as a Ring Closure Step, the 2-(2-(thieno[3,2-b]thiophen-3-yl)phenyl)acetic acid compound (f) is next converted to a naphtho[2,1-b]thieno[2,3-d]thiophen-6-ol compound (h) in the presence of a protonic acid, such as methyl sulfonic acid (g), followed by art-recognized work-up procedures.

With further reference to Scheme-1 of FIG. 1, and in what is referred to herein as a Propargyl Alcohol Step, the naphtho[2,1-b]thieno[2,3-d]thiophen-6-ol compound (h) is next reacted with a propargyl alcohol compound (i) in the presence of a protonic acid, such as 4-methylbenzenesulfonic acid, followed by art-recognized work-up procedures, which results in the formation of a 2,2-(B,B')-2H-benzo[f]thieno[2',3':4,5]thieno[3,2-h]chromene compound (j) according to some embodiments of the present invention.

Figure 2:
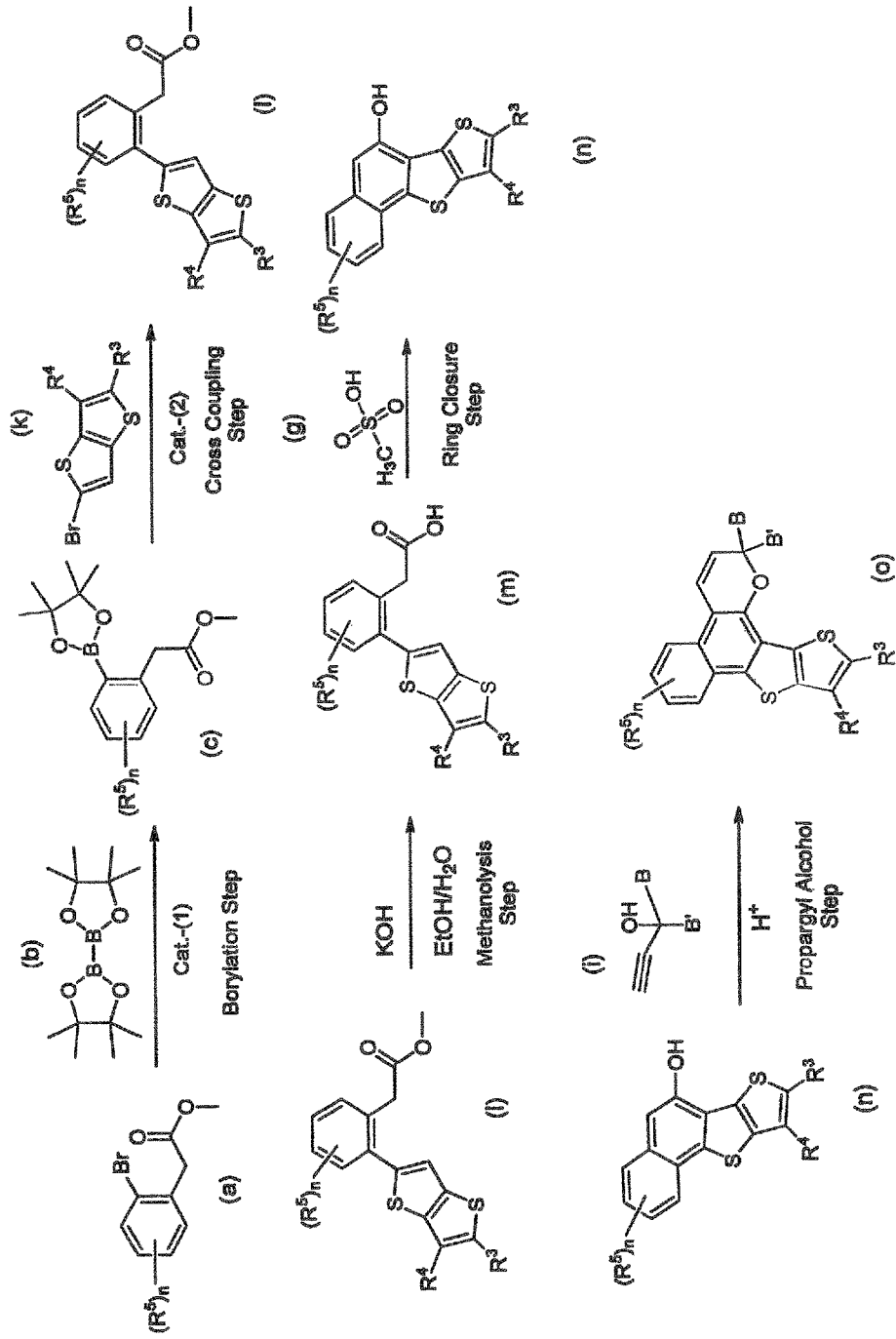
FIG. 2 is an illustrative representative general scheme, Scheme-(2), of a method for preparing photochromic compounds according to some further embodiments of the present invention, such as represented by Formula (Ib-IIa) as described further herein.

With reference to Scheme-(2) of FIG. 2, and for purposes of non-limiting illustration of the preparation of photochromic compounds according to the present invention, such as represented by Formula (Ib), and more particularly by Formula (Ib-IIa), in the initial Borylation Step, a methyl 2-(2-bromophenyl)acetate compound (a) is reacted with 4,4,4',4',5,5,5',5'-octamethyl 2,2'-bis-(1,3,2-dioxaboralane) compound (b) in the presence of a first catalyst (Cat.-(1)), which is [1,1-bis(diphenylphosphino)ferrocene]dichloropalladium(II), and a suitable solvent, such as dioxane, under a nitrogen blanket, at elevated temperature, such as 80° C., and for a suitable period of time, such as 8 hours. The Borylation Step results in the formation of an ortho-(tetramethyl-1,3,2-dioxaborolan) phenyl methylacetate compound (c).

With further reference to Scheme-2 of FIG. 2, in the Cross Coupling Step, compound (c) is next reacted with a 2-bromothieno[3,2-b]thiophene compound (k) in the presence of a second catalyst (Cat.-(2)), which is [1,1'-bis(diphenylphosphino)ferrocene]dichloropalladium(II), under a nitrogen blanket, at elevated temperature, such as 80° C., and for a suitable period of time, such as 8 hours. The Cross Coupling Step results in the formation of a methyl 2-(2-(thieno[3,2-b]thiophen-2-yl)phenyl)acetate compound (I).

With further reference to Scheme-2 of FIG. 2, in the Methanolysis Step, the methyl 2-(2-(thieno[3,2-b]thiophen-2-yl)phenyl)acetate compound (I) is converted to a 2-(2-(thieno[3,2-b]thiophen-2-yl)phenyl)acetic acid compound (m) in the presence of base (KOH) and a suitable solvent, such as ethanol and water, followed by art-recognized work-up procedures.

With further reference to Scheme-2 of FIG. 2, in the Ring Closure Step, the 2-(2-(thieno[3,2-b]thiophen-2-yl)phenyl)acetic acid compound (m) is next converted to a naphtho[1,2-b]thieno[2,3-d]thiophen-6-ol compound (n) in the presence of methyl sulfonic acid (g), followed by art-recognized work-up procedures.

With further reference to Scheme-2 of FIG. 2, in the Propargyl Alcohol Step, the naphtho[1,2-b]thieno[2,3-d]thiophen-6-ol compound (n) is next reacted with a propargyl alcohol compound (i) in the presence of a protonic acid, such as 4-methylbenzenesulfonic acid, followed by art-recognized work-up procedures, which results in the formation of a 2,2-(B,B)-2H-benzo[f]thieno[2',3'1:4,5]thieno[2,3-h]chromene compound (o) according to some embodiments of the present invention.

Figure 3:
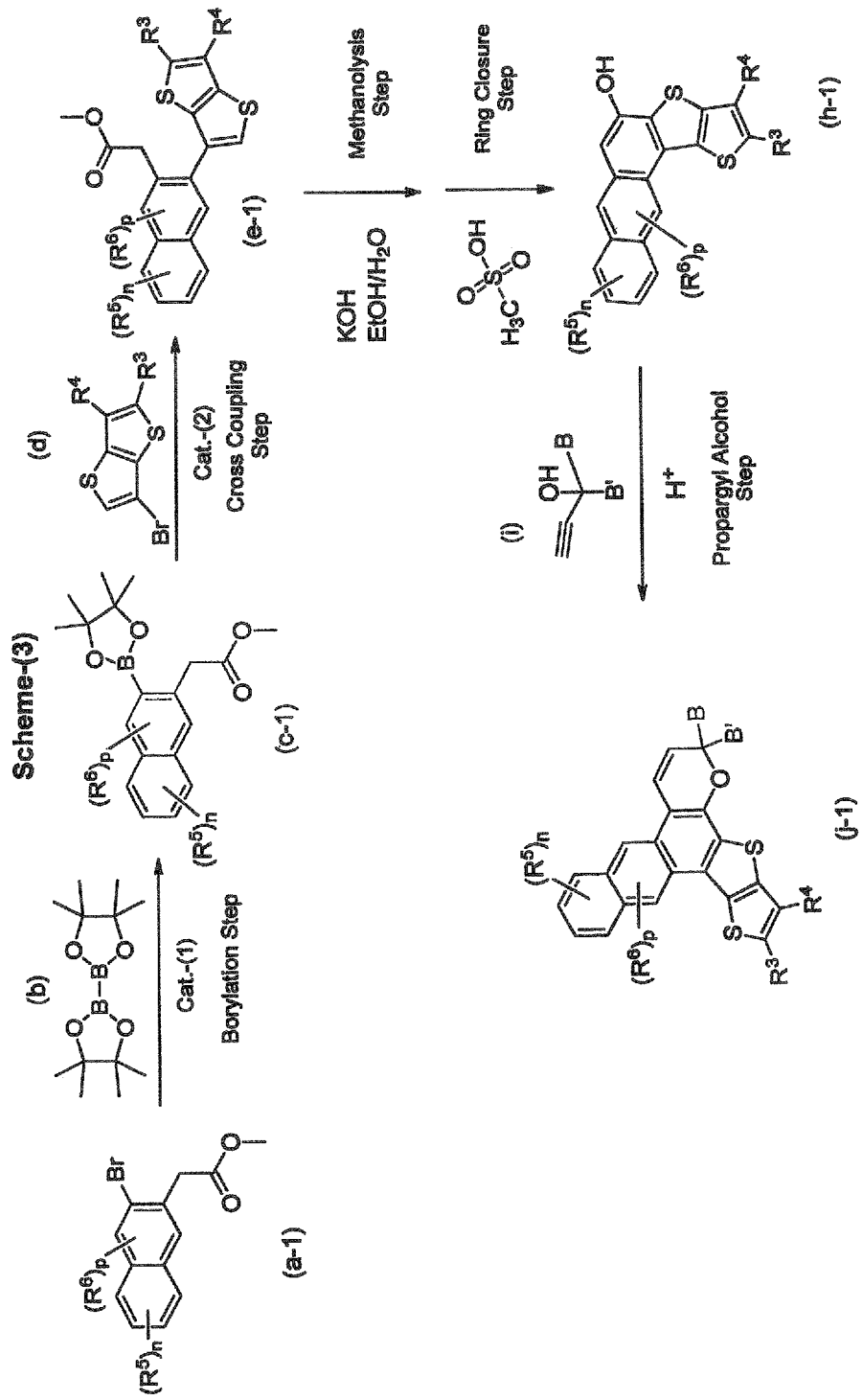
FIG. 3 is a an illustrative representative general scheme, Scheme-(3), of a method for preparing photochromic compounds according to some additional embodiments of the present invention, such as represented by Formula (Ia-IIc) as described further herein.

With reference to Scheme-(3) of FIG. 3, and for purposes of non-limiting illustration, there is depicted the preparation of photochromic compounds according to some embodiments of the present invention, such as represented by Formula (Ia-IIc). In Scheme-(3) of FIG. 3, the reactants, catalysts, solvents, and conditions associated with each of the Borylation Step, Cross Coupling Step, Methanolysis Step, Ring Closure Step, and Propargyl Alcohol Step are as described previously herein, such as with reference to Scheme-(1) of FIG. 1. With further reference to Scheme-(3) of FIG. 3, in the Borylation Step, methyl 3-(2-bromonaphthyl)acetate compound (a-1) is reacted with 4,4,4',4',5,5,5', 5'-octamethyl 2,2'-bis-(1,3,2-dioxaboralane) compound (b), which results in the formation of an ortho-(tetramethyl-1,3,2-dioxaboralan) naphthyl methylacetate compound (c-1).

With further reference to Scheme-(3) of FIG. 3, in the Cross Coupling Step, the ortho-(tetramethyl-1,3,2-dioxaboralan) naphtyl methylacetate compound (c-1) is reacted with a 3-bromothieno[3,2-b]thiophene compound (d), which results in the formation of a methyl 2-(3-thieno[3,2-b]thiophen-3-yl)naphthyl)acetate compound (e-1).

With additional reference to Scheme-(3) of FIG. 3, the methyl 2-(2-theno[3,2-b]thiophene3-yl)naphthyl)acetate compound (e-1) is subjected sequentially to the Methanolysis Step and the Ring closure Step, which results in the formation of an anthraceno-thieno-thiophen-ol compound (h-1). The anthraceno-thieno-thiophen-ol compound (h-1) is next subjected to the Propargyl Alcohol Step, which results in the formation of a thieno-thienyl anthracenopyran compound a-1) according to the present invention.

Figure 4:
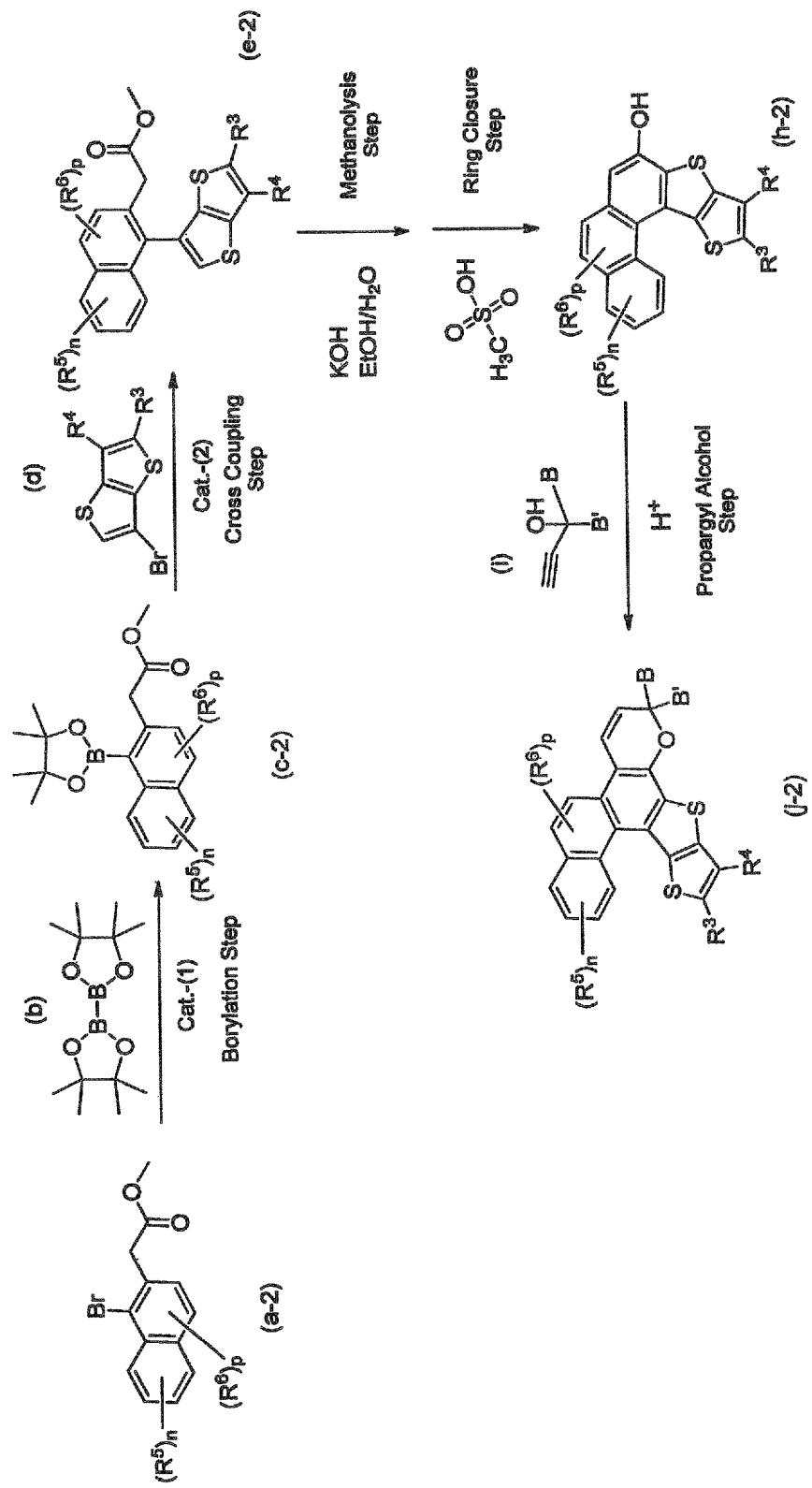
FIG. 4 is an illustrative representative general scheme, Scheme-(4), of a method for preparing photochromic compounds according to some further additional embodiments of the present invention, such as represented by Formula (Ia-IIb-1) as described further herein.

With reference to Scheme-(4) of FIG. 4, and for purposes of non-limiting illustration, there is depicted the preparation of photochromic compounds according to some embodiments of the present invention, such as represented by Formula (Ia-IIb-1). In Scheme-(4) of FIG. 4, the reactants, catalysts, solvents, and conditions associated with each of the Borylation step, Cross Coupling Step, Methanolysis Step, Ring Closure Step, and Propargyl Alcohol Step are as described previously herein, such as with reference to Scheme-(1) of FIG. 1. With further reference to Scheme-(4) of FIG. 4, in the Borylation Step, a methyl 2-(1-bromonaphthyl)acetate compound (a-2) is reacted with 4,4,4',4',5,5,5', 5'-octamethyl 2,2'-bis-(1,2,2-dioxaboralane) compound (b), which results in the formation of a methyl 2-(1-tetramethyl-1,3,2-dioxaboralan-naphthyl)acetate compound (c-2).

With further reference to Scheme-(4) of FIG. 4, in the Cross Coupling Step, the methyl 2-(1-tetramethyl-1,3,2-dioxaboralan-naphthyl)acetate compound (c-2) is reacted with a 3-bromothieno[3,2-b]thiophene compound (d), which results in the formation of a methyl 2-(1-thieno[3,2-b]thiophen-3-yl)naphthyl)acetate compound (e-2).

With additional reference to Scheme-(4) of FIG. 4, the methyl 2-(1-thieno[3,2-b]thiophen-3-yl)naphthyl)acetate compound (e-2) is subjected sequentially to the Methanolysis Step and the Ring closure Step, which results in the formation of a phenanthreno-thieno-thiophen-ol compound (h-2). The phenanthreno-thieno-thiophen-ol compound (h-2) is next subjected to the Propargyl Alcohol Step, which results in the formation of a thieno-thienyl phenanthrenopyran compound (j-2) according to the present invention.

Figure 5:
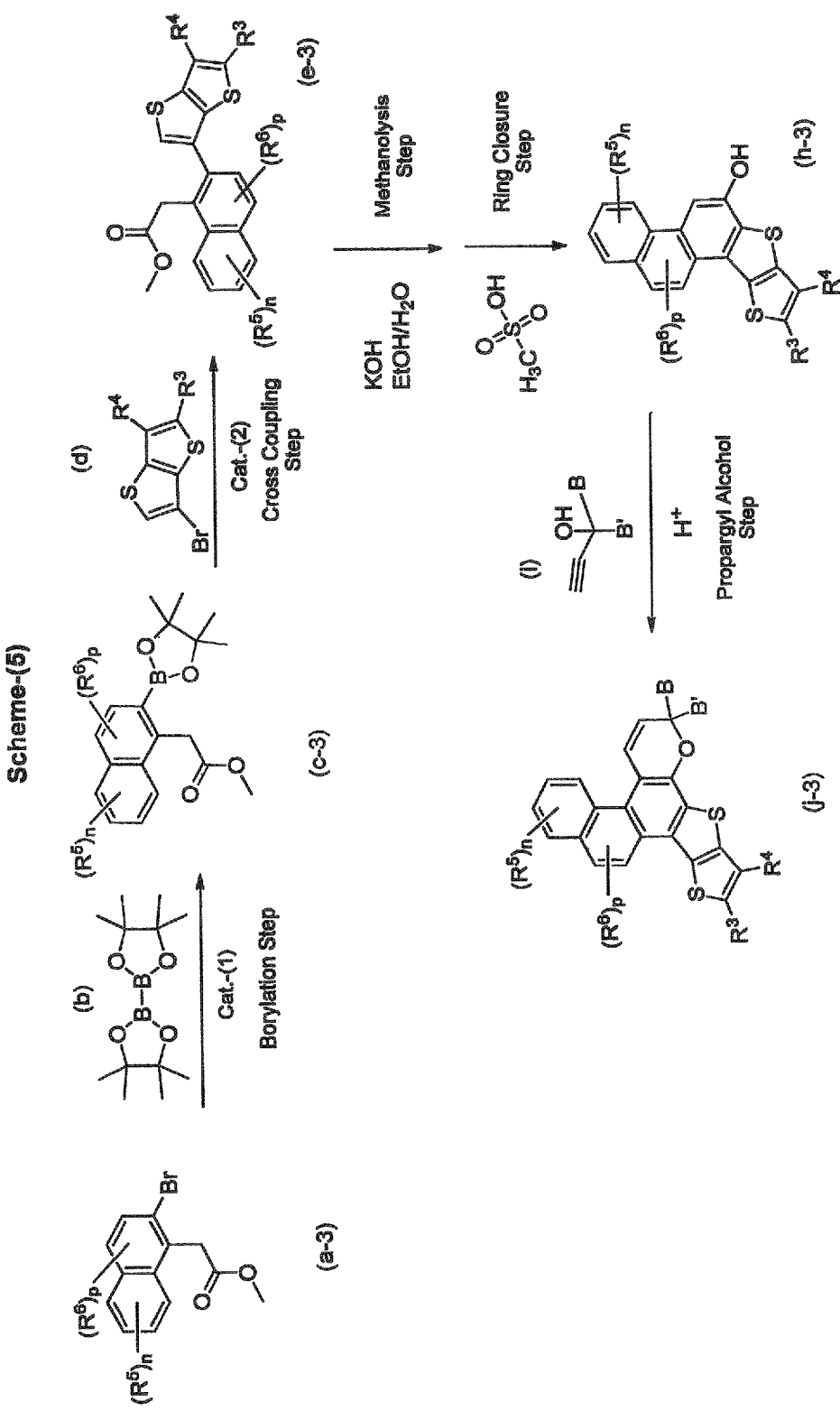
FIG. 5 is an illustrative representative general scheme, Scheme-(5), of a method for preparing photochromic compounds according to some further additional embodiments of the present invention, such as represented by Formula (Ia-IIb-2) as described further herein.

With reference to Scheme-(5) of FIG. 5, and for purposes of non-limiting illustration, there is depicted the preparation of photochromic compounds according to some embodiments of the present invention, such as represented by Formula (Ia-IIb-2). In Scheme-(5) of FIG. 5, the reactants, catalysts, solvents, and conditions associated with each of the Borylation step, Cross Coupling Step, Methanolysis Step, Ring Closure Step, and Propargyl Alcohol Step are as described previously herein, such as with reference to Scheme-(1) of FIG. 1. With further reference to Scheme-(5) of FIG. 5, in the Borylation Step, a methyl 1-(2-bromonaphthyl)acetate compound (a-3) is reacted with 4,4,4',4',5,5,5',5'-octamethyl 2,2'-bis-(1,3,2-dioxaboralane) compound (b), which results in the formation of a methyl 1-(2-tetramethyl-1,3,2-dioxaboralan-naphthyl)acetate compound (c-3).

With further reference to Scheme-(5) of FIG. 5, in the Cross Coupling Step, the methyl 1-(2-tetramethyl-1,3,2-dioxaboralan-naphthyl)acetate compound (c-3) is reacted with a 3-bromothieno[3,2-b]thiophene compound (d), which results in the formation of a methyl 1-(2-thieno[3,2-b]thiophen-3-yl)naphthyl)acetate compound (e-3).

With additional reference to Scheme-(5) of FIG. 5, the methyl 1-(2-thieno[3,2-b]thiophen-3-yl)naphthyl)acetate compound (e-3) is subjected sequentially to the Methanolysis Step and the Ring closure Step, which results in the formation of a phenanthreno-thieno-thiophen-ol compound (h-3). The phenanthreno-thieno-thiophen-ol compound (h-3) is next subjected to the Propargyl Alcohol Step, which results in the formation of a thieno-thienyl phenanthrenopyran compound (j-3) according to the present invention.

Figure 6:
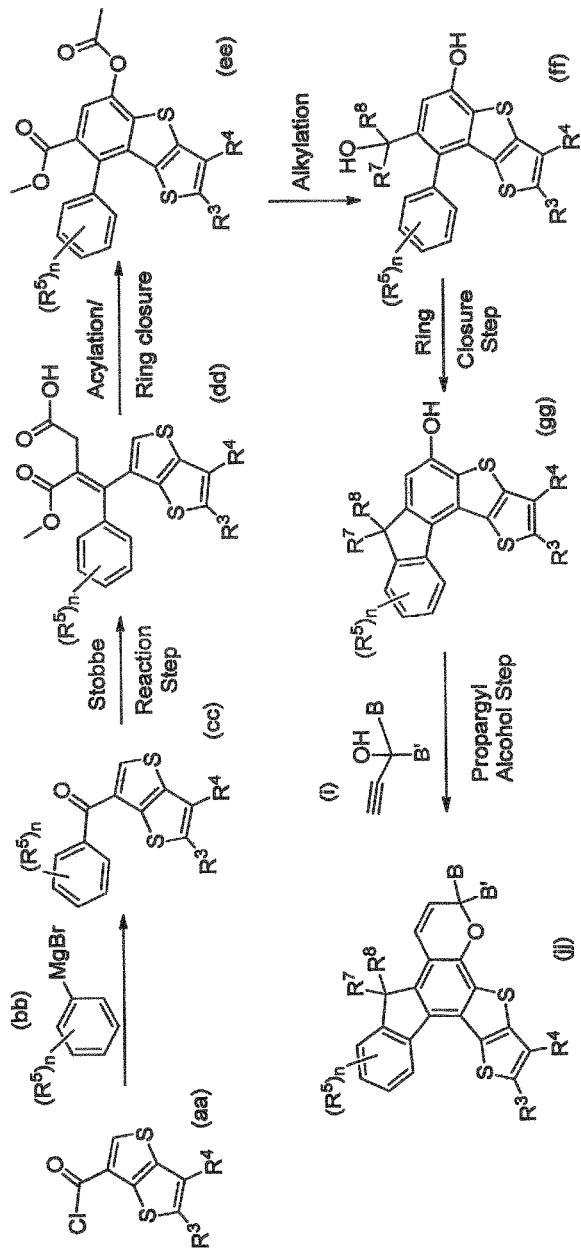
FIG. 6 is an illustrative representative general scheme, Scheme-(6), of a method for preparing photochromic compounds according to some further additional embodiments of the present invention, such as represented by Formula (Ia-IId) as described further herein.

With reference to Scheme-(6) of FIG. 6, and for purposes of non-limiting illustration, there is depicted the preparation of photochromic compounds according to some embodiments of the present invention, such as represented by Formula (Ia-IId). In the first step of Scheme-(6) of FIG. 6, a thieno[3,2-b]thiophene-3-carbonyl chloride compound (aa) is reacted with a phenylmagnesium bromide compound (bb) under art-recognized conditions, which results in the formation of a thieno[3,2-b]thiophene-3-carbonyl phenyl compound (cc). The thieno[3,2-b]thiophene-3-carbonyl phenyl compound (cc) is then reacted with dimethyl succinate in an art-recognized Stobbe Reaction Step, which results in the formation of a half-ester intermediate (dd). The half-ester intermediate (dd) is subjected to art-recognized acylation and ring closure reactions, such as in acetic anhydride and toluene at elevated temperature, which results in the formation of a diester intermediate (ee). The diester intermediate (ee) is then subjected to art-recognized alkylation, such as by reaction with $R^7MgCl$ and $R^8MgCl$, which results in the formation of a hydroxy functional intermediate (ff). The hydroxy functional intermediate (ft) is subjected to an art-recognized ring-closure reaction, such as in the presence of dodecylbenzene sulfonic acid, which results in the formation of a fluoreno[3,4-b]thieno[2,3-d]thiophen-6-ol compound (gg). The fluoreno[3,4-b]thieno[2,3-d]thiophen-6-ol compound (gg) is reacted with a propargyl alcohol (i) in accordance with art-recognized methods, which results in the formation of an indeno[2,1-f]thieno[2',3':4,5]thieno[3,2-h]chromene compound (jj) according to the present invention.

Figure 7:
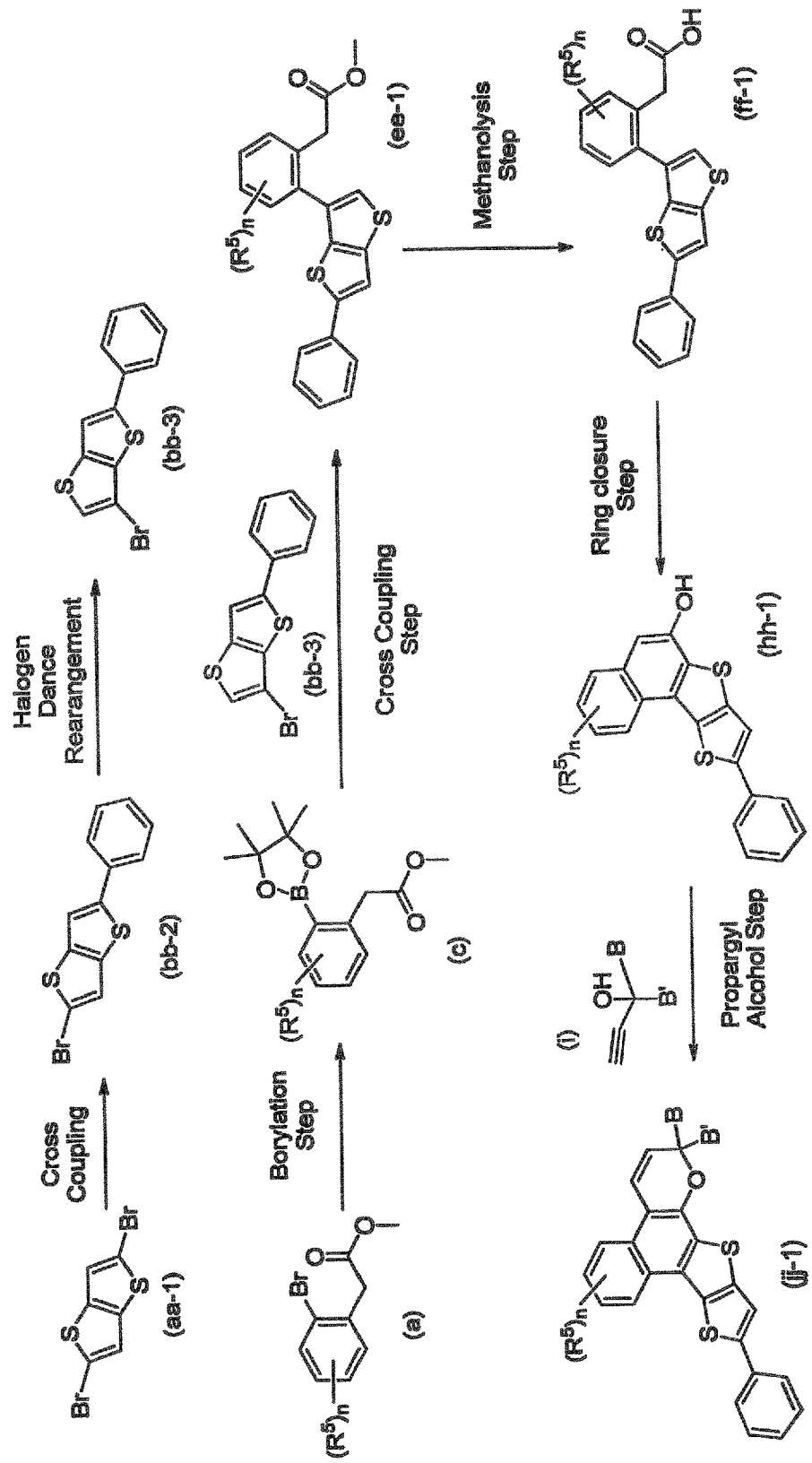
FIG. 7 is an illustrative representative general scheme, Scheme-(7), of a method for preparing photochromic compounds according to some further embodiments of the present invention, such as represented by Formula (Ia-IIa) as described further herein.

With reference to Scheme-(7) of FIG. 7, and for purposes of non-limiting illustration, there is depicted the preparation of photochromic compounds according to some embodiments of the present invention, such as represented by Formula (Ia-IIa), in which $R^3$ thereof is an unsubstituted phenyl group, and $R^4$ is hydrogen. In a preliminary step of Scheme-(7) of FIG. 7, a 2,5-dibromothieno[3,2-b]thiophene compound (aa-1) is subjected to a cross coupling reaction, such as by reaction with 4,4,5,5-tetramethyl-2-phenyl-1,3,2-dioxaborolane (not shown), in accordance with art-recognized methods, which results in the formation of a 2-bromo-5-phenylthieno[3,2-b]thiophene compound (bb-2). The 2-bromo-5-phenylthieno[3,2-b]thiophene compound (bb-2) is subjected to a Halogen Dance Rearrangement in accordance with art-recognized methods, which results in the formation of a 6-bromo-2-phenylthieno[3,2-b]thiopehene compound (bb-3).

In a separate segment of Scheme-(7) of FIG. 7, a methyl 2-(2-bromophenyl)acetate compound (a) is reacted, in a Borylation Step, with 4,4,4',4',5,5,5',5'-octamethyl 2,2'-bis-(1,3,2-dioxaboralane) compound (b) in the presence of a catalyst, which results in the formation of an ortho-(tetramethyl-1,3,2-dioxaborolan) phenyl methyl acetate compound (c), as described previously herein with reference to Scheme-(1) of FIG. 1. The ortho-(tetramethyl-1,3,2-dioxaborolan) phenyl methyl acetate compound (c) is subjected to a Cross Coupling Step by reaction with the previously formed 6-bromo-2-phenylthieno[3,2-b]thiopehene compound (bb-3), under art-recognized methods (such as described with reference to Scheme-(1) of FIG. 1 previously herein) which results in the formation of a methyl 2-(2-(5-phenylthieno[3,2-b]thiophen-3-yl)phenyl)acetate compound (ee-1). The methyl 2-(2-(5-phenylthieno[3,2-b]thiophen-3-yl)phenyl)acetate compound (ee-1) is subjected to a Methanolysis Step in accordance with art-recognized methods (such as described with reference to Scheme-(1) of FIG. 1 previously herein) which results in the formation of a 2-(2-(5-phenylthieno[3,2-b]thiophen-3-yl)phenyl)acetic acid compound (ff-1). The 2-(2-(5-phenylthieno[3,2-b]thiophen-3-yl)phenyl)acetic acid compound (ff-1) is subjected to a Ring Closure Step in accordance with art-recognized methods (such as described with reference to Scheme-(1) of FIG. 1 previously herein) which results in the formation of a 9-phenylnaphtho[2,1-b]thieno[2,3-d]thiophen-6-ol compound (hh-1). The 9-phenylnaphtho[2,1-b]thieno[2,3-d]thiophen-6-ol compound (hh-1) is reacted with a propargyl alcohol compound (i) in accordance with art-recognized methods (such as described with reference to Scheme-(1) of FIG. 1 previously herein) which results in the formation of a 2,2-(B,B')-10-phenyl-2H-benzo[f]thieno[2',3':4,5]thieno[3,2-h]chromene compound (jj-1) according to the present invention.

The present invention is more particularly described in the following examples, which are intended as illustrative only, since numerous modifications and variations therein will be apparent to those skilled in the art.

EXAMPLES

Part 1 provides descriptions of the preparation of photochromic compounds according to some embodiments of the present invention in Examples 1-9. Part 2 provides a description of the testing and photochromic properties of the photochromic compounds prepared in Examples 1-9.

Part 1—Preparation of Photochromic Compounds in Examples 1-9

Example 1

Step 1

While stirring under a nitrogen atmosphere, methyl 2-(2-bromophenyl)acetate (2 g), 4,4,4',4',5,5,5',5'-octamethyl-2,2'-Bi-(1,3,2-dioxaborolane) (2.44 g), and potassium acetate (0.98 g) were added to a three-neck flask containing dioxane (25 mL). The resulting mixture was degassed with nitrogen for 15 minutes followed by addition of [1,1'-bis(diphenylphosphino)ferrocene]dichloropalladium(II) (0.28 g). After degassing with nitrogen for an additional 15 minutes, the mixture was stirred at 80° C. for 8 hr. After cooling to room temperature, the solvent was removed under vacuum and the crude residue was purified by silica gel chromatography. The mass spectrum of the resulting material was consistent with methyl 2-(2-(4,4,5,5-tetramethyl-1,3,2-dioxaborolan-2-yl)phenyl)acetate (2.41 g).

Step 2

While stirring under a nitrogen atmosphere, the product from Step 1 (0.94 g), 3-bromothieno[3,2-b]thiophene (0.62 g) (as prepared in Henssler, J. T. J. Org. Lett. 2009, 11, 3144), and sodium hydrogen carbonate (0.98 g) were added to a three-neck flask containing dioxane (25 mL). The resulting mixture was degassed with nitrogen for 15 minutes followed by addition of [1,1'-bis(diphenylphosphino)ferrocene]dichloropalladium(II) (0.35 g). After degassing with nitrogen for an additional 15 minutes, the mixture was stirred at 80° C. for 8 hr. After cooling to room temperature, the solvent was removed under vacuum and the crude residue was purified by silica gel chromatography; The mass spectrum of the resulting material was consistent with methyl 2-(2-(thieno[3,2-b]thiophen-3-yl)phenyl)acetate (0.30 g).

Step 3

The product from Step 2 (0.22 g) was dissolved in a solution of ethanol (10 mL) and water (5 mL) containing potassium hydroxide (0.13 g). The resulting mixture was heated to reflux with stirring for two hours, followed by removal of the ethanol under reduced pressure. The remaining aqueous mixture was neutralized with hydrochloric acid (1N) and extracted with ethyl acetate. The organic fraction was dried over sodium sulfate, filtered, and the volume reduced under vacuum. Based on HPLC and TLC analysis, the crude material was consistent with the formation of 2-(2-(thieno[3,2-b]thiophen-3-yl)phenyl)acetic acid (0.20 g).

Step 4

The product from Step 3 (0.20 g) was dissolved in toluene (20 mL) and added to methane sulfonic acid (10 mL) and stirred for 30 minutes. The crude product was diluted with ethyl acetate, passed through a silica plug, and the solvents were removed under vacuum. A slurry was formed by the addition of methanol to the resulting residue, followed by collection of solids by filtration and washing with methanol. The mass spectrum of the resulting material was consistent with naphtho[2,1-b]thieno[2,3-d]thiophen-6-ol (0.12 g).

Step 5

4-Methylbenzenesulfonic acid (3 mg) was added to a stirring mixture containing the product from Step 4 (0.042 g), and 1,1-bis(4-methoxyphenyl)prop-2-yn-1-ol (0.066 g) in 1,2-dichloroethane (5 mL). After stirring for two hours, the mixture was washed with water, followed by extraction of the aqueous fraction with ethyl acetate, and drying the combined organic fractions over sodium sulfate. The volume of the organic mixture was reduced under vacuum and the crude residue was purified by column chromatography. The NMR of the orange solid was consistent with 2,2-bis(4-methoxyphenyl)-2H-benzo[f]thieno[2',3':4,5]thieno[3,2-h]chromene (0.063 g).

Example 2

4-Methylbenzenesulfonic acid (3 mg) was added to a stirring mixture containing the product from Step 4 of Example 1 (0.045 g), and 1,1-diphenylprop-2-yn-1-ol (0.073 g) in dichloroethane (5 mL). After stirring for two hours, the mixture was washed with water, followed by extraction of the aqueous fraction with ethyl acetate, and drying the combined organic fractions over sodium sulfate. The volume of the organic mixture was reduced under vacuum and the crude residue was purified by column chromatography. The NMR of the yellow solid was consistent with 2,2-diphenyl-2H-benzo[f]thieno[2',3':4,5]thieno[3,2-h]chromene (0.029 g).

Example 3

4-Methylbenzenesulfonic acid (10 mg) was added to a mixture containing the product from Step 4 of Example 1 (0.045 g), and 1,1-bis(4-fluorophenyl)prop-2-yn-1-ol (0.3 g) in dichloroethane (10 mL). After stirring overnight, the mixture was washed with water, followed by extraction of the aqueous fraction with ethyl acetate, and drying the combined organic fractions over sodium sulfate. The volume of the organic mixture was reduced under vacuum and the crude residue was purified by silica gel chromatography. The NMR of the light yellow solid was consistent with 2,2-bis(4-fluorophenyl)-2H-benzo[f]thieno[2',3':4,5]thieno[3,2-h]chromene (0.186 g).

Example 4

Step 1

While stirring under a nitrogen atmosphere, methyl 2-(2-bromo-4,5-dimethoxyphenyl)acetate (14.76 g) (as prepared in Chang, D. J. Med. Chem. 2012, 55, 10863-10884.), 4,4,4',4',5,5,5',5'-octamethyl-2,2'-Bi-(1,3,2-dioxaborolane) (19.45 g), and potassium acetate (6.26 g) were added to a three-neck flask containing dioxane (180 mL). The resulting mixture was degassed with nitrogen for 15 minutes followed by addition of [1,1'-bis(diphenylphosphino)ferrocene]dichloropalladium(II) (1.49 g). After degassing with nitrogen for an additional 15 minutes, the mixture was stirred at 80° C. for 8 hr. After cooling to room temperature, the solvent was removed under vacuum and the crude residue was purified by silica gel chromatography. The mass spectrum of the resulting material was consistent with methyl 2-(4,5-dimethoxy-2-(4,4,5,5-tetramethyl-1,3,2-dioxaborolan-2-yl)phenyl)acetate (11.64 g).

Step 2

While stirring under a nitrogen atmosphere, the product from Step 1 (4.60 g), 3-bromothieno[3,2-b]thiophene (2.00 g) (as prepared in Henssler, J. T. J Org Lett 2009, 11, 3144), and [1,1'-bis(diphenylphosphino)ferrocene]dichloropalladium(II) (0.67 g) were added to a three-neck flask containing a solution of N,N-Dimethylformamide (40 mL) and water (2 mL). The resulting mixture was degassed with nitrogen for 15 minutes followed by addition of sodium carbonate (5.8 g). After degassing with nitrogen for an additional 15 minutes, the mixture was stirred at 100° C. for 3 hr. After cooling to room temperature, the mixture was washed with water, followed by extraction of the aqueous fraction with ethyl acetate, and drying the combined organic fractions over sodium sulfate. The volume of the organic mixture was reduced under vacuum and the crude residue was purified by silica gel chromatography. The mass spectrum of the resulting material was consistent with methyl 2-(4,5-dimethoxy-2-(thieno[3,2-b]thiophen-3-yl)phenyl)acetate (0.75 g).

Step 3

The product from Step 2 (0.75 g) was dissolved in methanol (20 mL) and aqueous sodium hydroxide (1N, 3 mL) was added. The resulting mixture was heated to reflux with stirring for two hours, followed by removal of the methanol under reduced pressure. The remaining aqueous mixture was neutralized with hydrochloric acid (1N) and extracted with ethyl acetate. The organic fraction was dried over sodium sulfate, filtered, and the volume reduced under vacuum. Based on HPLC and TLC analysis, the crude material was consistent with the formation of 2-(4,5-dimethoxy-2-(thieno[3,2-b]thiophen-3-yl)phenyl)acetic acid (0.71 g).

Step 4

Methane sulfonic acid (6 mL) was slowly added to the product from Step 3 (0.71 g) dissolved in dichloromethane (200 mL). After stirring for 4 hours, the mixture was washed with water, followed by extraction of the aqueous fraction with ethyl acetate, and drying the combined organic fractions over sodium sulfate. The organic fractions were filtered through a silica plug, followed by rinsing the plug with ethyl acetate, and removing the solvent under vacuum. A slurry was formed by the addition of methanol to the resulting residue, followed by collection of solids by filtration and washing with methanol. The mass spectrum of the resulting material was consistent with 2,3-dimethoxynaphtho[2,1-b]thieno[2,3-d]thiophen-6-ol (0.52 g).

Step 5

4-methylbenzenesulfonate; pyridin-1-ium (10 mg) was added to a stirring mixture containing the product from Step 4 (0.23 g), 1-(4-butoxyphenyl)-1-phenylprop-2-yn-1-ol (0.224 g), and trimethoxymethane (0.154 g) in dichloroethane (10 mL) at 50° C. under nitrogen atmosphere. After stirring for 2 hours at 50° C., the mixture was cooled to room temperature and washed with water, followed by extraction of the aqueous fraction with ethyl acetate, and drying the combined organic fractions over sodium sulfate. The volume of the organic mixture was reduced under vacuum and the crude residue was purified by silica gel chromatography. The NMR of the pale solid was consistent with 2-(4-butoxyphenyl)-6,7-dimethoxy-2-phenyl-2H-benzo[f]thieno[2',3':4,5]thieno[3,2-h]chromene (0.180 g).

Example 5

4-Methylbenzenesulfonate; pyridin-1-ium (15 mg) was added to a stirring mixture containing the product from Step 4 of Example 4 (0.197 g), 1-(4-morpholinophenyl)-1-phenylprop-2-yn-1-ol (0.365 g), and trimethoxymethane (0.330 g) in dichloroethane (10 mL) at 50° C. under nitrogen atmosphere. After stirring for 2 hours at 50° C., the mixture was cooled to room temperature and washed with water, followed by extraction of the aqueous fraction with ethyl acetate, and drying the combined organic fractions over sodium sulfate. The volume of the organic mixture was reduced under vacuum and the crude residue was purified by column chromatography. The NMR of the pale solid was consistent with 4-(4-(6,7-dimethoxy-2-phenyl-2H-benzo[f]thieno[2',3':4,5]thieno[3,2-h]chromen-2-yl)phenyl)morpholine (0.210 g).

Example 6

Step 1

To a three neck flask containing N-methyl-2-pyrrolidone (200 mL) was added 2-chlorobenzaldehyde (100 g) under a nitrogen atmosphere, followed by heating to 80° C. Sodium hydrosulfide (114 g) was added in one portion and the mixture stirred for one hour, followed by heating to 180° C. and stirring for 12 hours. The mixture was cooled to room temperature and poured into saturated ammonium chloride solution (1 L) at 0° C. and stirred for one hour. The aqueous portion of the mixture was filtered to obtain an orange sludge, which was suspended in dichloromethane (500 mL) and filtered again to yield a white precipitate (6 g). The mass spectrum of the product was consistent with benzo[b]benzo[4,5]thieno[2,3-d]thiophene.

Step 2

The product from Step 1 (500 mg) was dissolved in anhydrous tetrahydrofuran (5 ml) under a nitrogen atmosphere and cooled in an ice/water bath. n-Butyllithium in hexanes (2.5 M, 2.5 mL) was added via syringe to produce a brown cloudy mixture which was stirred for one hour. Dry oxygen was then bubbled through the mixture for 2 hours during which the mixture became yellow. The mixture was allowed to warm to room temperature and poured into hydrochloric acid (1M, 50 mL). The resulting cloudy mixture was diluted with of ethyl acetate (100 mL), transferred to a 250 ml separatory funnel, and extracted with brine (100 mL). The organic phase was drained and evaporated. The crude product was washed with a minimal amount (2 ml) of ethyl acetate, filtered and dried under reduced pressure to afford a yellow solid (200 mg). The mass and NMR spectra of the purified product were consistent with benzo[b]benzo[4,5]thieno[2,3-d]thiophen-1-ol.

Step 3

The product from Step 2 (100 mg) was dissolved in 1,2-dichloroethane (15 mL) with stirring under a nitrogen atmosphere and a reflux condenser and heated to 75° C. p-Toluenesulfonic acid (10 mg) and trimethyl orthoformate (3 mL) were added followed by 1,1-bis(4-methoxyphenyl) prop-2-yn-1-ol (200 mg). The dark reaction mixture was stirred for six hours at 75° C., then cooled to room temperature. The solvent was removed under reduced pressure and the crude product purified by silica gel chromatography. The mass spectrum of the off-white solid was consistent with 2,2-bis(4-methoxyphenyl)-2H-benzo[4',5]thieno[2',3':4,5]thieno[3,2-h]chromene (31 mg).

Example 7

Step 1

The product from Step 2 of Example 6 (400 mg) was dissolved in N,N-dimethylformamide (10 mL) to produce a yellow solution. N-Bromosuccinimide (278 mg), dissolved in N,N-dimethylformamide (5 mL), was added dropwise. The resulting dark red solution was stirred at room temperature overnight, then diluted with ethyl acetate (100 mL) and poured into a 250 ml separatory funnel. The mixture was washed with water (2×100 mL) then brine (100 mL). The solvent in the organic layer was removed under reduced pressure and the crude product purified by silica gel chromatography to afford 120 mg of a pale yellow solid. The mass and NMR spectra were consistent with 4-bromobenzo[b]benzo[4,5]thieno[2,3-d]thiophen-1-ol.

Step 2

The product from Step 1 (120 mg) was dissolved in tetrahydrofuran (20 mL) along with phenylboronic acid (190 mg). The resulting solution was stirred and sparged with nitrogen under a reflux condenser for 10 minutes, followed by addition of potassium fluoride (180 mg) and water (1 mL). The mixture was sparged with nitrogen another 15 minutes, followed by addition of bis[tri(o-tolyl)phosphine] palladium(II) chloride (118 mg). The mixture was refluxed under nitrogen atmosphere overnight. The crude reaction mixture was cooled to room temperature, filtered through a pad of silica gel eluting with dichloromethane, followed by removal of solvent to afford a brown oil with a mass spectrum consistent with 4-phenylbenzo[b]benzo[4,5]thieno[2,3-d]thiophen-1-ol. The product was used in the next step without further purification.

Step 3

The product from Step 2 was dissolved in 1,2-dichloroethane (20 mL) and heated to 75° C. under a nitrogen atmosphere. Dodecylbenzenesulfonic acid (10 mg) was added, followed by 1,1-bis(4-methoxyphenyl)prop-2-yn-1-ol (536 mg). After stirring 6 hours the reaction mixture was cooled to room temperature and the solvent removed under reduced pressure. The product was purified by silica gel chromatography to afford 40 mg of gray solid with a mass spectrum consistent with 2,2-bis(4-methoxyphenyl)-6-phenyl-2H-benzo[4',5]thieno[2',3':4,5]thieno[3,2-h]chromene.

Example 8

Step 1

The product from Step 1 of Example 7 (250 mg) was dissolved in toluene (20 mL). The resulting solution was sparged with nitrogen gas with stirring for 10 minutes, followed by addition of sodium tert-butoxide (288 mg). The mixture was sparged with nitrogen gas another 10 minutes, followed by addition of bis[tri(o-tolyl)phosphine]palladium (II) chloride (29 mg) in morpholine (0.17 mL). The mixture was then heated to reflux overnight. The mixture was cooled to room temperature and the solvent removed under reduced pressure. The crude product was purified by silica gel chromatography to afford a yellow solid (150 mg) with a mass spectrum consistent with 4-morpholinobenzo[b]benzo[4,5]thieno[2,3-d]thiophen-1-ol.

Step 2

The product from Step 1 (150 mg) was dissolved in 1,2-dichloroethane (15 mL) and heated to 75° C. under a nitrogen atmosphere. Dodecylbenzenesulfonic acid (10 mg) was added, followed by 1,1-bis(4-methoxyphenyl)prop-2-yn-1-ol (268 mg). After stirring 6 hours the reaction mixture was cooled to room temperature and the solvent removed under reduced pressure. The product was purified by silica gel chromatography to afford 60 mg of gray solid with a mass spectrum consistent with 4-(2,2-bis(4-methoxyphenyl)-2H-benzo[4',5']thieno[2',3':4,5]thieno[3,2-h]chromen-6-yl)morpholine.

Example 9

Step 1

((2-Bromophenyl)ethynyl)trimethylsilane (252 mg) and bis(pinacolato)diboron (381 mg) were combined and dissolved in p-dioxane (10 mL). Potassium acetate (300 mg) was added and the mixture sparged with nitrogen under a reflux condenser for 30 minutes. The mixture was then heated to 85° C. and [1,1'-bis(diphenylphosphino)ferrocene]dichloropalladium(II) (82 mg) was added and the mixture stirred at 85° C. overnight under nitrogen atmosphere. The reaction mixture was cooled to room temperature and the solvent removed under reduced pressure. The crude product was purified by silica gel chromatography to afford 300 mg of oily yellow solid with a mass spectrum consistent with trimethyl((2-(4,4,5,5-tetramethyl-1,3,2-dioxaborolan-2-yl)phenyl)ethynyl)silane.

Step 2

The product from Step 1 (900 mg) and the product from Step 1 of Example 7 (500 mg) were combined in a flask and dissolved in a mixture of toluene (35 mL), ethanol (8 mL) and distilled water (8 mL). To this was added finely ground sodium carbonate (480 mg) with vigorous stirring. The mixture was sparged with nitrogen for 20 minutes then heated to 70° C. Bis(triphenylphosphine)palladium(II) dichloride (113 mg) was added and the mixture sparged with nitrogen and additional 10 minutes. After stirring for 2 hours the reaction mixture was cooled to room temperature, then filtered by vacuum. The filtrate was diluted with ethyl acetate (100 mL) and transferred to a 250 ml separatory funnel followed by washing with distilled water (100 mL) then brine (100 mL). The solvent was removed under reduced pressure and the crude product purified by silica gel chromatography to afford 200 mg of a brown oil with a mass spectrum consistent with ((trimethylsilyl)ethynyl)phenyl)benzo[b]benzo[4,5]thieno[2,3-d]thiophen-1-ol.

Step 3

The product from Step 2 (200 mg) was dissolved in 1:1 dichloromethane/methanol (10 mL) and 1 g of potassium carbonate was added. The red mixture was stirred at room temperature for 4 hours, then filtered. The filtrate was diluted with ethyl acetate (50 mL) and transferred to a 125 ml separatory funnel followed by washing with distilled water (100 mL) then brine (100 mL). The solvent was removed under reduced pressure. The resulting solid was dissolved in anhydrous toluene (10 mL) and sparged 20 minutes with nitrogen under a reflux condenser, then heated to 80° C. followed by addition of ground platinum(II) chloride (10 mg). The mixture was stirred under nitrogen for 8 hours, then cooled to room temperature. The solvent was removed under reduced pressure and the crude product purified by silica gel chromatography. The mass spectrum of the purified red-brown solid (30 mg) was consistent with benzo[4,5]thieno[3,2-b]phenanthro[4,3-d]thiophen-8-ol.

Step 4

The product from Step 3 (50 mg) was dissolved in 1,2-dichloroethane (10 mL) and heated to 100° C. under nitrogen with stirring followed by addition of dodecylbenzenesulfonic acid (5 mg), then 1,1-bis(4-methoxyphenyl)prop-2-yn-1-ol (23 mg). The dark mixture was stirred for 1 hour then cooled to room temperature and the solvent removed under reduced pressure. The crude product was purified by silica gel chromatography to yield 40 mg of a red-brown solid. The mass spectrum of the purified product was consistent with 9,9-bis(4-methoxyphenyl)-9H-benzo[4',5]thieno[2',3':4,5]thieno[3,2-h]naphtho[2,1-f]chromene.

Part 2—Photochromic Property Testing

Part 2A—Test Square Preparation

Testing was done with the compounds described in Examples in the following manner. A quantity of compound calculated to yield a $1.5 \times 10^{-3}$ molal solution was added to a flask containing 50 grams of a monomer blend of 4 parts ethoxylated bisphenol A dimethacrylate (BPA 2EO DMA), 1 part poly(ethylene glycol) 600 dimethacrylate, and 0.033 weight percent 2,2'-azobis(2-methyl propionitrile) (AIBN). Each compound was dissolved into the monomer blend by stirring and gentle heating, if necessary. After a clear solution was obtained, the sample was degassed in a vacuum oven for 5-10 minutes at $25 \times 10^{-6}$ torr. Using a syringe, the sample was poured into a flat sheet mold having an interior dimension of 2.2 mm+/−0.3 mm×6 inch (15.24 cm)×6 inch (15.24 cm). The mold was sealed and placed in a horizontal airflow, programmable oven, programmed to ramp from 40° C. to 95° C. over a 5 hour period, maintain the temperature at 95° C. for 3 hours, ramp down to 60° C. over a 2 hour period and then hold at 60° C. for 16 hours. After curing, the mold was opened, and the polymer sheet was cut into 2 inch (5.1 cm) test squares using a utility knife to score and then snap the pieces at the score lines.

Part 2B—Response Testing

Prior to response testing on an optical bench, the test squares from Part 2A were conditioned by exposing them to 365 nm ultraviolet light for 10 minutes at a distance of about 14 cm from the source in order to pre-activate the photochromic compounds in each sample. The UVA irradiance at the sample surface was measured with a Licor Model Li-1800 spectroradiometer and found to be 22.2 Watts per square meter. The samples were then placed under a halogen lamp (500 W, 120V) for 10 minutes at a distance of 36 cm from the lamp in order to bleach, or inactivate, the photochromic compounds in the samples. The illuminance at the sample was measured with a Licor spectroradiometer and found to be 21.9 Klux. The samples were then kept in a dark environment for at least 1 hour prior to testing in order to cool and fade back to a ground state.

The optical bench was fitted with a Newport Model #67005 300-watt Xenon arc lamp, and Model 69911 power supply, Vincent Associates (model VS25S2ZM0R3 with VMM-D4 controller) high-speed computer controlled shutter, a Schott 3 mm KG-2 band-pass filter, which removed short wavelength radiation, neutral density filter(s) to attenuate light from the Xenon lamp, a fused silica condensing lens for beam collimation, and a fused silica water cell/sample holder for maintaining sample temperature in which the test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 23±0.3° C. for photochromic response testing. A Newport Model 689456 Digital Exposure Timer was used to control the intensity of the Xenon arc lamp during activation of the sample.

A custom broadband light source for monitoring response measurements was positioned in a perpendicular manner to a surface of the cell assembly. Increased signal of shorter visible wavelengths was obtained by collecting and combining separately filtered light from a 100-Watt Tungsten halogen lamp. After passing through the sample, the light was refocused into a 2-inch integrating sphere and fed to an Ocean Optics S2000 spectrophotometer by fiber optic cables. Ocean Optics SpectraSuite and PPG proprietary software were used to measure response and control the operation of the optical bench.

Irradiance for response testing of the samples on the optical bench was established at the sample surface using an International Light Research Radiometer, Model IL-1700 with a detector system comprising a Model SED033 detector, B Filter and diffuser. The output display of the radiometer was corrected (factor values set) against a Licor 1800-02 Optical Calibration Calibrator in order to display values representing Watts per square meter UVA. The irradiance at the sample point for initial response testing was set to 3.0 Watts per square meter UVA and approximately 8.6 Klux illuminance. During sample response testing, if a sample darkened beyond an acceptable detection capability limit, the irradiance was lowered to 1.0 Watts per square meter UVA or the sample was remade at a one-half concentration in the copolymer. Adjustment of the output of the filtered Xenon arc lamp was accomplished by increasing or decreasing the current to the lamp through the controller and/or by adding or removing neutral density filters in the light path. The test samples were exposed to the activation light at 31° normal to the surface while being perpendicular to the monitoring light.

Samples were activated in the 23° C. controlled water cell for 30 minutes, then allowed to fade under room light conditions until the change in optical density of the activated sample faded to ¼ of its highest dark (saturated) state or for a maximum of 30 minutes of fade.

Change in optical density (ΔOD) from the bleached state to the darkened state was determined by establishing the initial transmittance, opening the shutter from the Xenon lamp to provide ultraviolet radiation to change the test lens from the bleached state to an activated (i.e., darkened) state. Data was collected at selected intervals of time, measuring the transmittance in the activated state, and calculating the change in optical density according to the formula: ΔOD=log(% Tb/% Ta), where % Tb is the percent transmittance in the bleached state, % Ta is the percent transmittance, in the activated state and the logarithm is to the base 10.

The $\lambda_{max\text{-}vis}$ in the visible light range is the wavelength in the visible spectrum at which the maximum absorption of the activated form of the photochromic compound occurs. The $\lambda_{max\text{-}vis}$ was determined by testing the photochromic test square in a Varian Cary 4000 UV-Visible spectrophotometer or comparable equipment.

The ΔOD/Min, which represents the sensitivity of the photochromic compound's response to UV light, was measured over the first five (5) seconds of UV exposure, then expressed on a per minute basis. The saturation optical density (ΔOD at saturation) was taken under identical conditions except UV exposure was continued for a total of 30 minutes. The fade half-life (T ½) is the time interval in seconds for the ΔOD of the activated form of the photochromic compound in the test squares to reach one half the ΔOD measured after thirty minutes, at room temperature after removal of the source of activating light, e.g., by closing the shutter. The results are summarized in the following Table 1.

TABLE 1

Photochromic Performance Test Results

| Example # | $\lambda_{max\text{-}vis}$ (nm) | Sensitivity (ΔOD/Min) | ΔOD at saturation | T ½ (sec) |
| --- | --- | --- | --- | --- |
| 1 | 486 | 0.597 | 0.254 | 18 |
| 2 | 449 | 0.949 | 0.907 | 77 |
| 3 | 448 | 0.844 | 0.637 | 47 |
| 4 | 469 | 0.855 | 0.828 | 69 |
| 5 | 512 | 0.566 | 0.503 | 63 |
| 6 | 479 | 0.143 | 0.126 | 1228 |
| 7 | 486 | 0.194 | 0.135 | 85 |
| 8 | 485 | 0.395 | 0.464 | 104 |
| 9 | 500 | 0.219 | 0.07 | 10 |

The present invention has been described with reference to specific details of particular embodiments thereof. It is not intended that such details be regarded as limitations upon the scope of the invention except insofar as to the extent that they are included in the accompanying claims.

What is claimed is:

1. A photochromic compound represented by at least one of the following Formulas (Ia) and (Ib), (Ia)

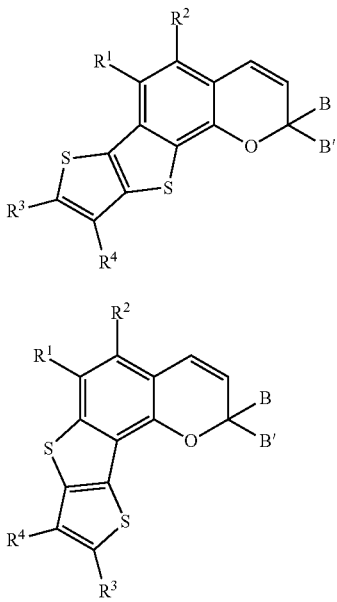

and (Ib)

wherein independently for each of Formulas (Ia) and (Ib),
$R^3$, and $R^4$ are in each case independently selected from, hydrogen; hydrocarbyl;
substituted hydrocarbyl; interrupted hydrocarbyl; substituted interrupted hydrocarbyl, wherein each interrupted hydrocarbyl and each substituted interrupted hydrocarbyl, are in each case independently interrupted with at least one interrupting group selected from the group consisting of —O—, —S—, —C(O)—, —C(O)O—, —OC(O)O—, —B($R_{11'}$)—, —P($R_{11'}$)—, —P(O)($R_{11'}$)—, —S(O)—, —SO$_2$—, —N=N—, —C(O)N($R_{11'}$)—, —OC(O)N($R_{11'}$)—, —N($R_{11'}$)C(O)N($R_{11'}$)—, —N($R_{11'}$)— where $R_{11'}$ in each case is independently selected from hydrogen, hydrocarbyl or substituted hydrocarbyl, —Si(O$R_8'$)$_w$($R_8'$)$_t$—, where w and t are each independently selected from 0 to 2, provided that the sum of w and t is 2, and each $R_8'$ is independently selected from hydrogen, hydrocarbyl and substituted hydrocarbyl, and combinations of two or more interrupting groups thereof; halogen; cyano; and —N($R_{11}''$)$R_{12}'$, wherein $R_{11}''$ and $R_{12}'$ are each independently selected from hydrogen, hydrocarbyl or substituted hydrocarbyl, or $R_{11}''$ and $R_{12}'$ together form a ring structure or a ring structure including at least one heteroatom; or $R^3$ and $R^4$ together form a ring structure;

$R^1$ and $R^2$ together form a ring structure, and said ring structure is selected from the following Formulas (IIa), (IIb), (IIc), and (IId), (IIa)

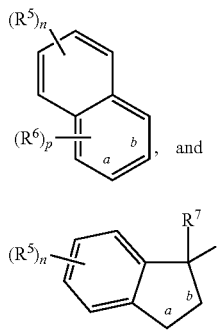

(IIb)

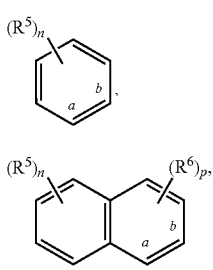

(IIc)

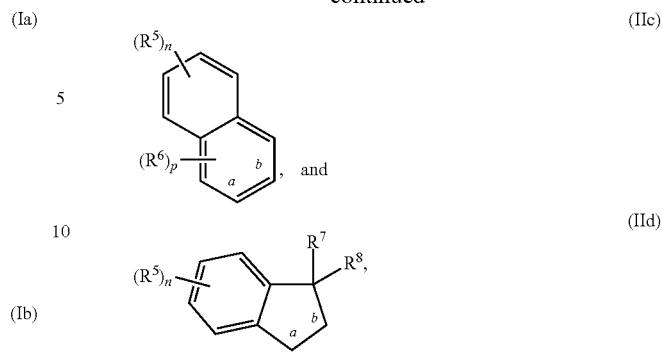

and (IId)

wherein each ring structure represented by Formulas (IIa), (IIb), (IIc), and (IId), is fused to said photochromic compound at carbons a and b, n, independently for Formulas (IIa), (IIb), (IIc), and (IId), is 1 to 4, p, independently for Formulas (IIb) and (IIc), is 1 or 2, $R^5$ independently for each n, and independently for Formulas (IIa), (IIb), (IIc), and (IId), and $R^6$ independently for each p, and independently for Formulas (IIb) and (IIc), are in each case independently selected from, hydrogen; hydrocarbyl; substituted hydrocarbyl; interrupted hydrocarbyl; substituted interrupted hydrocarbyl, wherein each interrupted hydrocarbyl and each substituted interrupted hydrocarbyl, are in each case independently interrupted with at least one interrupting group selected from the group consisting of —O—, —S—, —C(O)—, —C(O)O—, —OC(O)O—, —B($R_{11'}$)—, —P($R_{11'}$)—, —P(O)($R_{11'}$)—, —S(O)—, —SO$_2$—, —N=N—, —C(O)N($R_{11'}$)—, —OC(O)N($R_{11'}$)—, —N($R_{11'}$)C(O)N($R_{11'}$)—, —N($R_{11'}$)— where $R_{11'}$ in each case is independently selected from hydrogen, hydrocarbyl or substituted hydrocarbyl, —Si(O$R_8'$)$_w$($R_8'$)$_t$—, where w and t are each independently selected from 0 to 2, provided that the sum of w and t is 2, and each $R_8'$ is independently selected from hydrogen, hydrocarbyl and substituted hydrocarbyl, and combinations of two or more interrupting groups thereof; halogen; cyano; and —N($R_{11}''$)$R_{12}'$, wherein $R_{11}''$ and $R_{12}'$ are each independently selected from hydrogen, hydrocarbyl or substituted hydrocarbyl, or $R_{11}''$ and $R_{12}'$ together form a ring structure or a ring structure including at least one heteroatom; and $R^7$ and $R^8$ independently for Formula (IId) are each independently selected from hydrogen; hydrocarbyl; substituted hydrocarbyl; interrupted hydrocarbyl; and substituted interrupted hydrocarbyl, wherein each interrupted hydrocarbyl and each substituted interrupted hydrocarbyl, are each independently interrupted with at least one interrupting group selected from the group consisting of —O—, —S—, —N($R_{11'}$)—, where $R_{11'}$ is selected from hydrogen, hydrocarbyl or substituted hydrocarbyl, and combinations of two or more interrupting groups thereof; or $R^7$ and $R^8$ together form a ring structure; and B and B' are each independently selected from unsubstituted aryl, substituted aryl, unsubstituted heteroaryl, substituted heteroaryl, alkenyl, and alkynyl, or B and B' taken together form a ring structure.

2. The photochromic compound of claim 1, wherein independently for Formulas (Ia) and (Ib), one of, $R^3$ is, $R^4$ is, $R^5$ is, $R^6$ is, B is substituted with, and B' is substituted with,
in each case independently, a group L represented by the following Formula (III),

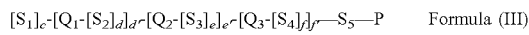   Formula (III)

wherein:
(a) $Q_1$, $Q_2$, and $Q_3$ for each occurrence, are independently selected from a divalent group selected from unsubstituted aryl, substituted aryl, unsubstituted heteroaryl, substituted heteroaryl, unsubstituted cycloalkyl, substituted cycloalkyl, unsubstituted heterocycloalky, and substituted heterocycloalkyl;
wherein the aryl substituents, heteroaryl substituents, cycloalkyl substituents, and heterocycloalkyl substituents are each independently selected from P, liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl;
wherein said straight-chain $C_1$-$C_{18}$ alkyl and branched $C_1$-$C_{18}$ alkyl are mono-substituted with a group selected from cyano, halogen, and $C_1$-$C_{18}$ alkoxy; or
wherein said straight-chain $C_1$-$C_{18}$ alkyl and branched $C_1$-$C_{18}$ alkyl are poly-substituted with at least two groups independently selected from halogen, -M(T)$_{(v-1)}$ and -M(OT)$_{(v-1)}$, wherein M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M;
(b) c, d, e, and f are each independently chosen from an integer of 1 to 20; and each $S_1$, $S_2$, $S_3$, $S_4$, and $S_5$ is independently chosen for each occurrence from a spacer unit selected from:
  (i) alkylene, substituted alkylene, haloalkylene, substituted haloalkylene, —Si(CH$_2$)$_g$—, and —Si[(CH$_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from $C_1$-$C_{18}$ alkyl, $C_3$-$C_{10}$ cycloalkyl and aryl;
  (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_{18}$ alkyl, $C_3$-$C_{10}$ cycloalkyl and aryl, and Z' for each occurrence is independently selected from $C_1$-$C_{18}$ alkyl, $C_3$-$C_{10}$ cycloalkyl and aryl; and
  (iii) —O—, —C(=O)—, —C≡C—, —N=N—, —S—, —S(=O)—, —(O=)S(=O)—, —(O=)S(=O)O—, —O(O=)S(=O)O— and straight-chain or branched $C_1$-$C_{24}$ alkylene residue, said $C_1$-$C_{24}$ alkylene residue being unsubstituted, mono-substituted by cyano or halogen, or poly-substituted by halogen,
provided, that when two spacer units comprising heteroatoms are linked together the spacer units are linked so that heteroatoms are not directly linked to each other, and the bond between $S_5$ and P is free of two heteroatoms linked to each other;
(c) P for each occurrence is independently selected from hydroxy, amino, $C_2$-$C_{18}$ alkenyl, $C_2$-$C_{18}$ alkynyl, azido, silyl, siloxy, silylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, allyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$)alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$)alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylene, acryloyl, acryloyloxy($C_1$-$C_{18}$)alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, male imide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro ($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound; and
(d) d', e' and f' are each independently chosen from 0, 1, 2, 3, and 4, provided that the sum of d'+e'+f' is at least 1.

3. The photochromic compound of claim 2, wherein independently for each group L represented by Formula (III),
(a) $Q_1$, $Q_2$, and $Q_3$ for each occurrence, are independently selected from unsubstituted aryl, substituted aryl, unsubstituted cycloalkyl, and substituted cycloalkyl,
(b) each $S_1$, $S_2$, $S_3$, $S_4$, and $S_5$ is independently chosen for each occurrence from a spacer unit selected from,
  (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl, and
  (iii) —O—, —C(=O)—, —C≡C—, —N=N—, —S—, —S(=O)—, and straight-chain or branched $C_1$-$C_{12}$ alkylene residue, said $C_1$-$C_{12}$ alkylene residue being unsubstituted, mono-substituted by cyano or halogen, or poly-substituted by halogen, and
(c) P for each occurrence is independently selected from hydrogen, hydroxy, amino, $C_2$-$C_8$ alkenyl, $C_2$-$C_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, $C_1$-$C_8$ alkyl aminocarbonyl, aminocarbonyl($C_1$-$C_8$)alkyl, $C_1$-$C_8$ alkyloxycarbonyloxy, halocarbonyl, aryl, hydroxy($C_1$-$C_8$)alkyl, $C_1$-$C_8$ alkyl, $C_1$-$C_8$ alkoxy, amino($C_1$-$C_8$)alkyl, $C_1$-$C_8$ alkylamino, di-($C_1$-$C_8$)alkylamino, $C_1$-$C_8$ alkyl($C_1$-$C_8$)alkoxy, $C_1$-$C_8$ alkoxy($C_1$-$C_8$)alkoxy, nitro, poly($C_1$-$C_8$)alkyl ether, ($C_1$-$C_8$)alkyl($C_1$-$C_8$)alkoxy($C_1$-$C_8$)alkyl, polyethyleneoxy, polypropyleneoxy, ethylene, acryloyl, acryloyloxy($C_1$-$C_{18}$)alkyl, methacryloyl, methacryloyloxy($C_1$-$C_8$) alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, and vinyl ester.

4. The photochromic compound of claim 3, wherein independently for each group L represented by Formula (III),
(b) each $S_1$, $S_2$, $S_3$, $S_4$, and $S_5$ is independently chosen for each occurrence from a spacer unit selected from,
   (ii) —N(Z)—, —C(Z)=C(Z)—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl, and
   (iii) —O—, —C(=O)—, —C≡C—, and straight-chain or branched $C_1$-$C_6$ alkylene residue, said $C_1$-$C_6$ alkylene residue being unsubstituted, mono-substituted by cyano or halogen, or poly-substituted by halogen, and
(c) P for each occurrence is independently selected from hydrogen, hydroxy, amino, $C_2$-$C_8$ alkenyl, $C_2$-$C_8$ alkynyl, and aryl.

5. The photochromic compound of claim 2, wherein each group L is independently selected from,

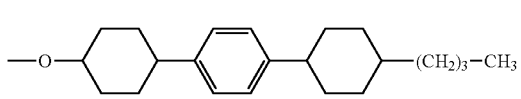

L(1)

4-[4-(4-butyl-cyclohexyl)-phenyl]-cyclohexyloxy

L(2)

4″-butyl-[1,1′;4′,1″]tercyclohexan-4-yloxy

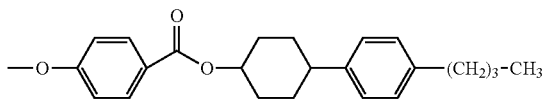

L(3)

4-[4-(4-butyl-phenyl)-cyclohexyloxycarbonyl]-phenoxy

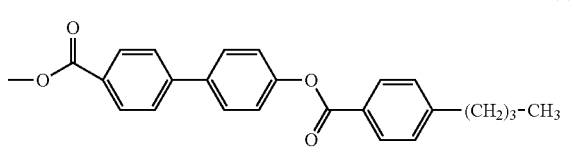

L(4)

4′-(4-butyl-benzoyloxy)-biphenyl-4-carbonyloxy

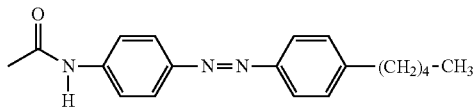

L(5)

4-(4-pentyl-phenylazo)-phenylcarbamoyl

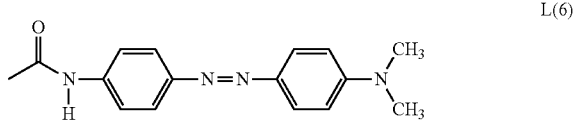

L(6)

4-(4-dimethylamino-phenylazo)-phenylcarbamoyl

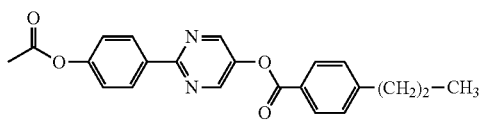

L(7)

{4-[5-(4-propyl-benzoyloxy)-pyrimidin-2-yl]-phenyl} ester

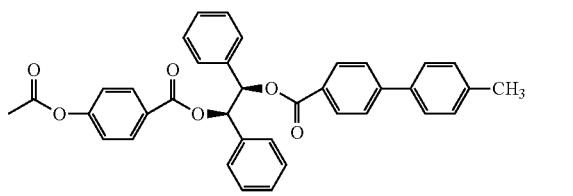

L(8)

{4-[2-(4′-methyl-biphenyl-4-carbonyloxy)-1,2-diphenylethoxycarbonyl]-phenyl} ester

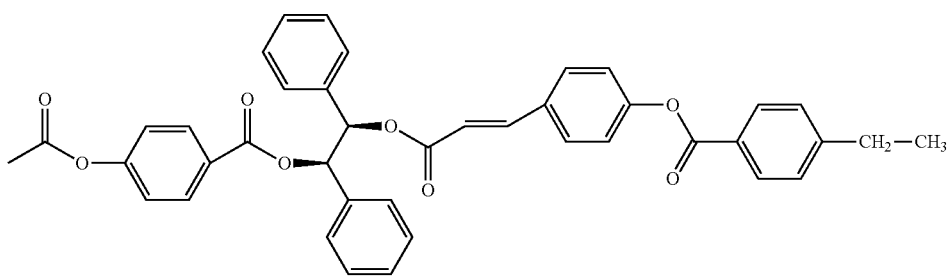

L(9)

[4-(1,2-diphenyl-2-{3-[4-(4-propyl-benzoyloxy)-phenyl]-acryloyloxy}-ethoxycarbonyl)-phenyl] ester

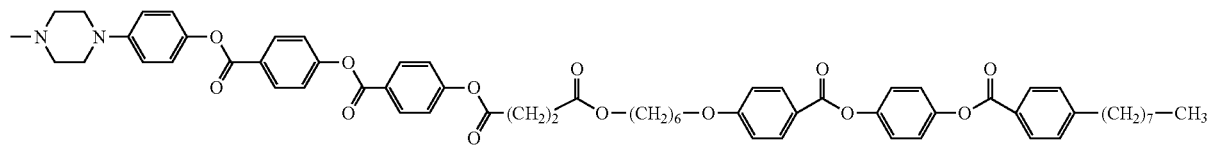

L(10)

4-[4-(4-{4-[3-(6-{4-[4-(4-nonyl-benzoyloxy)-phenoxycarbonyl]-phenoxy}-hexyloxycarbonyl)-propionyloxy]-benzoyloxy}-benzoyloxy)-phenyl]-piperazin-1-yl

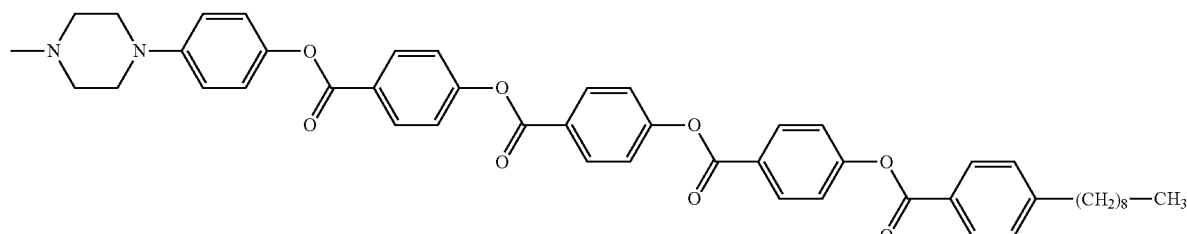

L(11)

{4-[4-(4-{4-[4-(4-nonyl-benzoyloxy)-benzoyloxy]-benzoyloxy}-benzoyloxy)-phenyl]-piperazin-1-yl}

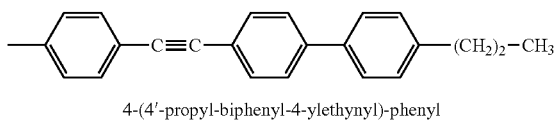

L(12)

4-(4′-propyl-biphenyl-4-ylethynyl)-phenyl

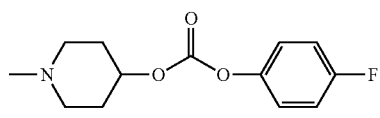

L(13)

4-(4-fluoro-phenoxycarbonyloxy)-piperidin-1-yl

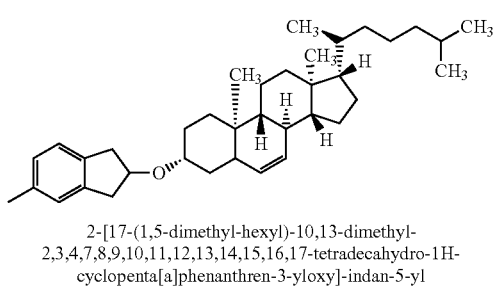

L(14)

2-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-indan-5-yl

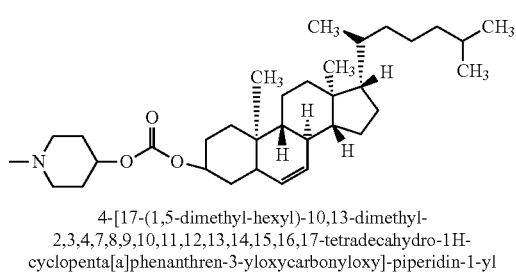

L(15)

4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl

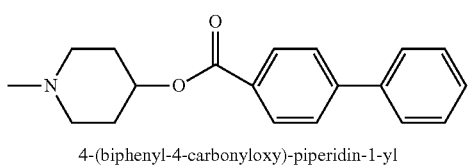

L(16)

4-(biphenyl-4-carbonyloxy)-piperidin-1-yl

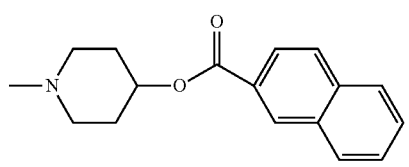

L(17)

4-(naphthalene-2-carbonyloxy)-piperidin-1-yl

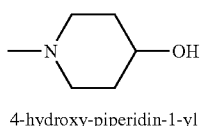

L(18)

4-hydroxy-piperidin-1-yl

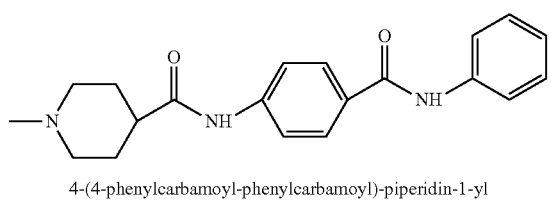

L(19)

4-(4-phenylcarbamoyl-phenylcarbamoyl)-piperidin-1-yl

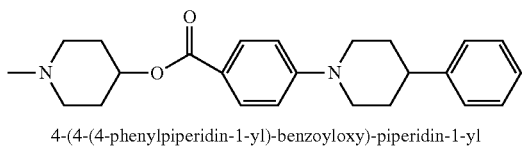

L(20)

4-(4-(4-phenylpiperidin-1-yl)-benzoyloxy)-piperidin-1-yl

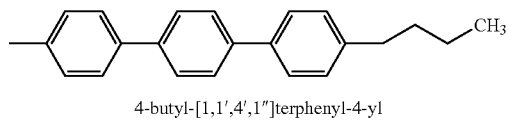

L(21)

4-butyl-[1,1′,4′,1″]terphenyl-4-yl

L(22)

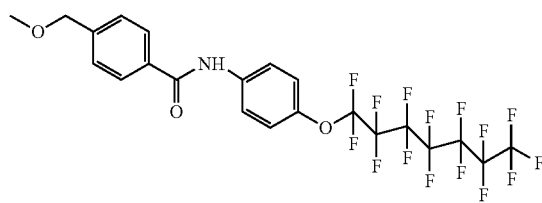

4-4(pentadecafluoroheptyloxy-phenylcarbamoyl)-benzyloxy

L(23)

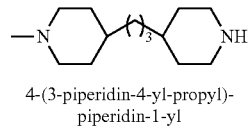

4-(3-piperidin-4-yl-propyl)-
piperidin-1-yl

L(24)

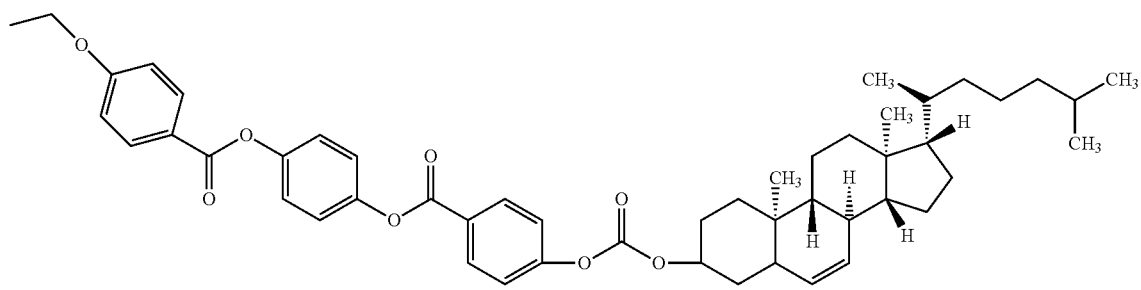

4-(4-{4-[17-(1,5-dimethyl-hexyl)-10,13-dimethyl-
2,3,4,7,8,9,10,11,12,13,14,15,16,17-tetradecahydro-1H-
cyclopenta[a]phenanthren-3-yloxycarbonyloxy]-benzoyloxy}-phenoxycarbonyl)-
phenoxymethyl

L(25)

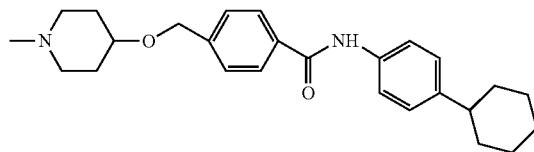

4-[4-(4-cyclohexyl-phenylcarbamoyl)-benzyloxy]-piperidin-1-yl

L(26)

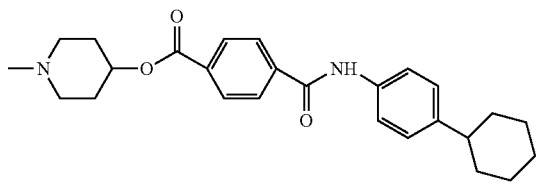

4-[4-(4-cyclohexyl-phenylcarbamoyl)-benzyloxy]-piperidin-1-yl

L(27)

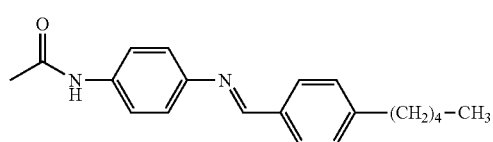

N-{4-[(4-pentyl-benzylidene)-amino]-phenyl}-acetamidyl

L(28)

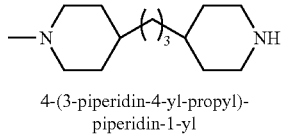

4-(3-piperidin-4-yl-propyl)-
piperidin-1-yl

L(29)

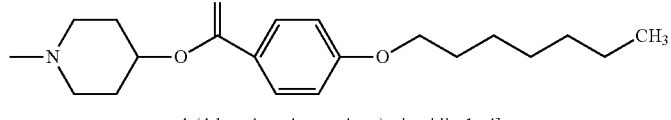

4-(4-hexyloxy-benzoyloxy)-piperidin-1-yl]

L(30)

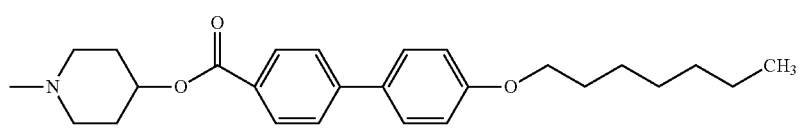

4-(4'-hexyloxy-biphenyl-4-carbonyloxy)-piperidin-1-yl

L(31)

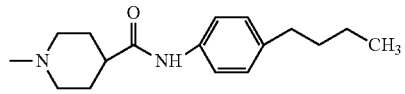

4-(4-butyl-phenylcarbamoyl)-piperidin-1-yl

L(32a)

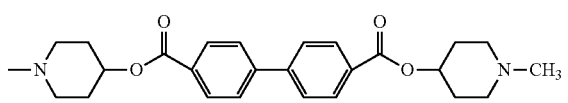

1-methyl-4-((4'-(((1-methylpiperidin-4-yl)oxy)carbonyl)-[1,1'-
biphenyl]-4-carbonyl)oxy)piperidin-1-yl -continued L(32b)

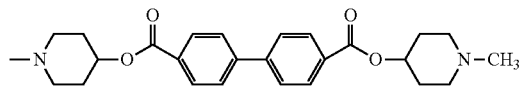

bis(1-yl-piperidin-4-yl) [1,1'-biphenyl]-4,4'-dicarboxylate

L(33)

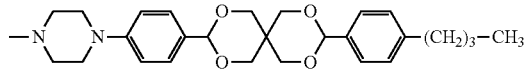

4-(4-(9-(4-butylphenyl)-2,4,8,10-tetraoxaspiro[5.5]undec-3-yl)phenyl)piperazin-1-yl

L(34)

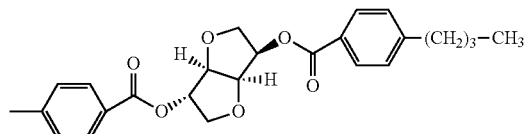

4-(6-(4-butylphenyl)carbonyloxy-(4,8-dioxabicyclo[3.3.0]oct-2-yl))oxycarbonyl)phenyl

L(35)

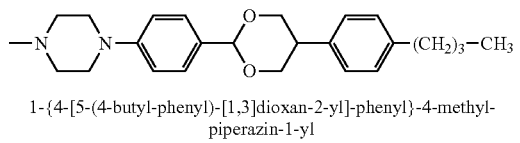

1-{4-[5-(4-butyl-phenyl)-[1,3]dioxan-2-yl]-phenyl}-4-methyl-piperazin-1-yl

L(36)

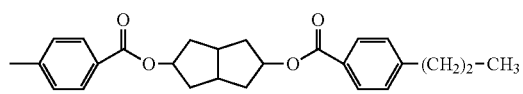

4-(7-(4-propylphenylcarbonyloxy)bicyclo[3.3.0]oct-2-yl)oxycarbonyl)phenyl

L(37)

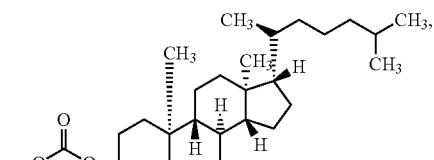

4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy L(a)

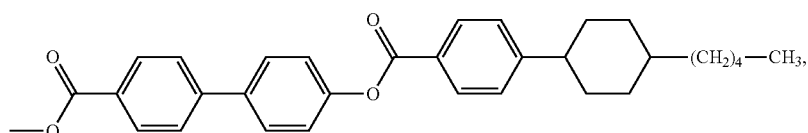

L(b)

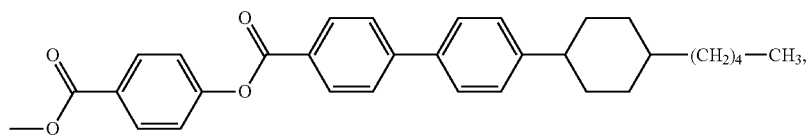

L(c)

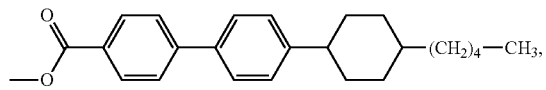

L(d)

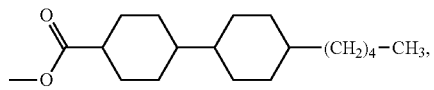

L(e)

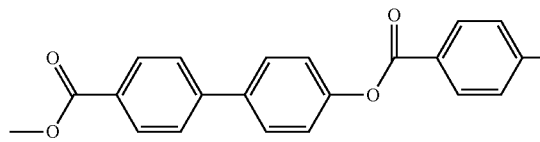

L(f)

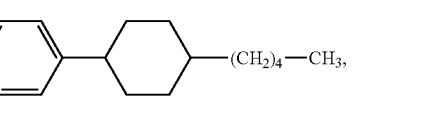

L(g)

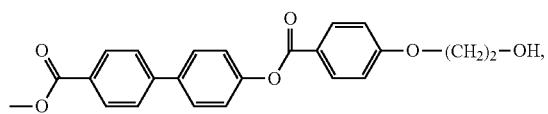

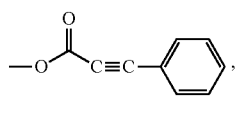

L(h)

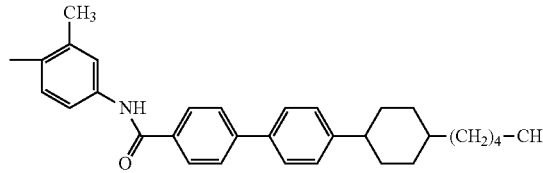

L(i)

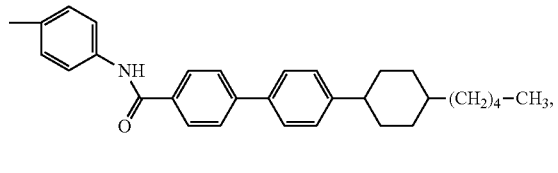

-continued
L(j)
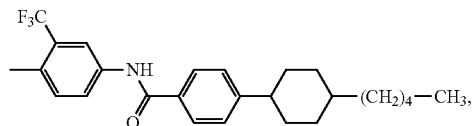
L(k)
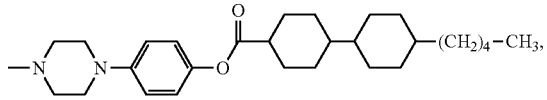
L(l)
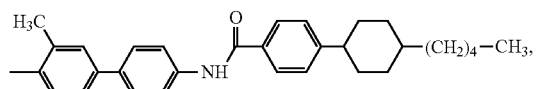
L(m)
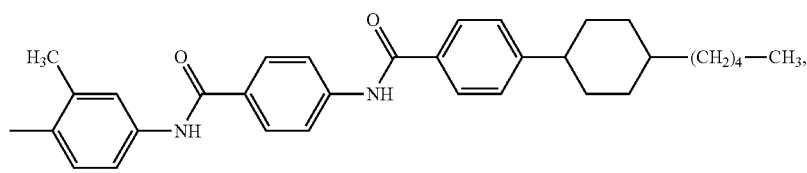
L(n)
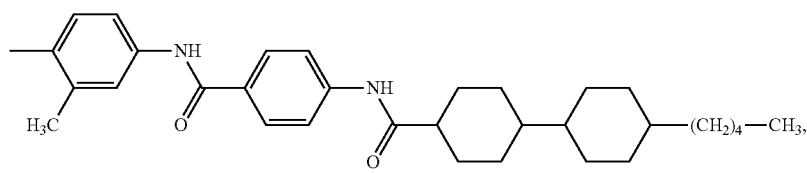
L(o)
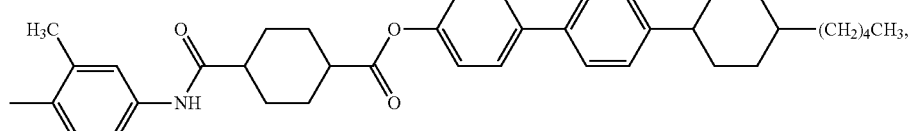
L(p)
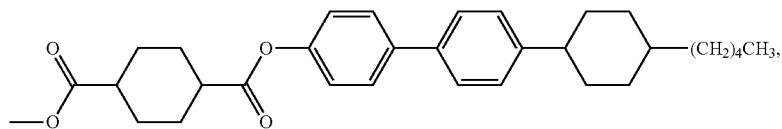
L(q)
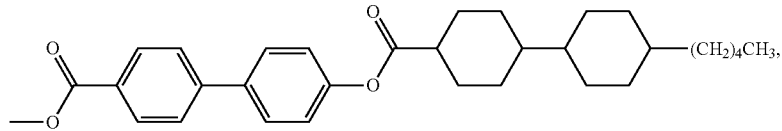
L(r)
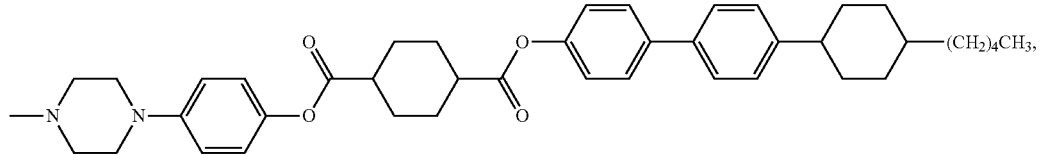
L(s)
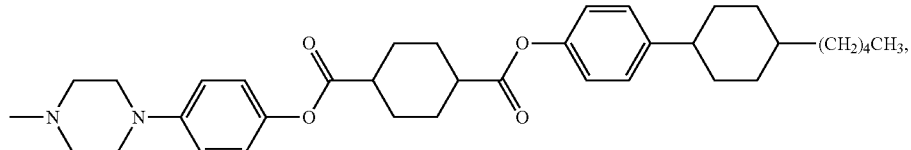
L(t)
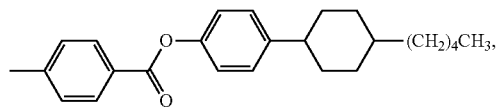
L(u)
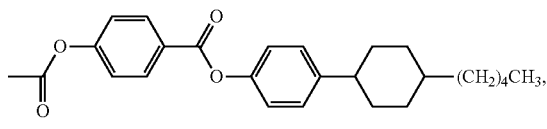

-continued

L(w): [structure: methylphenyl-piperazine-methoxyphenyl]

L(x): [structure with multiple benzoate esters ending in O—(CH₂)₄CH₃]

L(y): [structure: benzoate with tetrahydropyranyloxy group]

L(z): [structure: phenyl benzoate with OH]

L(aa): [structure: benzoate-benzoate-THP-oxy]

L(ab): [structure: methyl 4-hydroxybenzoate]

L(ac): —C≡C—C(CH₃)₂—OH

L(ad): —O—S(=O)₂—CF₃

L(ae): [structure: acetoxy-phenyl-cyclohexyl-(CH₂)₄CH₃]

L(af): [structure: acetoxy-cyclohexyl-phenyl-ester-cyclohexyl-cyclohexyl-(CH₂)₄CH₃]

L-DC-(a) (4-trans-(4-pentylcyclohexyl)benzamido)phenyl,

L-DC-(b) (4-(4-trans-(4-pentylcyclohexyl)phenoxy)carbonyl) phenyl,

L-DC-(c) 4-(4-(4-trans-(4-pentylcyclohexyl)phenyl)benzamido) phenyl,

L-DC-(d) 4-((trans-(4′-pentyl-[1,1′-bi(cyclohexan)]-4-yl)oxy)carbonyl)phenyl,

L-DC-(e) 4-(4′-(4-pentylcyclohexyl)-[1,1′-biphenyl]-4-ylcarboxamido)phenyl,

L-DC-(f) 4-((4′-(4-pentylcyclohexyl)-[1,1′-biphenyl]-4-carbonyl)oxy)benzamido,

L-DC-(g) 4-(4′-(4-pentylcyclohexyl)-[1,1′-biphenyl]-, 4-carbonyl)piperazin-1-yl

L-DC-(h) 4-(4-(4-trans-(4-pentylcyclohexyl) phenyl)benzamido)-2-(trifluoromethyl)phenyl, L-DC-(i) 2-methyl-4-trans-(4-((4¢-trans-(4-pentylcyclohexyl)biphenyl-4-, yloxy)carbonyl)cyclohexanecarboxamido)phenyl L-DC-(j) 4′-(4′-pentylbi(cyclohexane-4-)carbonyloxy)biphenylcarbonyloxy, L-DC-(k) 4-(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy), and carbonyl)piperazin-1-yl L-DC-(l) 4-((S)-2-methylbutoxy)phenyl)-10-(4-(((3R,3aS,6S,6aS)-6-(4′-trans-(4-pentylcyclohexyl)biphenylcarbonyloxy) hexahydrofuro[3,2-b]furan-3-yloxy)carbonyl)phenyl 6. A photochromic compound represented by the following Formula (IV)

$$L^1\text{-}(PC)_{n'}\quad\text{Formula (IV)}$$

wherein,
n' is at least 2,
PC independently for each n is a residue of said photochromic compound of claim 1, and
$L^1$ is a multivalent linking group selected from,
a multivalent polymer,
a multivalent hydrocarbyl group,
a multivalent substituted hydrocarbyl group,
a multivalent interrupted hydrocarbyl group, and
a multivalent substituted interrupted hydrocarbyl group,
wherein each multivalent interrupted hydrocarbyl group and each multivalent substituted interrupted hydrocarbyl group, are each independently interrupted with at least one interrupting group selected from the group consisting of —O—, —S—, —C(O)—, —C(O)O—, —OC(O)O—, —B($R_{11}$')—, —P($R_{11}$')—, —P(O)($R_{11}$')—, —S(O)—, —SO$_2$—, —N=N—, —C(O)N($R_{11}$')—, —OC(O)N($R_{11}$')—, —N($R_{11}$')C(O)N($R_{11}$')—, —N($R_{11}$')— where $R_{11}$' in each case is independently selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more interrupting groups thereof.

7. The photochromic compound of claim 6, wherein
said multivalent polymer is selected from multivalent polyurethane, multivalent polyester, multivalent polyether, multivalent poly(meth)acrylate, multivalent polyvinylalcohol, multivalent polycarbonate, multivalent polysiloxane, and multivalent cyclic polysiloxane, and said multivalent hydrocarbyl group, said multivalent substituted hydrocarbyl group, said multivalent interrupted hydrocarbyl group, and said multivalent substituted interrupted hydrocarbyl group, each independently comprise a residue selected from, a residue of a polyisocyanate, a residue of a polyol, a residue of a polycarboxylic acid, a residue of a polycarbonate functional material, and combinations thereof.

8. A photochromic composition comprising the photochromic compound of claim 1.

9. A photochromic article comprising the photochromic compound of claim 1.

10. The photochromic article of claim 9, wherein said photochromic article is selected from ophthalmic articles, display articles, windows, mirrors, active liquid crystal cell articles, and passive liquid crystal cell articles.

11. The photochromic article of claim 10, wherein said photochromic article is selected from ophthalmic articles, and said ophthalmic articles are selected from corrective lenses, non-corrective lenses, contact lenses, intra-ocular lenses, magnifying lenses, protective lenses, and visors.

12. The photochromic article of claim 10, wherein said photochromic article is selected from display articles, and said display articles are selected from screens, monitors, and security elements.

* * * * *

UNITED STATES PATENT AND TRADEMARK OFFICE
CERTIFICATE OF CORRECTION

PATENT NO. : 10,501,477 B2  
APPLICATION NO. : 15/556672  
DATED : December 10, 2019  
INVENTOR(S) : Jun Deng et al.

Page 1 of 1

It is certified that error appears in the above-identified patent and that said Letters Patent is hereby corrected as shown below:

In the Claims

Column 63, Line 49, Claim 1, delete "forma" and insert -- form a --

Column 64, Line 49, Claim 1, delete "forma" and insert -- form a --

Column 64, Line 63, Claim 1, delete "forma" and insert -- form a --

Column 64, Line 67, Claim 1, delete "forma" and insert -- form a --

Column 65, Line 7, Claim 2, delete "$[S_1]_c$" and insert -- --$[S_1]_c$ --

Column 65, Line 14, Claim 2, delete "heterocycloalky," and insert -- heterocycloalkyl, --

Column 66, Line 28, Claim 2, delete "male imide" and insert -- maleimide --

Column 70, Line 19, Claim 5, delete "-[1,1',4',1"]" and insert -- -[1,1';4',1"] --

Column 79, Line 2, Claim 6, delete "(IV)" and insert -- (IV), --

Column 79, Line 22, Claim 6, after "--P(O)($R_{11}$') --" insert -- , --

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*